(12) United States Patent
Nagao et al.

(10) Patent No.: US 9,391,288 B2
(45) Date of Patent: *Jul. 12, 2016

(54) LIGHT EMITTING DEVICE MATERIAL AND LIGHT EMITTING DEVICE

(75) Inventors: Kazumasa Nagao, Shiga (JP); Tsuyoshi Tominaga, Shiga (JP); Jinwoo Kwon, Seoul (KR)

(73) Assignee: TORAY INDUSTRIES, INC., Tokyo (JP)

( * ) Notice: Subject to any disclaimer, the term of this patent is extended or adjusted under 35 U.S.C. 154(b) by 296 days.

This patent is subject to a terminal disclaimer.

(21) Appl. No.: 14/116,737

(22) PCT Filed: May 8, 2012

(86) PCT No.: PCT/JP2012/061731
§ 371 (c)(1),
(2), (4) Date: Nov. 8, 2013

(87) PCT Pub. No.: WO2012/153725
PCT Pub. Date: Nov. 15, 2012

(65) Prior Publication Data
US 2014/0070204 A1    Mar. 13, 2014

(30) Foreign Application Priority Data

May 12, 2011 (JP) ................................. 2011-106966
Feb. 20, 2012 (JP) ................................. 2012-033627

(51) Int. Cl.
*H01L 51/50* (2006.01)
*C07D 209/86* (2006.01)
*C09K 11/06* (2006.01)
*H01L 51/00* (2006.01)
*H05B 33/14* (2006.01)
*C09B 57/00* (2006.01)

(52) U.S. Cl.
CPC .............. *H01L 51/50* (2013.01); *C07D 209/86* (2013.01); *C09B 57/00* (2013.01); *C09B 57/008* (2013.01); *C09K 11/06* (2013.01); *H01L 51/0072* (2013.01); *H05B 33/14* (2013.01); *C09K 2211/1007* (2013.01); *C09K 2211/1029* (2013.01); *H01L 51/0085* (2013.01); *H01L 51/5016* (2013.01); *H01L 51/5056* (2013.01)

(58) Field of Classification Search
None
See application file for complete search history.

(56) References Cited

U.S. PATENT DOCUMENTS

| | | | |
|---|---|---|---|
| 2004/0265630 A1* | 12/2004 | Suh ..................... | H01L 51/5052 428/690 |
| 2008/0233387 A1* | 9/2008 | Kambe ............... | H01L 51/0072 428/332 |
| 2012/0235136 A1 | 9/2012 | Ogawa et al. | |

FOREIGN PATENT DOCUMENTS

| | | | |
|---|---|---|---|
| JP | 2005-68068 A | 3/2005 | |
| JP | 2008-112984 A | 5/2008 | |
| JP | 2011-190239 A | 9/2011 | |
| WO | WO 2011/049325 | * 4/2011 | ............. C09K 11/06 |
| WO | WO 2011/081061 A1 | 7/2011 | |
| WO | WO 2012/023947 A1 | 2/2012 | |

OTHER PUBLICATIONS

PCT/ISA/210—International Search Report mailed on Jul. 24, 2012, issued in PCT/JP2012/061731.
Search Report dated Aug. 29, 2014 for European Application No. 12781687.4.

* cited by examiner

*Primary Examiner* — Gregory Clark
(74) *Attorney, Agent, or Firm* — Birch, Stewart, Kolasch & Birch, LLP

(57) ABSTRACT

The present invention provides an organic thin-film light emitting device having both high luminance efficiency and durability due to the use of a light emitting device material containing a compound having a specific carbazole skeleton.

17 Claims, No Drawings

LIGHT EMITTING DEVICE MATERIAL AND LIGHT EMITTING DEVICE

TECHNICAL FIELD

The present invention relates to a light emitting device capable of converting electric energy into light, and a light emitting device material to be used for the same. In particular, the present invention relates to a light emitting device capable of being used for areas such as display devices, flat-panel displays, backlight, lighting, interior design, labels, signboards, electrophotography machines, and light signal generators, and also to a light emitting device material to be used for the same.

BACKGROUND ART

Researches on an organic thin-film light emitting device in which electrons injected from a cathode and holes injected from an anode emit light when they are recombined in an organic fluorescent body held by both electrodes have been actively conducted in recent years. This light emitting device is characteristic for high luminance light emission in the form of a thin type and under a low driving voltage, and multicolor light emission due to selection of a fluorescent material, and has been paid attention.

Such researches have undergone many studies for practical use since C. W. Tang et al. of Kodak Co., Ltd. showed that an organic thin-film device emits light at high luminance, and organic thin-film light emitting devices have steadily come into practical use as they have been employed in main displays of mobile phones, and the like. However, there are still many technical problems and, especially, attainment of both increased efficiency and prolonged life of a device is one of the major problems.

The driving voltage of a device greatly depends on a carrier transporting material that transports carriers such as a hole and an electron to an emissive layer. Among them, materials having a carbazole skeleton are known as materials to transport holes (hole transporting materials) (see, for example, Patent Documents 1 and 2). Further, the material having a carbazole skeleton has a high triplet level, and is therefore known as a host material of an emissive layer (see, for example, Patent Document 3).

PRIOR ART DOCUMENTS

Patent Documents

Patent Document 1: Japanese Patent Laid-open Publication No. 8-3547
Patent Document 2: Korean Patent Application Publication No. 2010-0079458
Patent Document 3: Japanese Patent Laid-open Publication No. 2003-133075

SUMMARY OF THE INVENTION

Problems to be Solved by the Invention

However, conventional technologies were difficult to reduce the driving voltage of a device sufficiently, and even if they had been able to reduce the driving voltage, the luminance efficiency and the durable life of a device were insufficient. Thus, technologies capable of realizing both high luminance efficiency and durable life have not been found yet.

An object of the present invention is to solve such problems with the conventional technologies and provide an organic thin-film light emitting device that has improved luminance efficiency and durable life.

Solutions to the Problems

The present invention is a light emitting device material including a carbazole skeleton-containing compound represented by the following general formula (1).

[Chemical Formula 1]

[Chemical Formula 1]

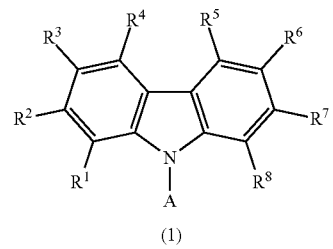

(1)

wherein $R^1$ to $R^8$ may be the same or different and are each selected from the group consisting of hydrogen, an alkyl group, a cycloalkyl group, a heterocyclic group, an alkenyl group, a cycloalkenyl group, an alkynyl group, an alkoxy group, an alkylthio group, an aryl ether group, an aryl thioether group, an aryl group, a heteroaryl group, a halogen, a carbonyl group, a carboxyl group, an oxycarbonyl group, a carbamoyl group, an amino group, a silyl group, $-P(=O)R^9R^{10}$ and a group represented by the following general formula (3); $R^9$ and $R^{10}$ are each an aryl group or a heteroaryl group, wherein any one of $R^1$ to $R^8$ is a group represented by the following general formula (3), and is coupled at the position of any of $R^{51}$ to $R^{58}$ in the general formula (3), or at any position in a group represented by $R^{59}$, $R^1$ to $R^8$ include none of a dibenzofuran skeleton, a dibenzothiophene skeleton and a carbazole skeleton unless these groups are those represented by the general formula (3), and $R^1$ to $R^{10}$ include none of an anthracene skeleton and a pyrene skeleton; and A is a group represented by the following general formula (2).

[Chemical Formula 2]

[Chemical Formula 2]

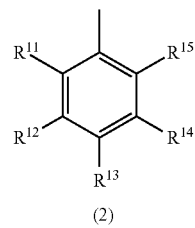

(2)

wherein $R^{11}$ to $R^{15}$ may be the same or different and each hydrogen or a substituted or unsubstituted aryl group, wherein at least two of $R^{11}$ to $R^{15}$ are substituted or unsubstituted aryl groups, and $R^{11}$ to $R^{15}$ include none of an anthracene skeleton and a pyrene skeleton.

[Chemical Formula 3]

[Chemical Formula 3]

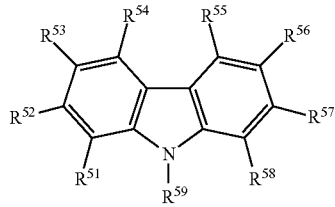

(3)

wherein $R^{51}$ to $R^{59}$ may be the same or different and are each selected from the group consisting of hydrogen, an alkyl group, a cycloalkyl group, a heterocyclic group, an alkenyl group, a cycloalkenyl group, an alkynyl group, an alkoxy group, an alkylthio group, an aryl ether group, an aryl thioether group, an aryl group, a heteroaryl group, a halogen, a carbonyl group, a carboxyl group, an oxycarbonyl group, a carbamoyl group, an amino group, a silyl group and —P(=O)$R^{60}R^{61}$; and $R^{60}$ and $R^{61}$ are each an aryl group or a heteroaryl group, wherein the position of any one of $R^{51}$ to $R^{58}$, or any position in a group represented by $R^{59}$ is coupled at the position of any of $R^1$ to $R^8$ in the general formula (1), $R^{51}$ to $R^{59}$ include none of a dibenzofuran skeleton, a dibenzothiophene skeleton and a carbazole skeleton unless these groups are coupled at the position of any of $R^1$ to $R^8$ in the general formula (1), and $R^{51}$ to $R^{61}$ include none of an anthracene skeleton and a pyrene skeleton.

Effects of the Invention

According to the present invention, there can be provided an organic electric field light emitting device having high luminance efficiency, and further having sufficient durable life.

EMBODIMENTS OF THE INVENTION

The compound represented by the general formula (1) in the present invention is described in detail below.

[Chemical Formula 4]

[Chemical Formula 4]

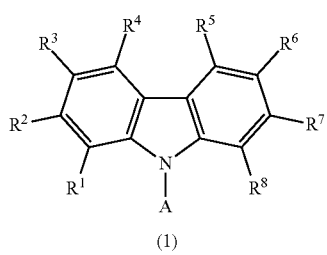

(1)

wherein $R^1$ to $R^8$ may be the same or different and are each selected from the group consisting of hydrogen, an alkyl group, a cycloalkyl group, a heterocyclic group, an alkenyl group, a cycloalkenyl group, an alkynyl group, an alkoxy group, an alkylthio group, an aryl ether group, an aryl thioether group, an aryl group, a heteroaryl group, a halogen, a carbonyl group, a carboxyl group, an oxycarbonyl group, a carbamoyl group, an amino group, a silyl group, —P(=O)$R^9R^{10}$ and a group represented by the following formula (3); $R^9$ and $R^{10}$ are each an aryl group or a heteroaryl group, wherein any one of $R^1$ to $R^8$ is a group represented by the following general formula (3), and is coupled at the position of any of $R^{51}$ to $R^{58}$ in the general formula (3), or at any position in a group represented by $R^{59}$, $R^1$ to $R^8$ include none of a dibenzofuran skeleton, a dibenzothiophene skeleton and a carbazole skeleton unless these groups are those represented by the general formula (3), and $R^1$ to $R^{10}$ include none of an anthracene skeleton and a pyrene skeleton; and A is a group represented by the following general formula (2).

[Chemical Formula 5]

[Chemical Formula 5]

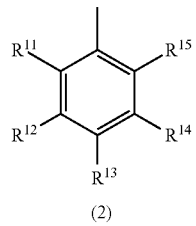

(2)

wherein $R^{11}$ to $R^{15}$ may be the same or different and each hydrogen or a substituted or unsubstituted aryl group, wherein at least two of $R^{11}$ to $R^{15}$ are substituted or unsubstituted aryl groups, and $R^{11}$ to $R^{15}$ include none of an anthracene skeleton and a pyrene skeleton.

[Chemical Formula 6]

[Chemical Formula 6]

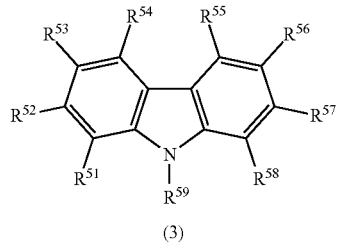

(3)

wherein $R^{51}$ to $R^{59}$ may be the same or different and are each selected from the group consisting of hydrogen, an alkyl group, a cycloalkyl group, a heterocyclic group, an alkenyl group, a cycloalkenyl group, an alkynyl group, an alkoxy group, an alkylthio group, an aryl ether group, an aryl thioether group, an aryl group, a heteroaryl group, a halogen, a carbonyl group, a carboxyl group, an oxycarbonyl group, a carbamoyl group, an amino group, a silyl group and —P(=O)$R^{60}R^{61}$; and $R^{60}$ and $R^{61}$ are each an aryl group or a heteroaryl group, wherein the position of any one of $R^{51}$ to $R^{58}$, or any position in a group represented by $R^{59}$ is coupled at the position of any of $R^1$ to $R^8$ in the general formula (1), $R^{51}$ to $R^{59}$ include none of a dibenzofuran skeleton, a dibenzothiophene skeleton and a carbazole skeleton unless these groups are coupled at the position of any of $R^1$ to $R^8$ in the general formula (1), and $R^{51}$ to $R^{61}$ include none of an anthracene skeleton and a pyrene skeleton.

Among these substituents, hydrogen may be deuterium. The alkyl group denotes a saturated aliphatic hydrocarbon group, such as a methyl group, an ethyl group, a n-propyl group, an isopropyl group, a n-butyl group, a sec-butyl group, or a tert-butyl group, and it may or may not have a substituent.

The additional substituent when the alkyl group is substituted is not particularly limited, and examples thereof may include an alkyl group, an aryl group, and a heteroaryl group, and this point is also common to the following descriptions. In addition, the number of carbon atoms in the alkyl group is not particularly limited, but from the viewpoints of easy availability and cost, it is usually within the range of 1 or more and 20 or less, more preferably 1 or more and 8 or less.

The cycloalkyl group denotes a saturated alicyclic hydrocarbon group, such as cyclopropyl, cyclohexyl, norbornyl, and adamantyl, and this may or may not have a substituent. The number of carbon atoms in the alkyl group moiety is not particularly limited, but is usually within the range of 3 or more and 20 or less.

The heterocyclic group denotes an aliphatic ring having an atom other than carbon in the ring, such as a pyran ring, a piperidine ring, and a cyclic amide, and this may or may not have a substituent. The number of carbon atoms in the heterocyclic group is not particularly limited, but is usually within the range of 2 or more and 20 or less.

The alkenyl group denotes an unsaturated aliphatic hydrocarbon group containing a double bond, such as a vinyl group, an allyl group, and a butadienyl group, and this may or may not have a substituent. The number of carbon atoms in the alkenyl group is not particularly limited, but is usually within the range of 2 or more and 20 or less.

The cycloalkenyl group denotes an unsaturated alicyclic hydrocarbon group containing a double bond, such as a cyclopentenyl group, a cyclopentadienyl group, and a cyclohexenyl group, and this may or may not have a substituent. The number of carbon atoms of the cycloalkenyl group is not specifically limited, but is usually within the range of 2 or more and 20 or less.

The alkynyl group denotes an unsaturated aliphatic hydrocarbon group containing a triple bond, such as an ethynyl group, and this may or may not have a substituent. The number of carbon atoms in the alkynyl group is not particularly limited, but is usually within the range of 2 or more and 20 or less.

The alkoxy group denotes a functional group in which an aliphatic hydrocarbon group is bound via an ether bond, such as a methoxy group, an ethoxy group and a propoxy group, and this aliphatic hydrocarbon group may or may not have a substituent. The number of carbon atoms in the alkoxy group is not particularly limited, but is usually within the range of 1 or more and 20 or less.

The alkylthio group is a group in which the oxygen atom of an ether bond of the alkoxy group is substituted with a sulfur atom. The hydrocarbon group of the alkylthio group may or may not have a substituent. The number of carbon atoms in the alkylthio group is not particularly limited, but is usually within the range of 1 or more and 20 or less.

The aryl ether group denotes a functional group in which an aromatic hydrocarbon group is bound via an ether bond, such as a phenoxy group, and the aromatic hydrocarbon group may or may not have a substituent. The number of carbon atoms in the aryl ether group is not particularly limited, but is usually within the range of 6 or more and 40 or less.

The aryl thioether group is a group in which the oxygen atom of an ether bond of the aryl ether group is substituted with a sulfur atom. The aromatic hydrocarbon group in the aryl ether group may or may not have a substituent. The number of carbon atoms in the aryl ether group is not particularly limited, but is usually within the range of 6 or more and 40 or less.

The aryl group represents an aromatic hydrocarbon group, such as a phenyl group, a naphthyl group, a biphenyl group, a fluorenyl group, a phenanthryl group, a fluoranthenyl group, a triphenylenyl group and a terphenyl group. The aryl group may or may not have a substituent. The number of carbon atoms in the aryl group is not particularly limited, but is usually within the range of 6 or more and 40 or less.

The heteroaryl group denotes a cyclic aromatic group having one or a plurality of atoms other than carbon in the ring, such as a furanyl group, a thiophenyl group, a pyridyl group, a quinolinyl group, a pyrazinyl group, a pyrimidinyl group, a triazinyl group, a naphthyridyl group, a benzofuranyl group, a benzothiophenyl group and an indolyl group, and this may be unsubstituted or substituted. The number of carbon atoms in the heteroaryl group is not particularly limited, but is usually within the range of 2 or more and 30 or less.

The halogen denotes fluorine, chlorine, bromine or iodine.

The carbonyl group, the carboxyl group, the oxycarbonyl group, and the carbamoyl group may or may not have a substituent, and examples of the substituent include an alkyl group, a cycloalkyl group and an aryl group, and these substituents may be further substituted.

The amino group may or may not have a substituent, and examples of the substituent include an aryl group and a heteroaryl group. Such a substituent may be further substituted.

The silyl group denotes a functional group having a bond with a silicon atom, such as a trimethylsilyl group, and this may or may not have a substituent. The number of carbon atoms in the silyl group is not particularly limited, but is usually within the range of 3 or more and 20 or less. In addition, the number of silicon atoms is usually within the range of 1 or more and 6 or less.

—P(=O)$R^9R^{10}$, —P(=O)$R^{24}R^{25}$ and —P(=O)$R^{75}R^{76}$ may or may not have a substituent, and examples of the substituent include an aryl group and a heteroaryl group. Such a substituent may be further substituted.

Hydrogen included in the various kinds of substituents described above may be deuterium.

Conventional compounds having a carbazole skeleton do not necessarily have sufficient performance as a light emitting device material. For example, 4,4'-di(9H-carbazol-9-yl)-1,1'-biphenyl (abbreviated name: CBP) and 1,3-di(9H-carbazol-9-yl)benzene (abbreviated name: mCP) are materials that are generally used as a phosphorescence host material and an exciton blocking material, but both have the problem that the driving voltage is high. In studies on improvement thereof, the present inventors focused on a high hole transporting ability and electron transporting ability of a carbazole skeleton-containing compound. Generally, the carbazole skeleton-containing compound has a property to transport charges of both a hole and an electron. The present inventors conceived that in contrast, the conventional compound has a low hole transporting ability, and therefore the ratio of holes entering an emissive layer is lower than that of electrons entering from an electron transporting layer, so that the balance of charges in the emissive layer is lost, leading to deterioration of device performance, and resultantly invented a carbazole skeleton-containing compound represented by the general formula (1) based on the above-mentioned hypothesis.

Preferably the carbazole skeleton-containing compound represented by the general formula (1) contains 2 carbazole skeletons per molecule, thereby providing a high thin film stability and an excellent heat resistance. When 3 or more carbazole skeletons are contained, there is the concern of thermal decomposition, and therefore the number of carbazole skeletons is preferably 2.

Further, $R^1$ to $R^8$ include none of a dibenzofuran skeleton, a dibenzothiophene skeleton and a carbazole skeleton unless these groups are those represented by the general formula (3). $R^{51}$ to $R^{59}$ include none of a dibenzofuran skeleton, a dibenzothiophene skeleton and a carbazole skeleton unless these groups are coupled at the position of any of $R^1$ to $R^8$ in the general formula (1). This is because, similarly to the reason described above, when the carbazole skeleton-containing compound of the present invention has as a substituent a carbazole skeleton, or a dibenzofuran skeleton or dibenzothiophene skeleton having a molecular weight comparable to that of the carbazole skeleton, the molecular weight may increase to cause thermal decomposition.

The carbazole skeleton-containing compound represented by the general formula (1) has as a substituent on N a phenyl group having at least two substituted or unsubstituted aryl groups, and therefore exhibits excellent performance in the electron blocking property. Since the number of aryl groups substituted with the phenyl group is not 1 but at least 2, the glass transition temperature (Tg) of the carbazole skeleton-containing compound represented by the formula (1) is increased, so that the electron blocking property is significantly enhanced. As a result, the charge balance in the emissive layer can be improved to enhance light emitting device performance such as luminance efficiency and lifetime. When the number of the aryl groups is 3 or more, synthesis of the compound becomes difficult because of three-dimensional jamming. Therefore, the number of the aryl groups is preferably 2. When the carbazole skeleton further has a group represented by the general formula (3), the hole transporting property is excellent. In particular, preferably at least two of $R^{11}$ to $R^{15}$ in the general formula (2) are substituted or unsubstituted phenyl groups. Preferably the substituent in this case does not massively extend the conjugation of the compound or lower the triplet level of the compound, and an alkyl group or a halogen is more preferred. These at least two substituted or unsubstituted phenyl groups may be the same or different. The hydrogen atom of the substituted or unsubstituted phenyl group may be deuterium.

$R^1$ to $R^{10}$ in the general formula (1) and $R^{11}$ to $R^{15}$ in the general formula (2) include none of an anthracene skeleton and a pyrene skeleton. That is, the carbazole skeleton-containing compound represented by the general formula (1) includes none of an anthracene skeleton and a pyrene skeleton in the molecule. This is because that the anthracene skeleton and pyrene skeleton themselves have a low triplet level, and when the carbazole skeleton-containing compound of the present invention has the substituent, the triplet level of the compound is lowered. When the carbazole skeleton-containing compound represented by the general formula (1) is used for a hole transporting layer, leak of triplet excitation energy occurs and luminance efficiency drops when the compound is in contact directly with an emissive layer containing a triplet emitter dopant if the triplet level is low. When the carbazole skeleton-containing compound represented by the general formula (1) is used for an emissive layer, an effect of trapping the excitation energy of a triplet emissive material cannot be sufficiently exhibited, and luminance efficiency drops.

In the carbazole skeleton-containing compound represented by the general formula (1), any one of $R^1$ to $R^8$ is a group represented by the general formula (3). In the group represented by the general formula (3), the position of any one of $R^{51}$ to $R^{58}$ or any position in a group represented by $R^{59}$ is used for coupling with $R^1$ to $R^8$. The phrase "$R^{53}$ is used for coupling with $R^3$" means that the $R^3$ moiety in the general formula (1) and the $R^{53}$ moiety in the general formula (3) are directly bound to each other. The phrase "any position in a group represented by $R^{59}$ is used for coupling with, for example, $R^{3}$" means that for example, when $R^{59}$ is a phenyl group, the $R^3$ moiety of the general formula (1) is directly bound at any position in the phenyl group.

In particular, $R^3$ being a group represented by the general formula (3) is preferred because the hole transporting ability is further enhanced.

Further, it is preferred that in the carbazole skeleton-containing compound represented by the general formula (1), A and $R^{59}$ are different groups. In this case, the molecule has an asymmetric structure, and therefore the effect of suppressing an interaction of carbazole skeletons is enhanced, so that a stable thin film can be formed, leading to enhancement of durability.

Among the compounds represented by the general formula (1) of the present invention, those in which the group represented by the general formula (3) is a group represented by the general formula (5) described later are preferred. At this time, any one of $R^{62}$ to $R^{74}$ is coupled at the position of any of $R^1$ to $R^8$ in the general formula (1). Other explanations regarding the substituents are as described later.

Among the compounds represented by the general formula (1) of the present invention, a carbazole skeleton-containing compound represented by the general formula (4) is preferred.

[Chemical Formula 7]

[Chemical Formula 7]

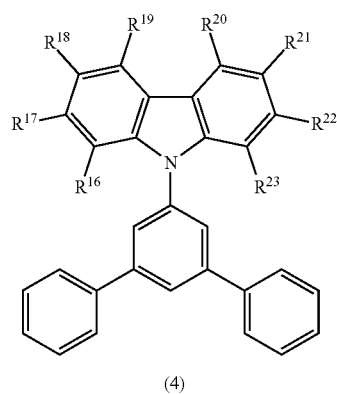

(4)

wherein $R^{16}$ to $R^{23}$ may be the same or different and are each selected from the group consisting of hydrogen, an alkyl group, a cycloalkyl group, a heterocyclic group, an alkenyl group, a cycloalkenyl group, an alkynyl group, an alkoxy group, an alkylthio group, an aryl ether group, an aryl thioether group, an aryl group, a heteroaryl group, a halogen, a carbonyl group, a carboxyl group, an oxycarbonyl group, a carbamoyl group, an amino group, a silyl group, —P(=O)$R^{24}R^{25}$ and a group represented by the following general formula (5); and $R^{24}$ and $R^{25}$ are each an aryl group or a heteroaryl group, wherein any one of $R^{16}$ to $R^{23}$ is a group represented by the following general formula (5), and is coupled at the position of any of $R^{62}$ to $R^{74}$ in the general formula (5), $R^{16}$ to $R^{23}$ include none of a dibenzofuran skeleton, a dibenzothiophene skeleton and a carbazole skeleton unless these groups are those represented by the general formula (5), and $R^{16}$ to $R^{23}$ include none of an anthracene skeleton and a pyrene skeleton.

[Chemical Formula 8]

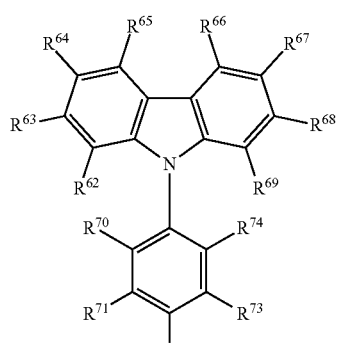

(5)

wherein $R^{62}$ to $R^{74}$ may be the same or different and are each selected from the group consisting of hydrogen, an alkyl group, a cycloalkyl group, a heterocyclic group, an alkenyl group, a cycloalkenyl group, an alkynyl group, an alkoxy group, an alkylthio group, an aryl ether group, an aryl thioether group, an aryl group, a heteroaryl group, a halogen, a carbonyl group, a carboxyl group, an oxycarbonyl group, a carbamoyl group, an amino group, a silyl group and —P(=O)$R^{75}R^{76}$; and $R^{75}$ and $R^{76}$ are each an aryl group or a heteroaryl group, wherein any one of $R^{62}$ to $R^{74}$ is coupled at the position of any of $R^{16}$ to $R^{23}$ in the general formula (4), $R^{62}$ to $R^{74}$ include none of a dibenzofuran skeleton, a dibenzothiophene skeleton and a carbazole skeleton unless these groups are coupled at the position of any of $R^{16}$ to $R^{23}$ in the general formula (4), and $R^{62}$ to $R^{76}$ include none of an anthracene skeleton and a pyrene skeleton.

Descriptions of these substituents are similar to those for the above general formula (1).

In the carbazole skeleton-containing compound represented by the general formula (4), any one of $R^{62}$ to $R^{74}$ in the general formula (5) is used for coupling with the base skeleton, i.e. a 9-([1,1':3',1''-terphenyl]-5'-yl)-9H-carbazole skeleton, so that coupled carbazoles exhibit a high hole transporting property, leading to enhancement of the hole mobility in the layer, thus making it possible to realize a low driving voltage. Further, when the carbazole skeleton is coupled, a high triplet level of the carbazole skeleton itself can be maintained, so that easy deactivation can be suppressed, resulting in achievement of high luminance efficiency. Further, the molecule has an asymmetric structure, and the effect of suppressing an interaction of carbazole skeletons is enhanced, so that a stable thin film can be formed, leading to enhancement of durability, thus being preferred.

Substituents of the carbazole skeleton-containing compound represented by the general formula (1) or (4) (except for the group represented by the general formula (3) or general formula (5)) are preferably hydrogen (including deuterium), an alkyl group, an aryl group or a heteroaryl group among those described above.

$R^{59}$ is preferably an aryl group, more preferably a phenyl group, a naphthyl group and a phenanthryl group. These groups may be further substituted with an alkyl group, a halogen, an aryl group or a heteroaryl group, but an anthracenyl group and a pyrenyl group are excluded. When a triplet level emissive material is used for the emissive layer, the triplet level of the carbazole skeleton-containing compound represented by the general formula (1) or (4) of the present invention becomes a very important value, and therefore $R^{59}$ is preferably a substituted or unsubstituted phenyl group having a high triplet level. Preferably the substituent in this case does not massively extend the conjugation of the compound or lower the triplet level of the compound, and an alkyl group or a halogen is more preferred.

The carbazole skeleton-containing compound represented by the above general formula (1) is not particularly limited, and specific examples include the compounds below. The compounds below are illustrative, and compounds other than those specified here are also suitably used as long as they are represented by the general formula (1).

[Chemical Formula 9]

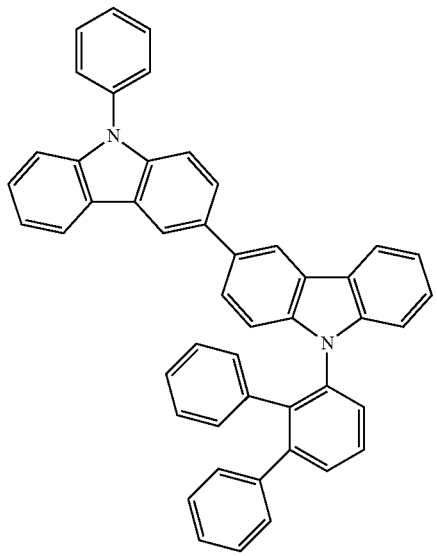

[1]

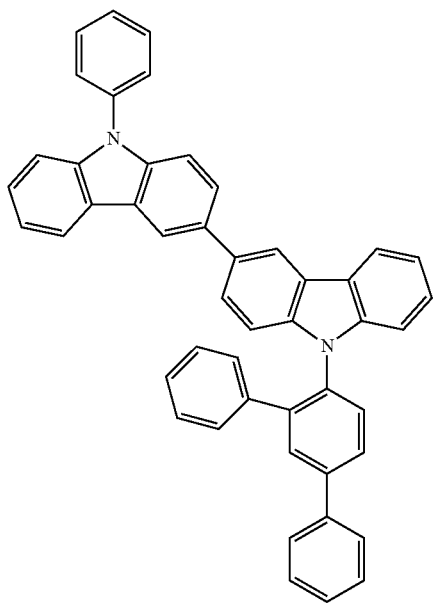

[2]

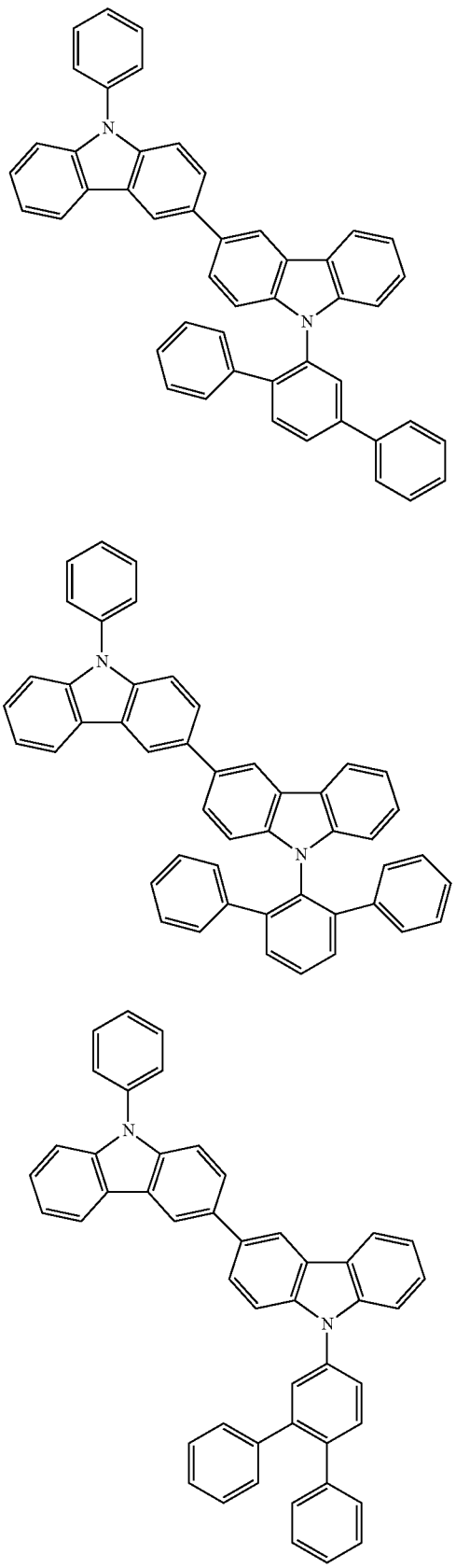
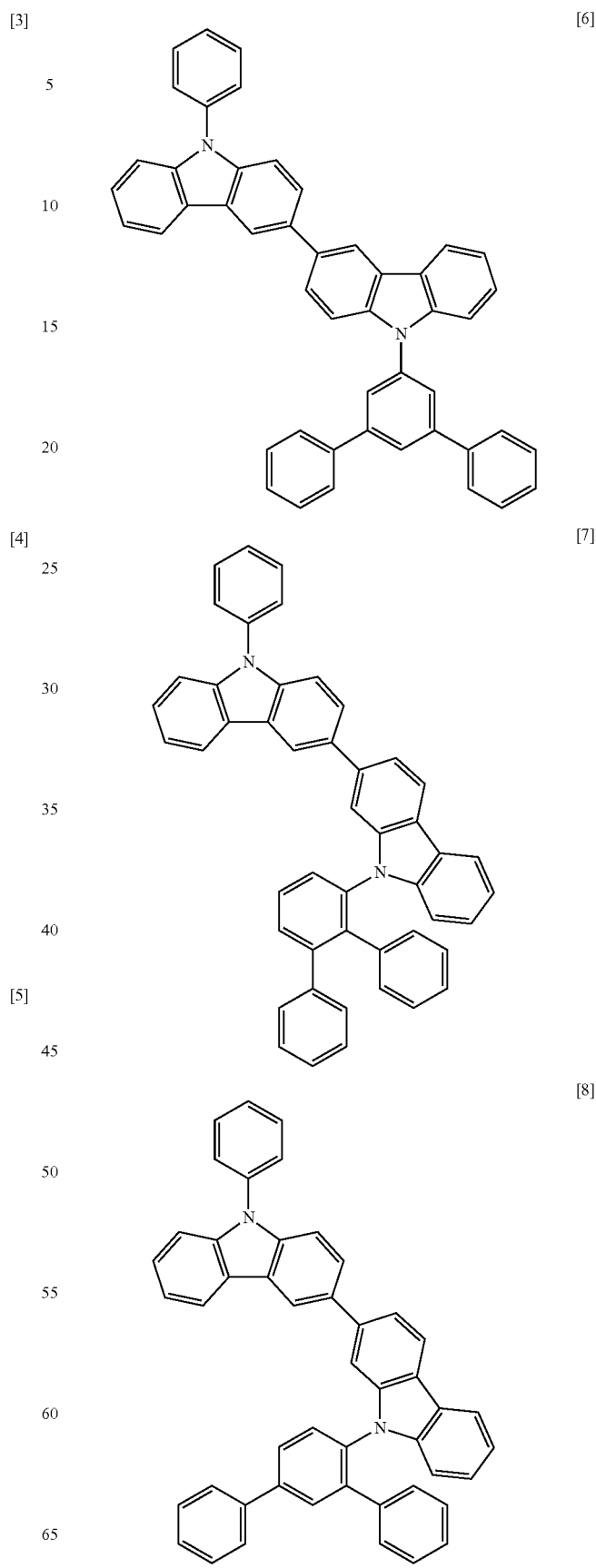

[9]
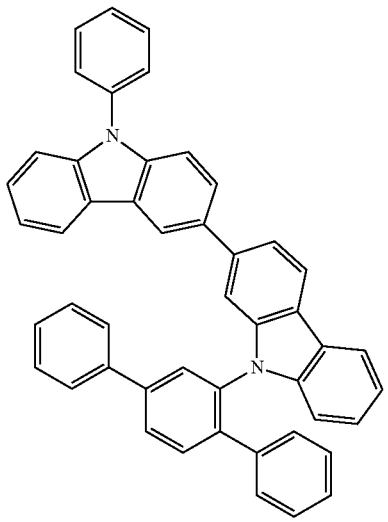
[10]
[11]
[12]
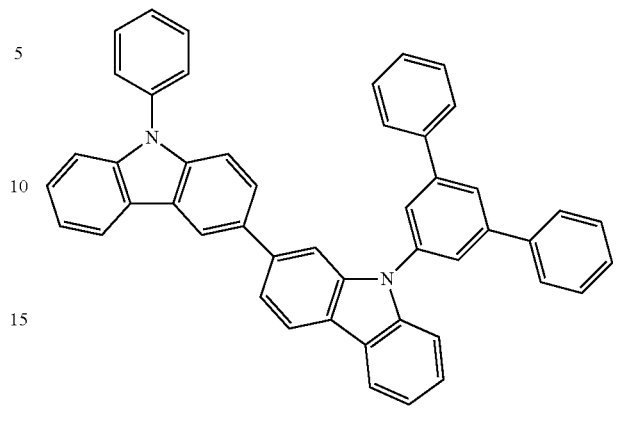
[Chemical Formula 10]
[Chemical Formula 10]
[13]
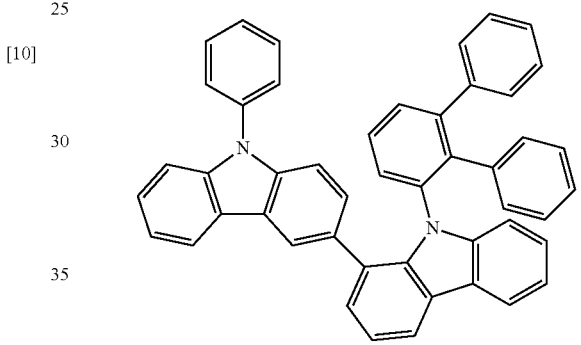
[14]
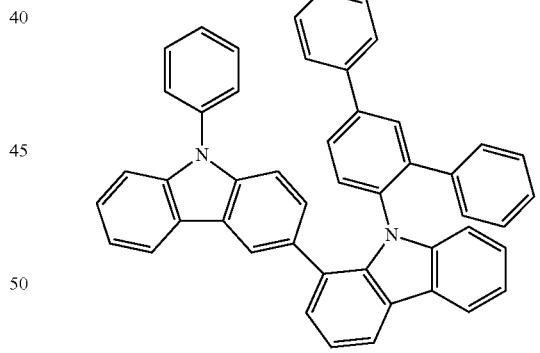
[15]
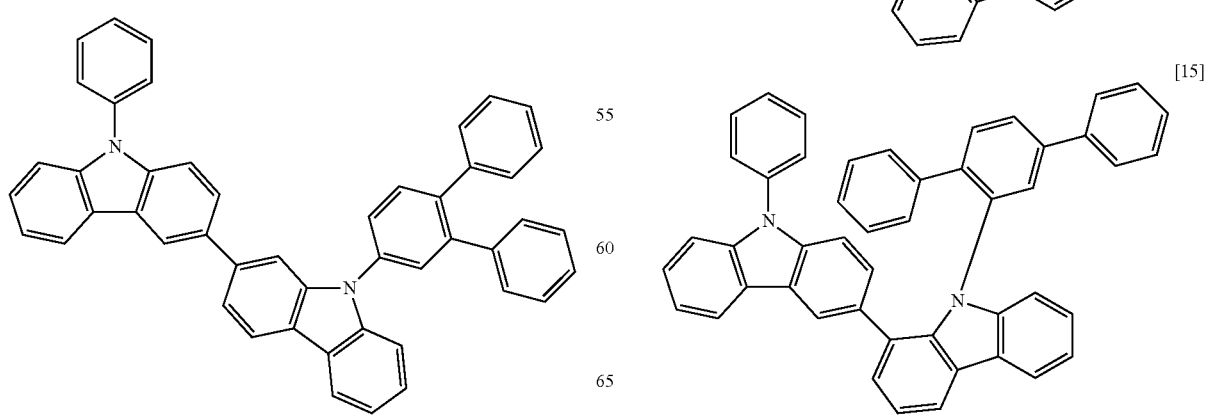

[16]
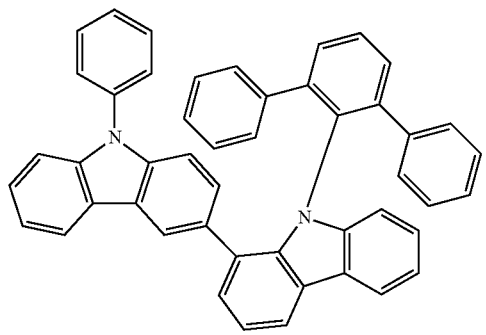
[17]
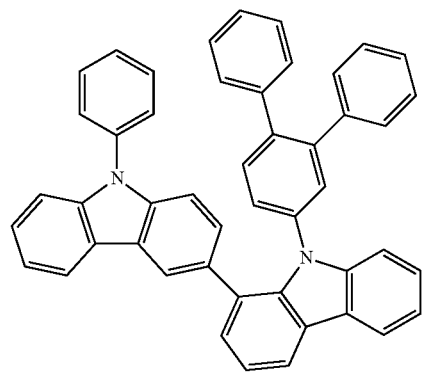
[18]
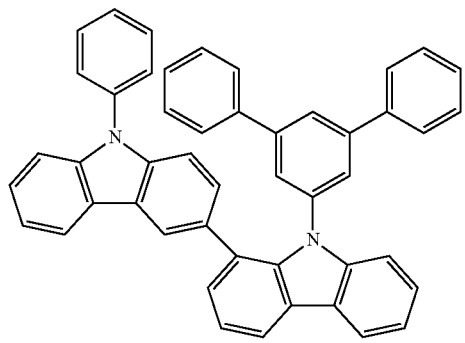
[19]
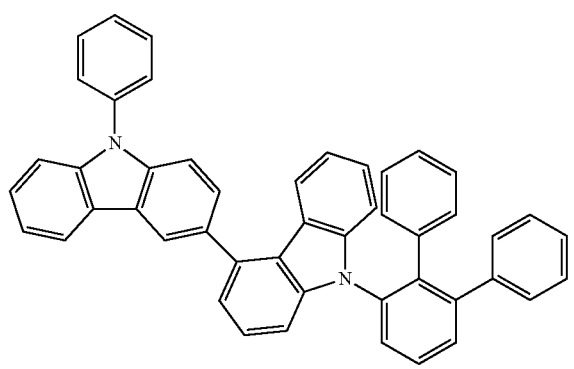
[20]
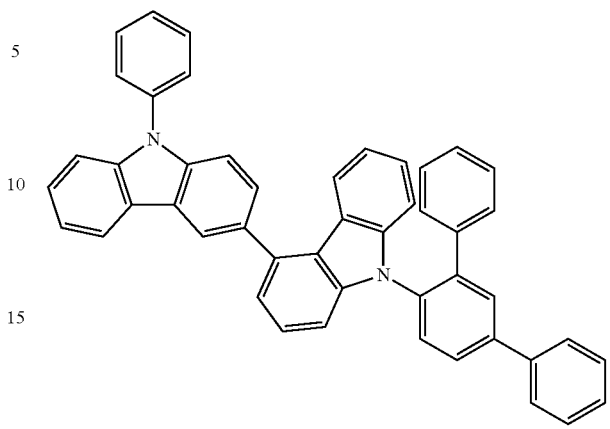
[21]
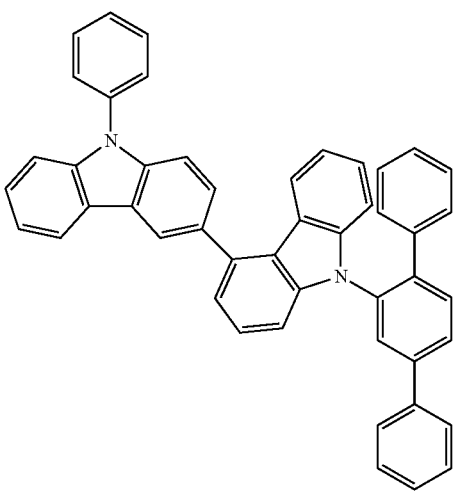
[22]
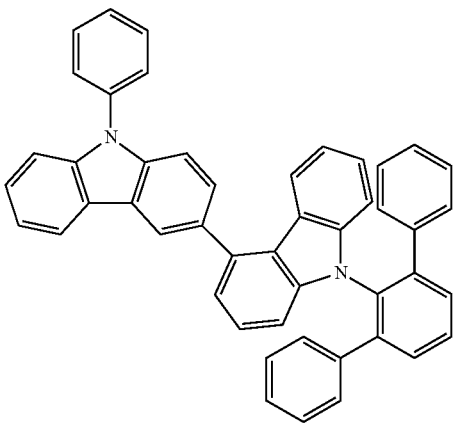

[23]
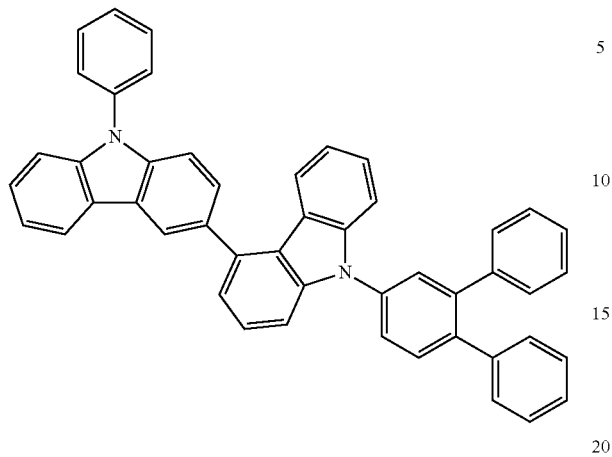
[24]
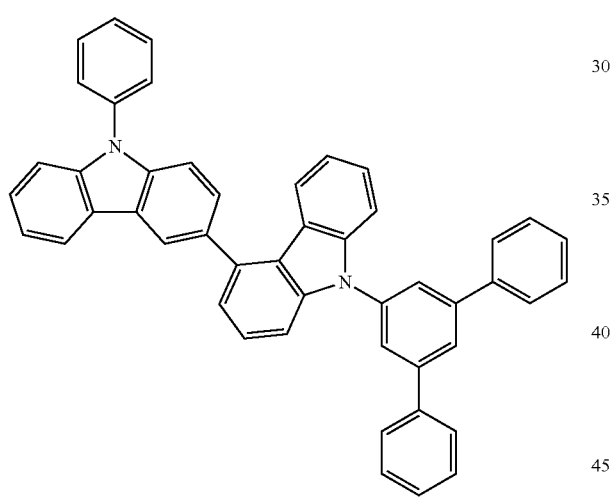
[Chemical Formula 11]
[25]
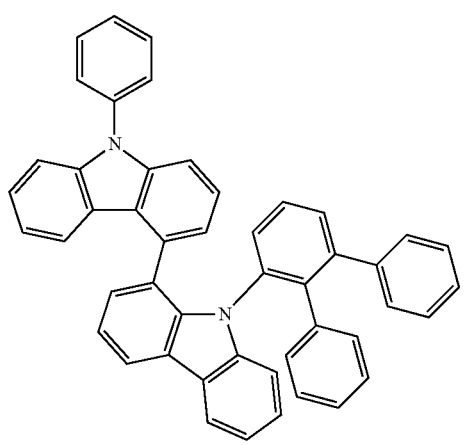
[26]
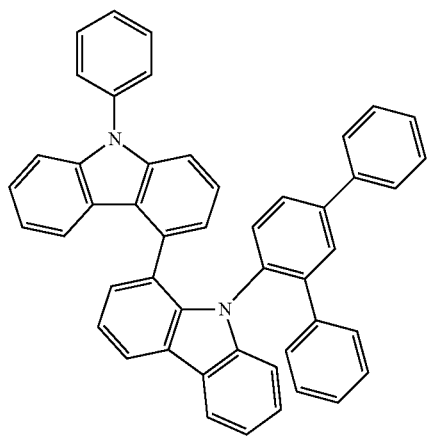
[27]
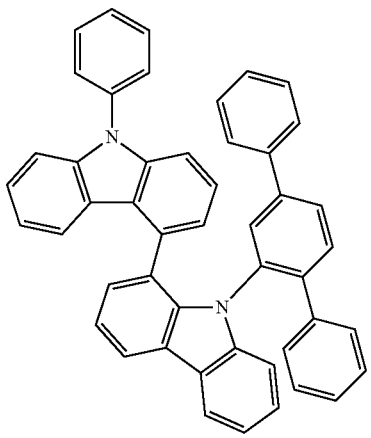
[28]
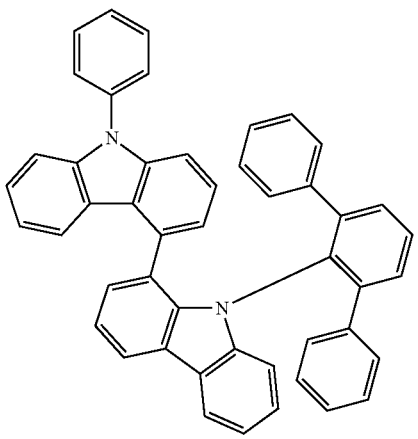

[29]
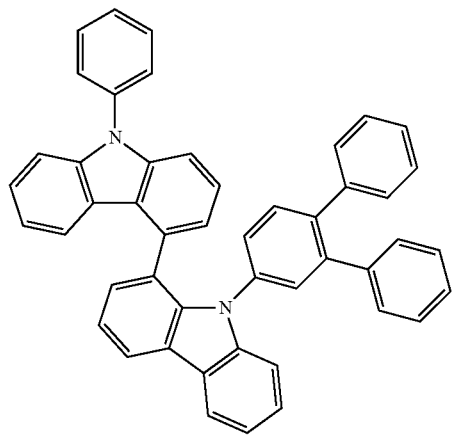
[30]
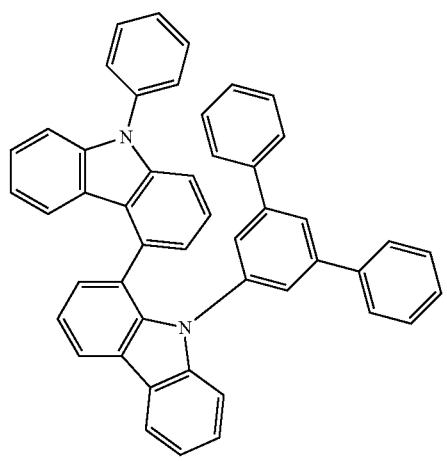
[31]
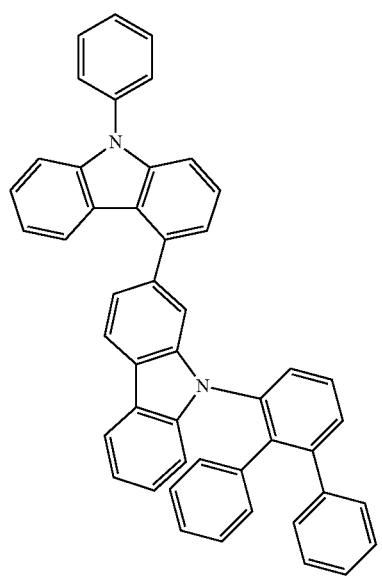
[32]
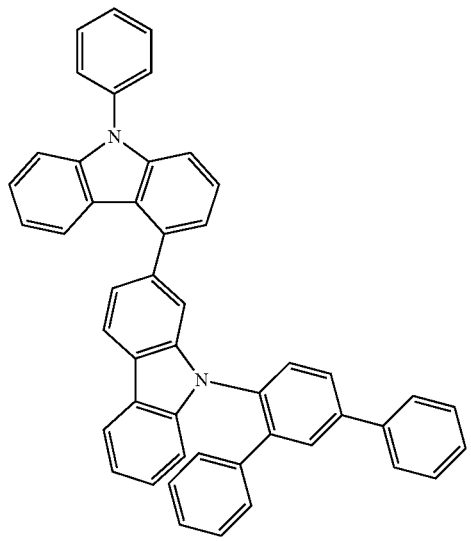
[33]
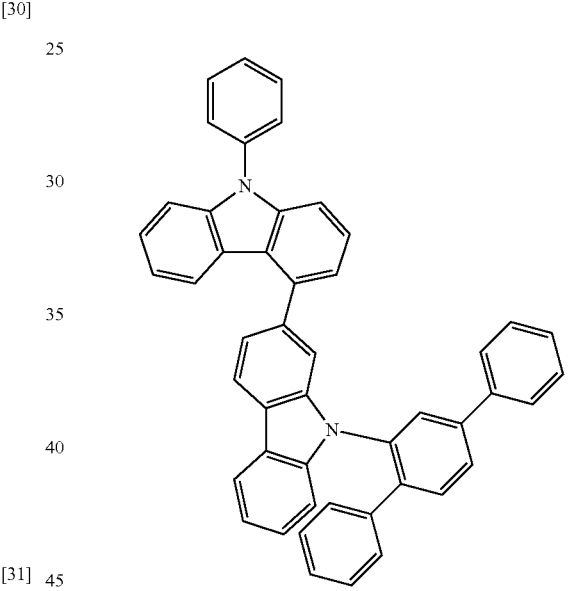
[34]
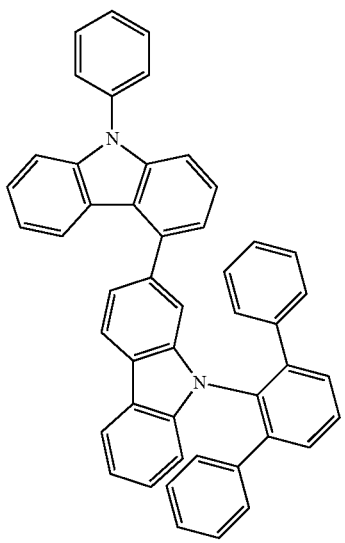

[Chemical Formula 12]
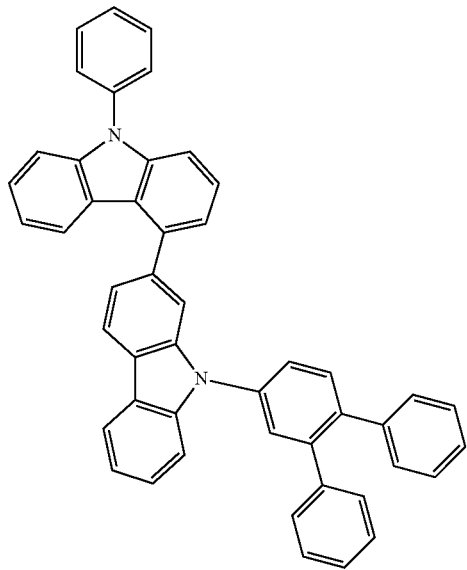
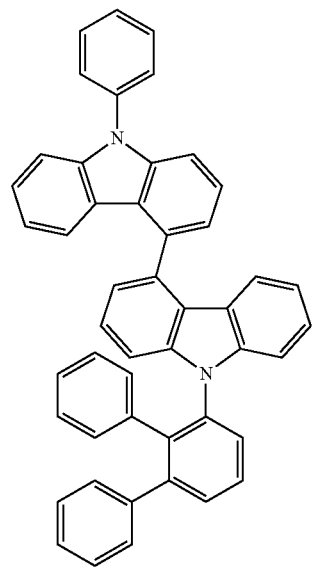
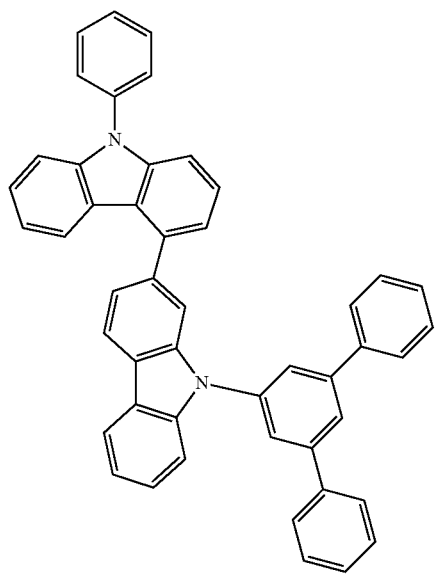
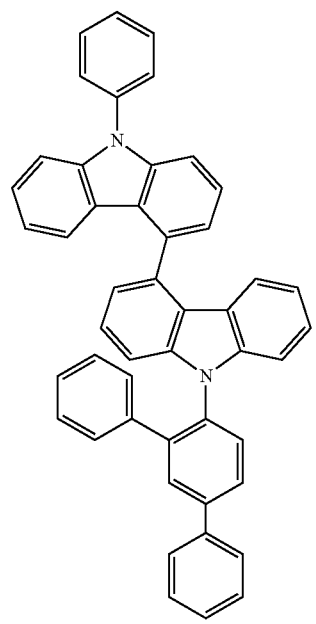

-continued
[39] 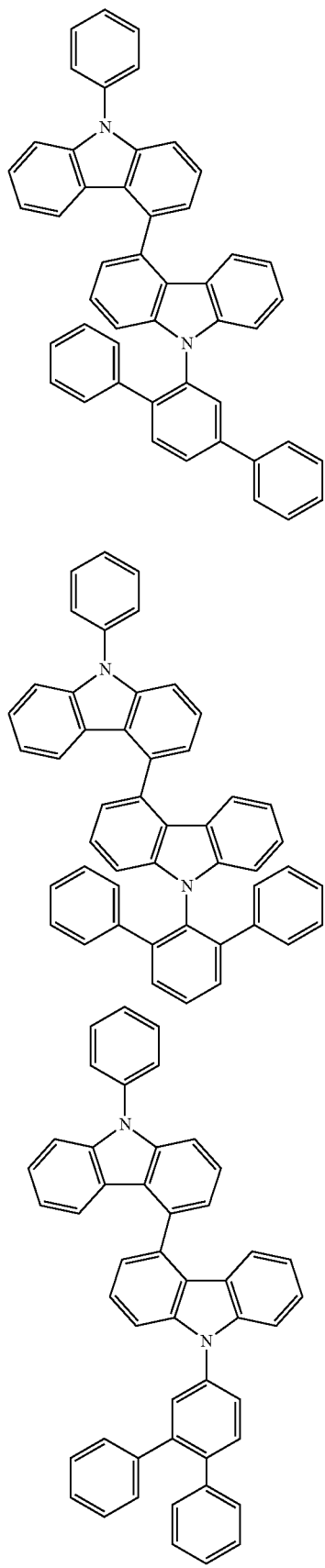
[40] 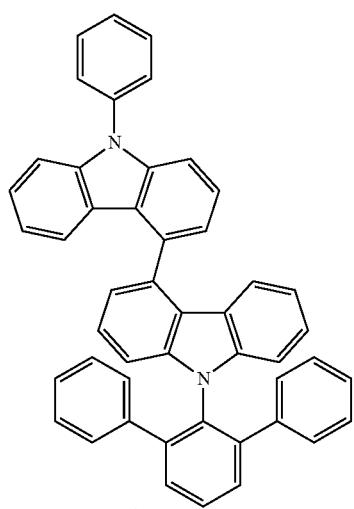
[41] 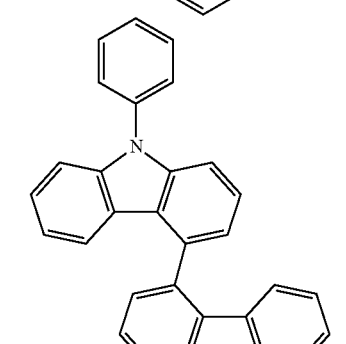
[42] 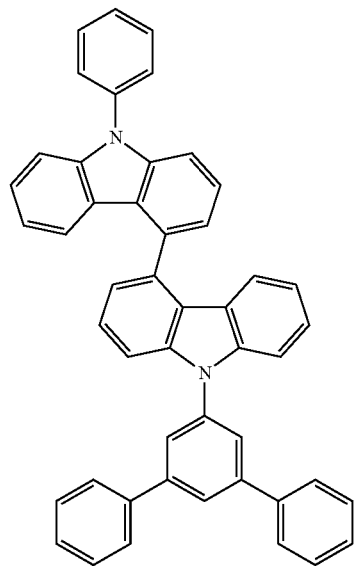
[43] 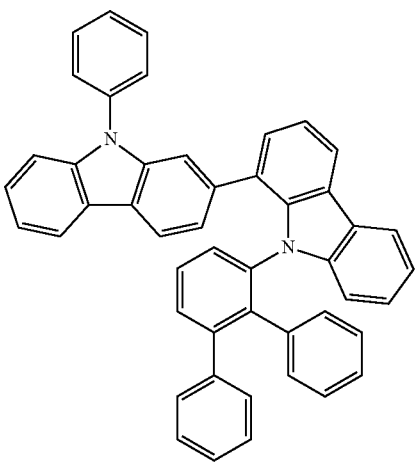
[44] 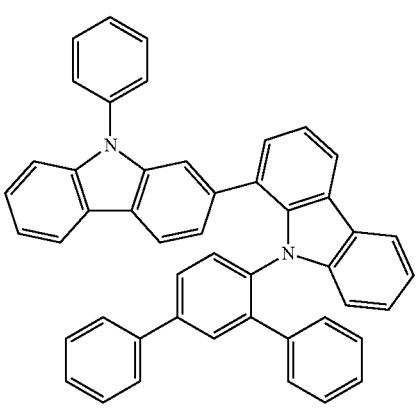

25
-continued
[45]
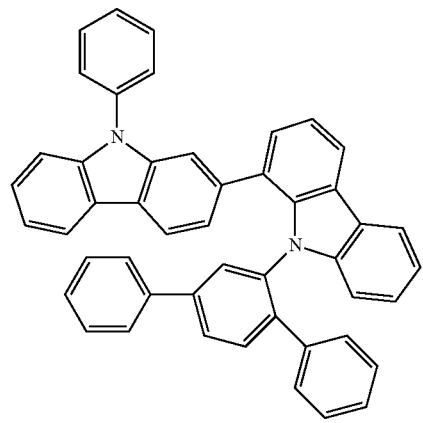
[46]
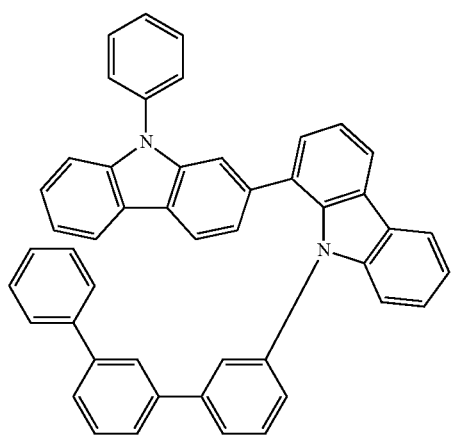
[47]
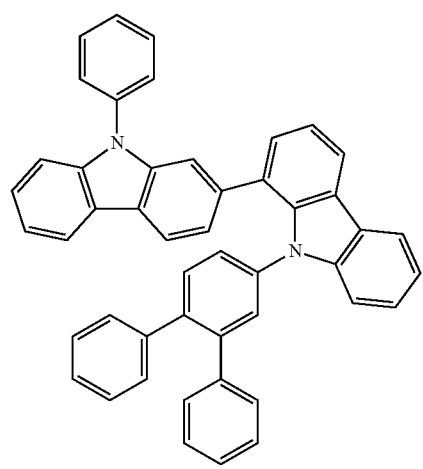
26
-continued
[48]
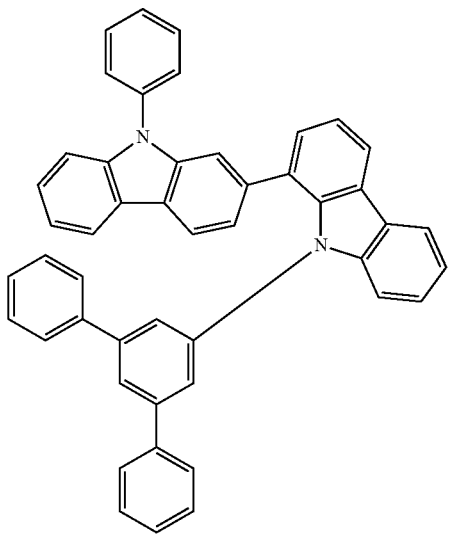
[Chemical Formula 13]
[49]
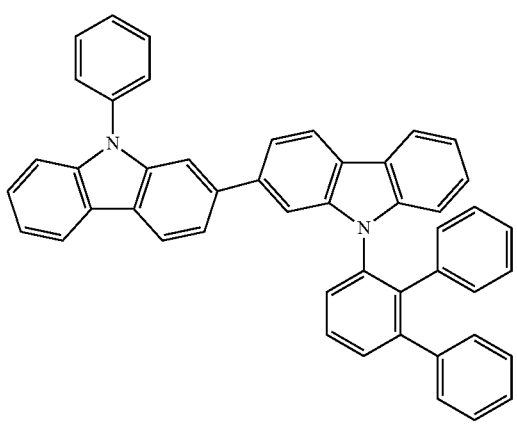
[50]
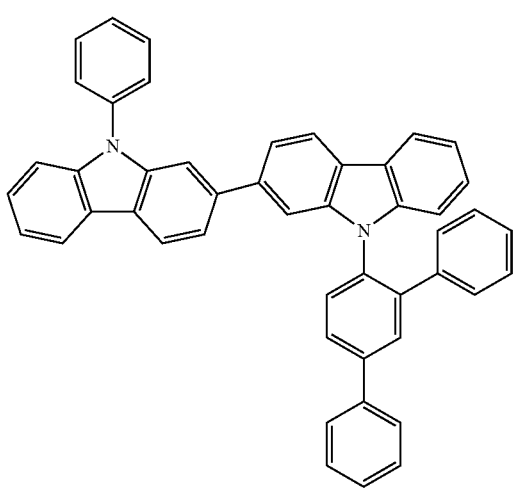

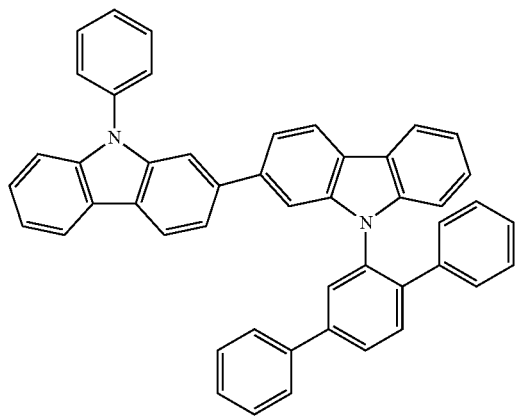
[51]
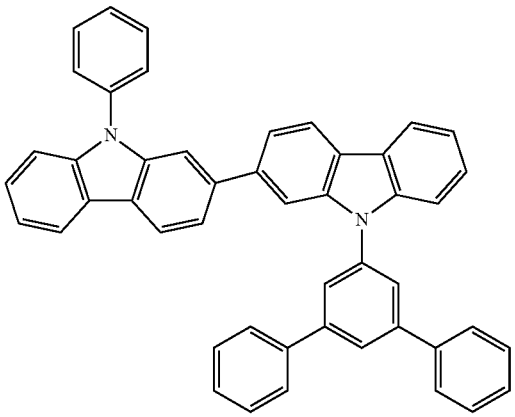
[54]
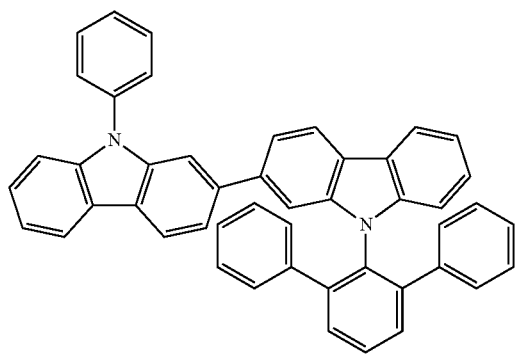
[52]
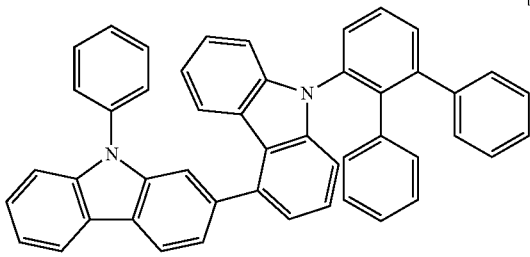
[55]
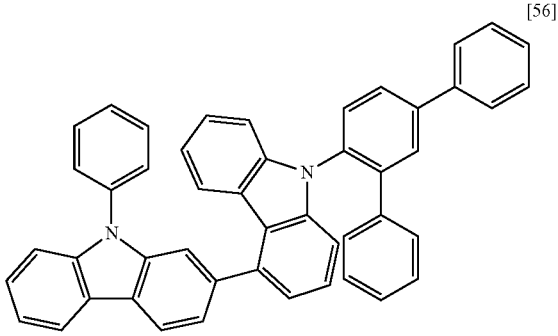
[56]
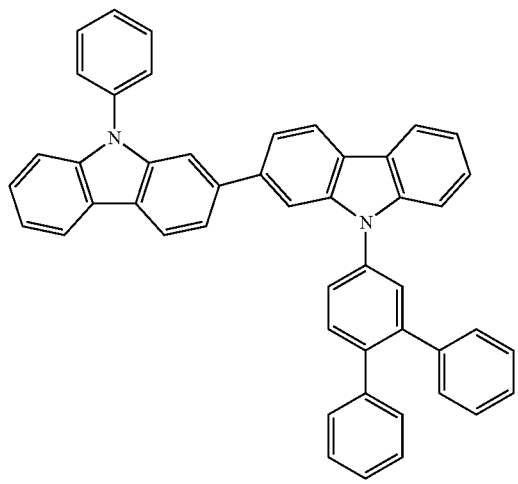
[53]
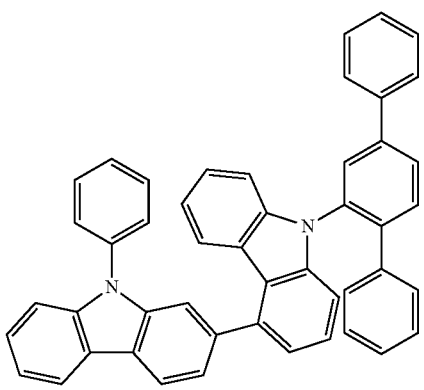
[57]

[58]
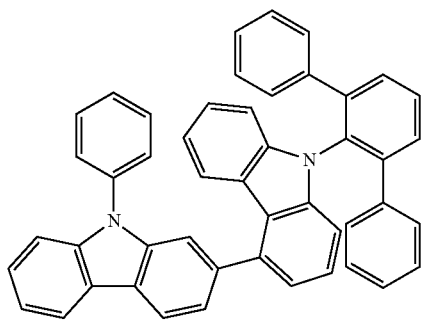
[62]
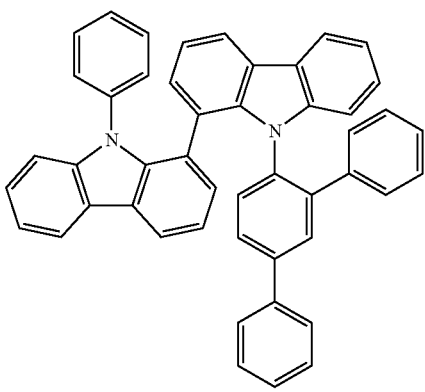
[59]
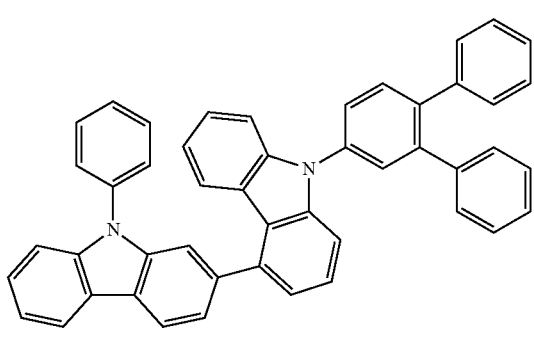
[63]
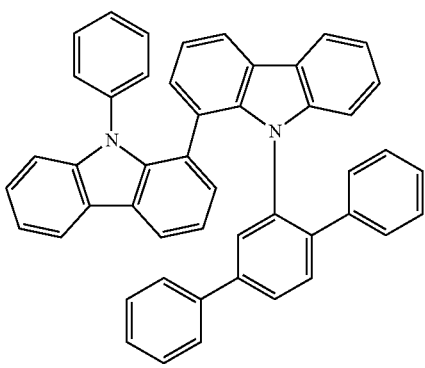
[60]
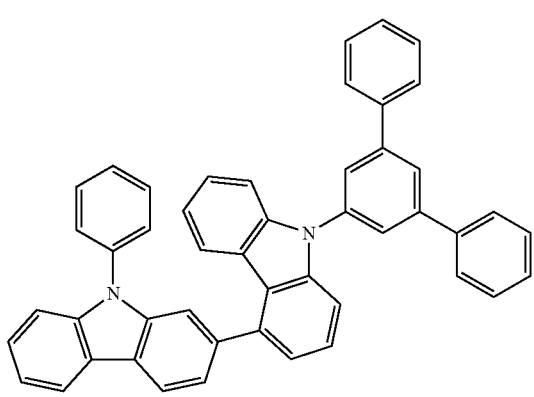
[64]
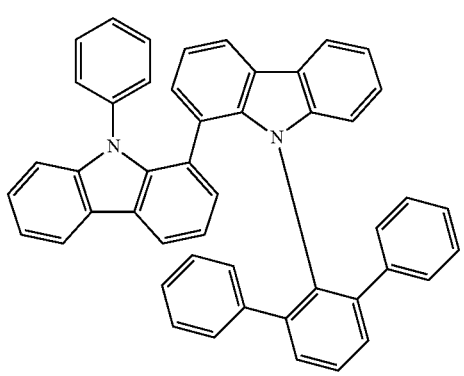
[Chemical Formula 14]
[61]
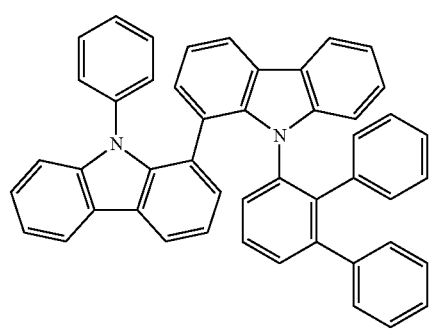
[65]
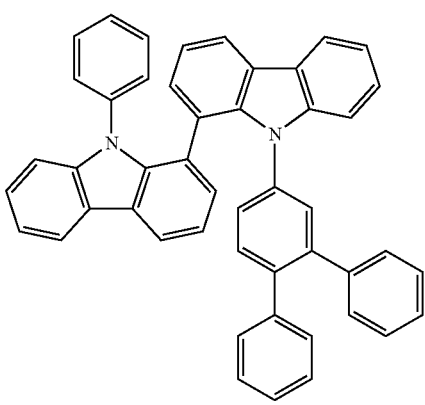

[66]
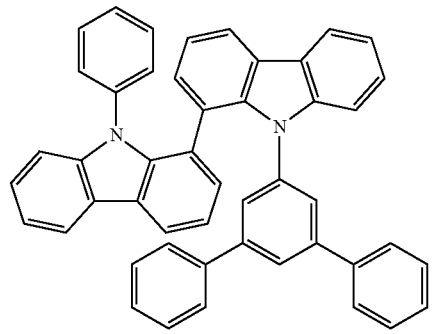
[67]
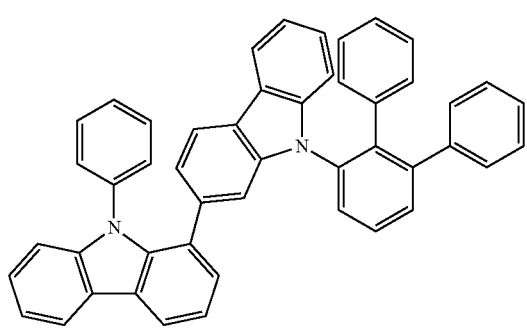
[68]
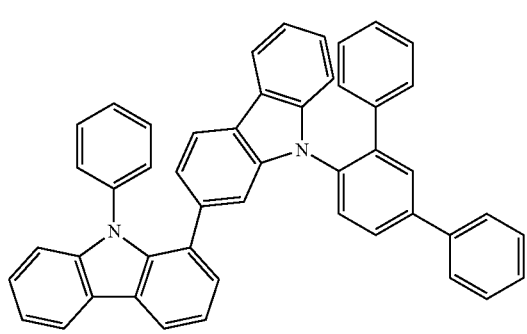
[69]
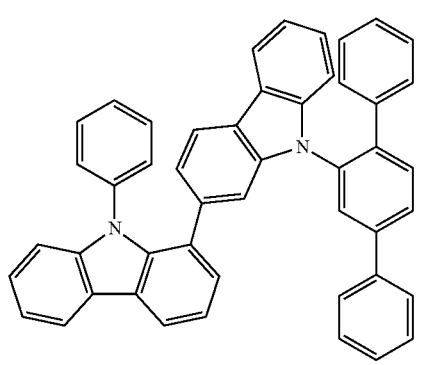
[70]
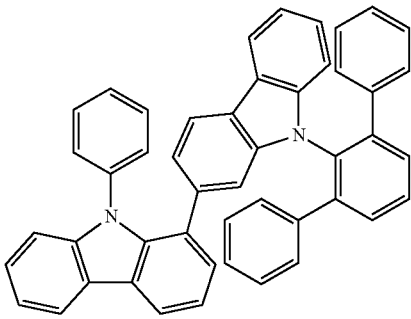
[71]
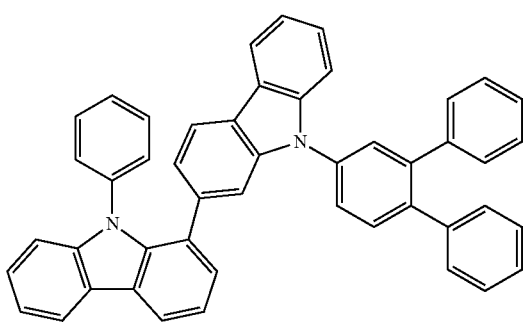
[72]
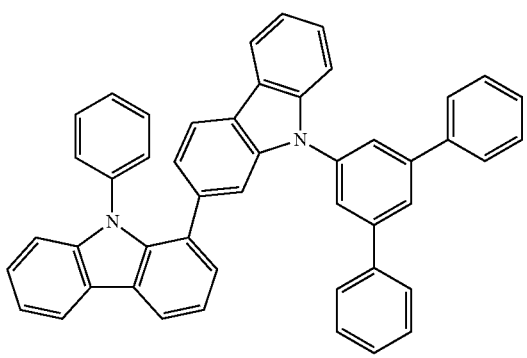
[Chemical Formula 15]
[Chemical Formula 15]
[73]
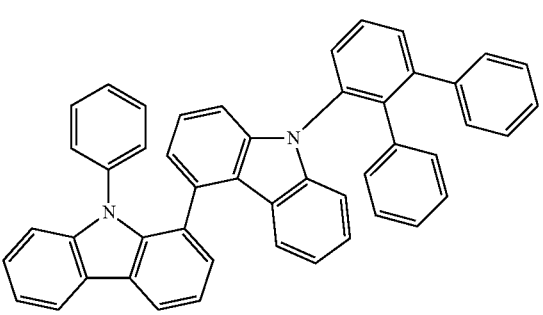

-continued
[74]
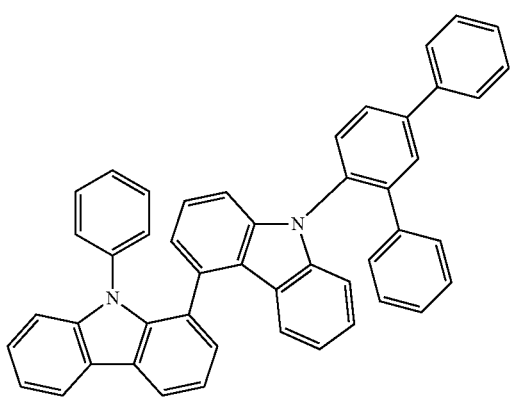
[75]
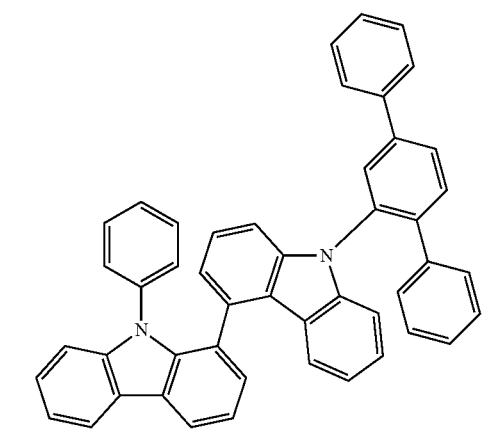
[76]
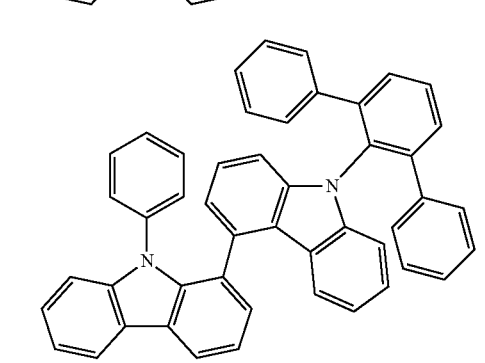
[77]
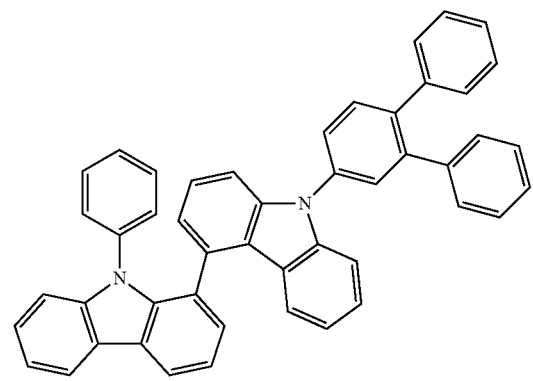
-continued
[78]
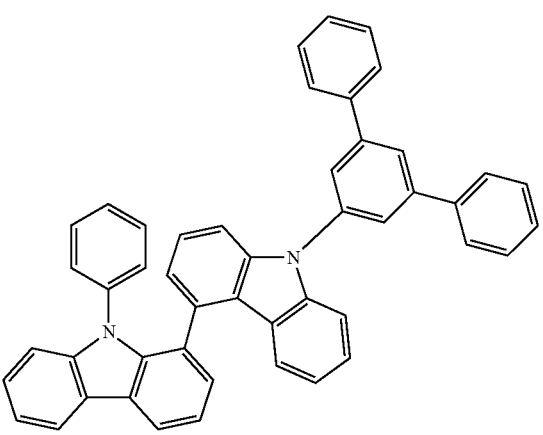
[79]
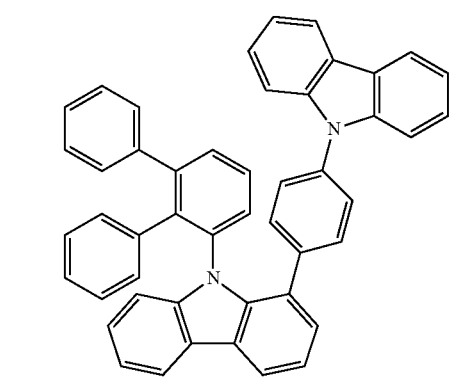
[80]
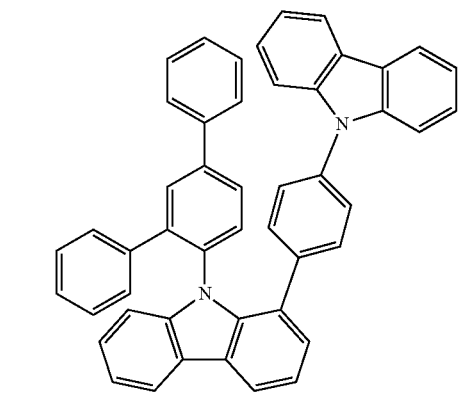
[81]
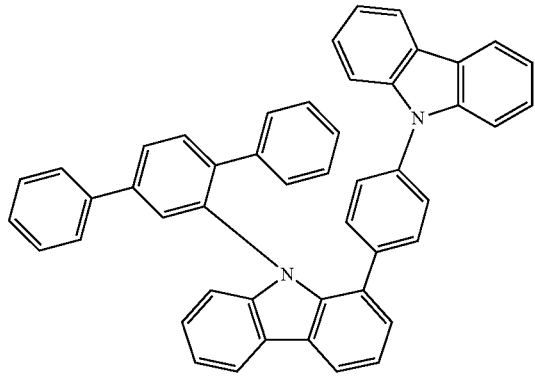

[82]
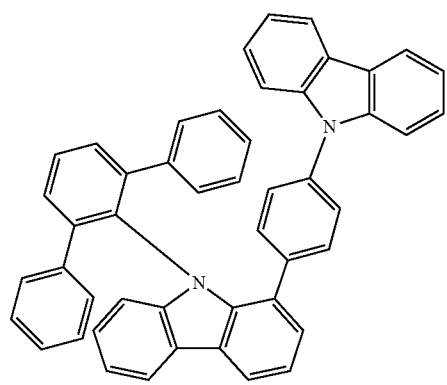
[83]
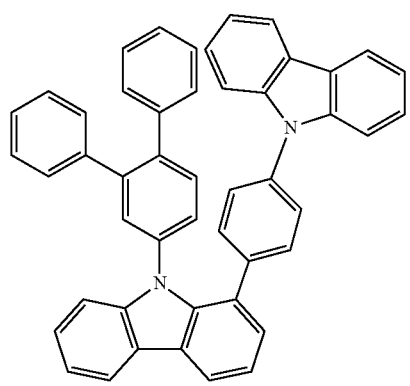
[84]
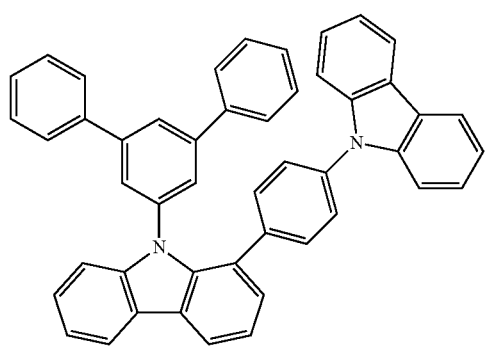
[Chemical Formula 16]
[Chemical Formula 16]
[85]
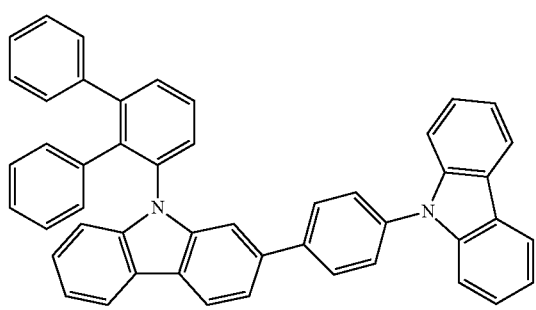
[86]
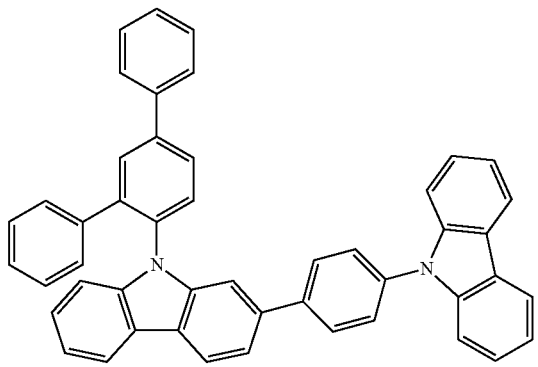
[87]
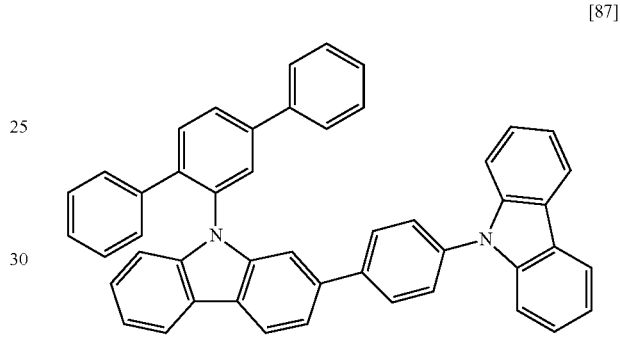
[88]
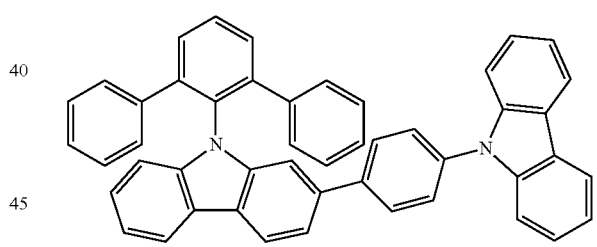
[89]
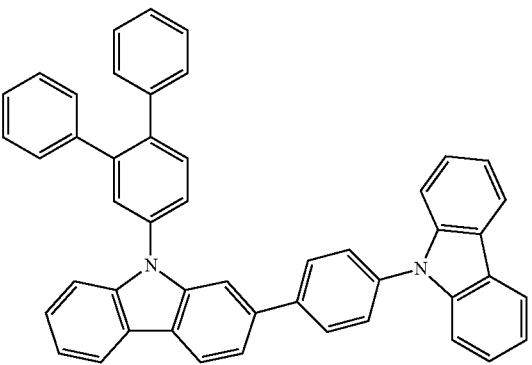

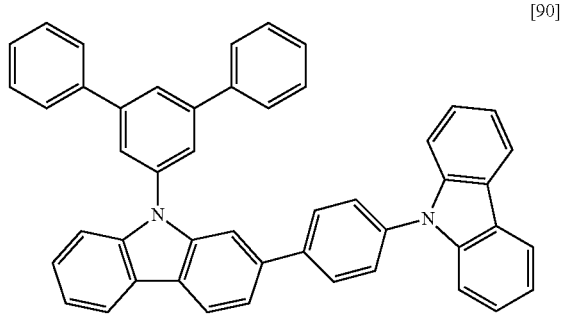
[90]
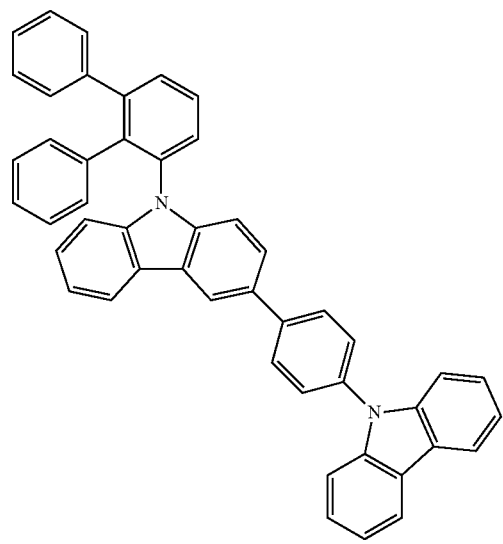
[91]
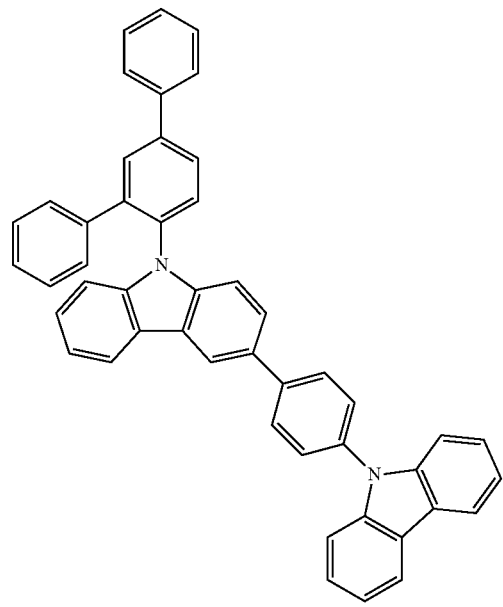
[92]
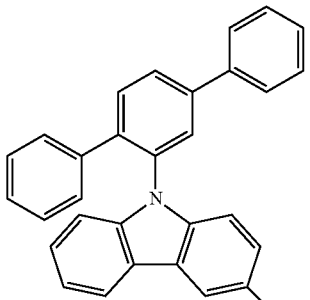
[93]
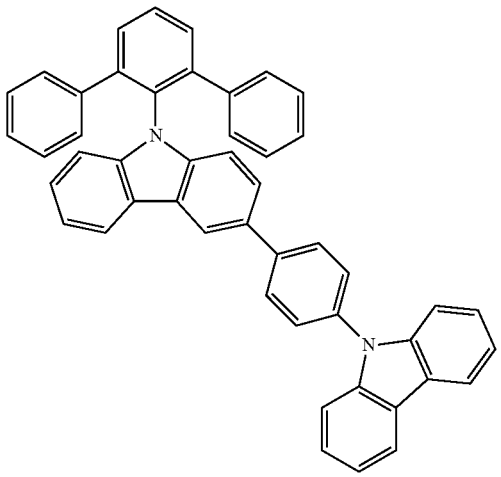
[94]
[95]

[96]
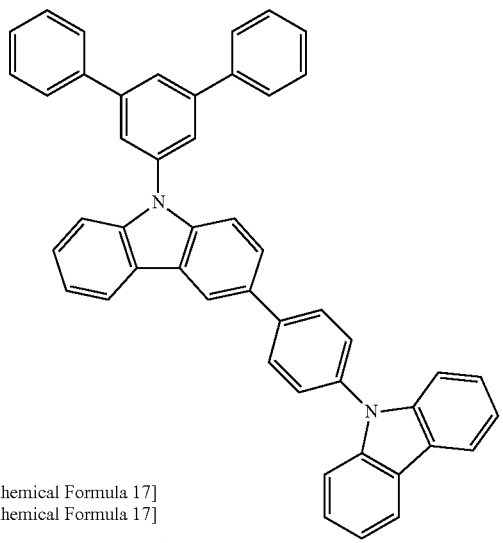
[Chemical Formula 17]
[Chemical Formula 17]
[97]
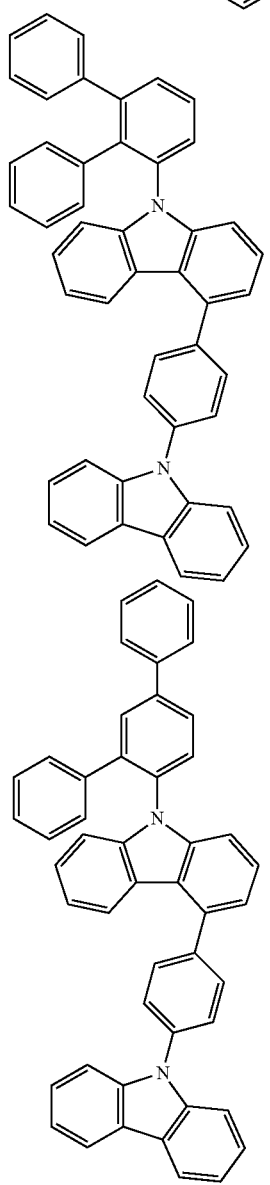
[98]
[99]
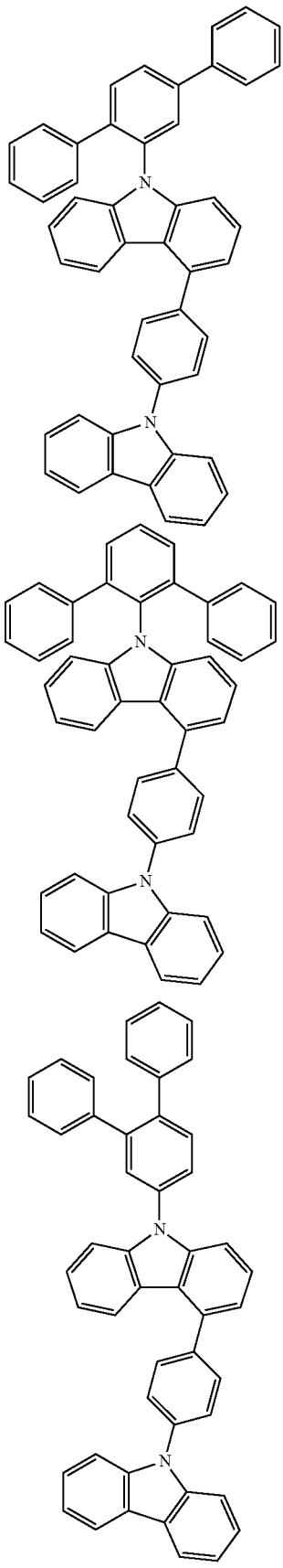
[100]
[101]

[102]
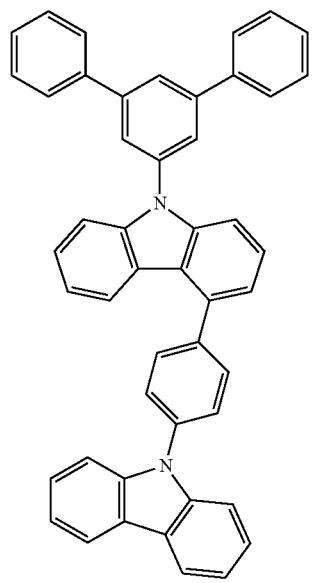
[103]
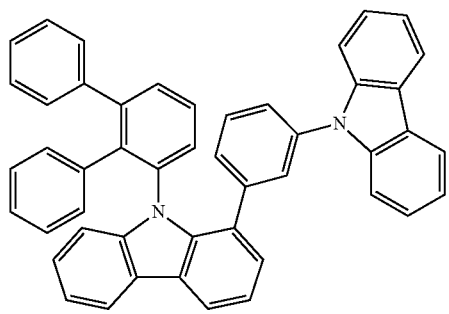
[104]
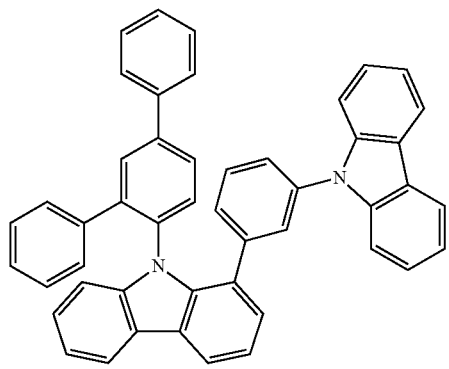
[105]
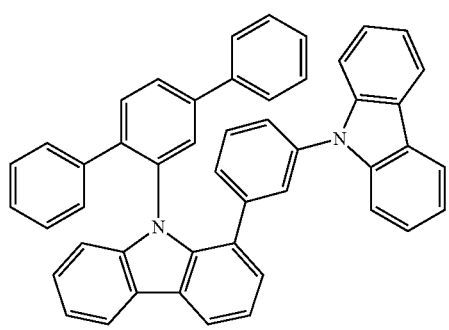
[106]
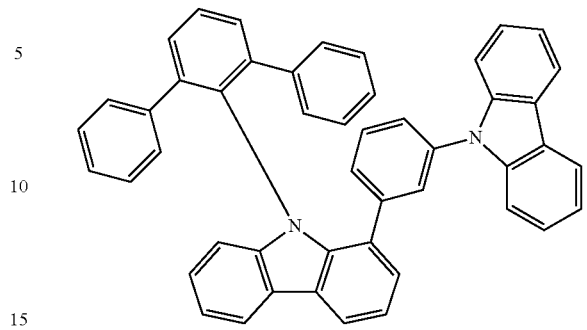
[107]
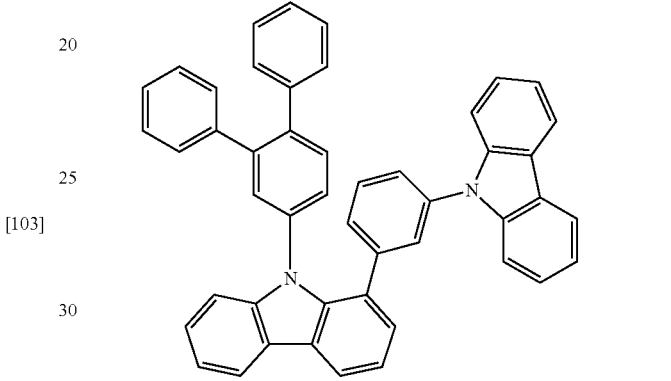
[108]
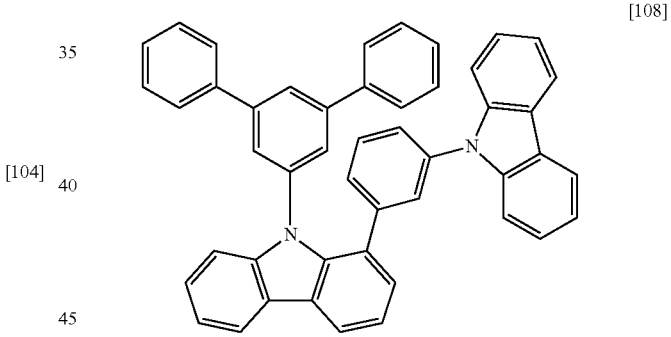
[Chemical Formula 18]
[Chemical Formula 18]
[109]
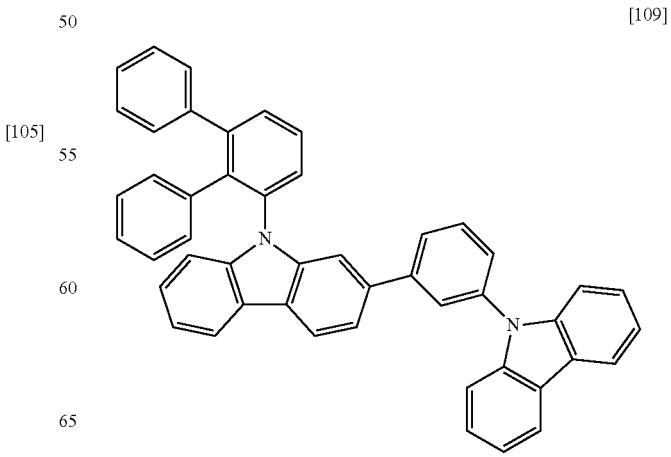

[110]
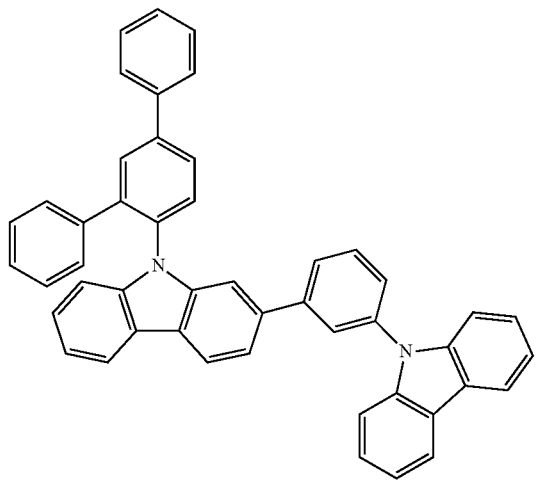
[111]
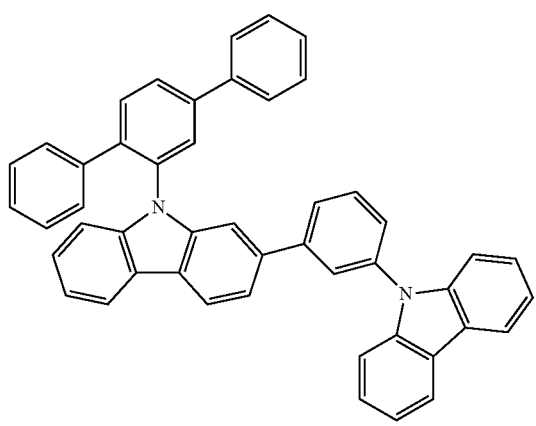
[112]
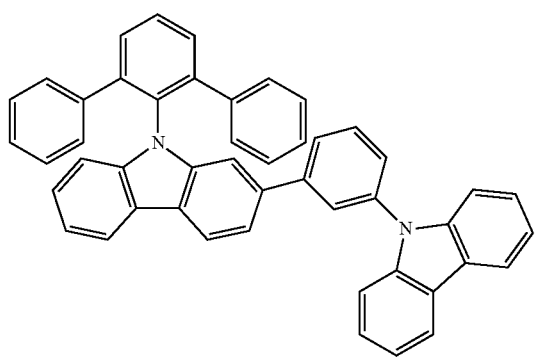
[113]
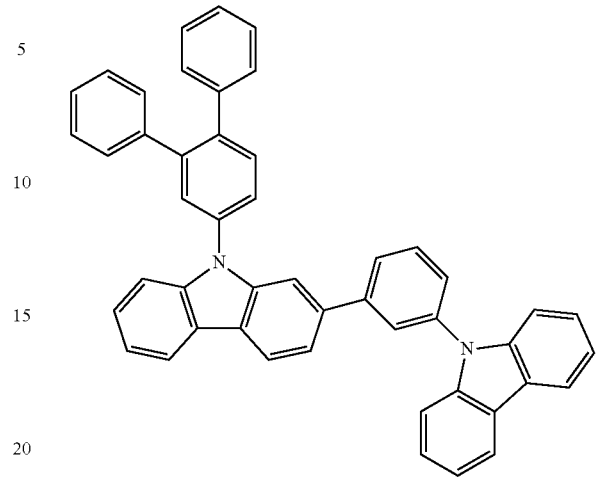
[114]
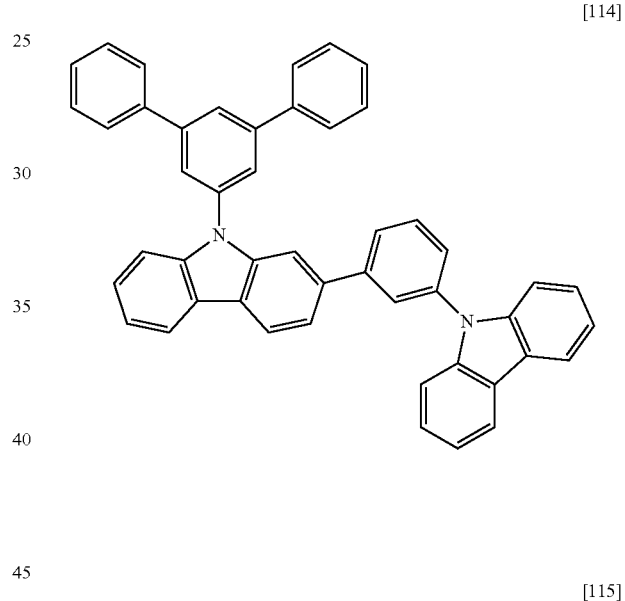
[115]
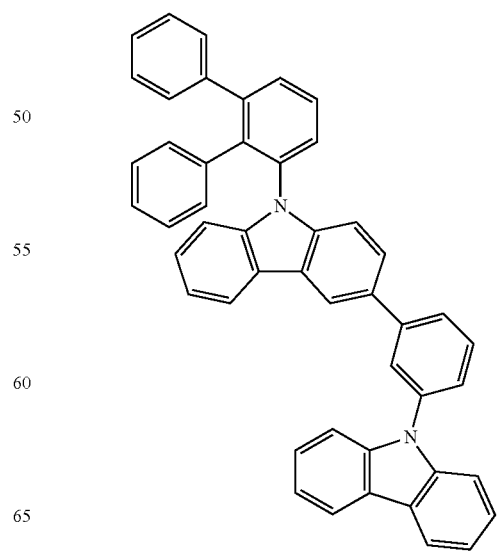

[116]
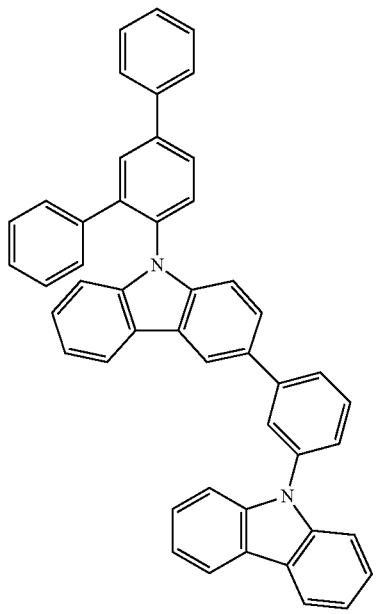
[117]
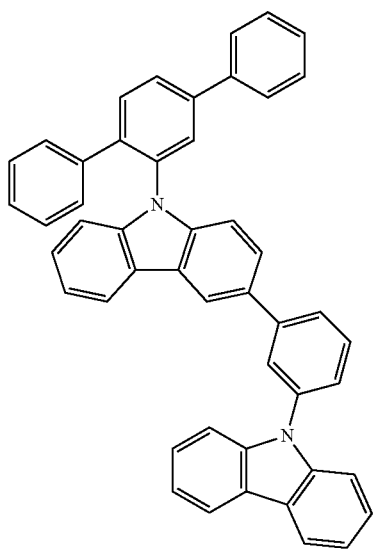
[118]
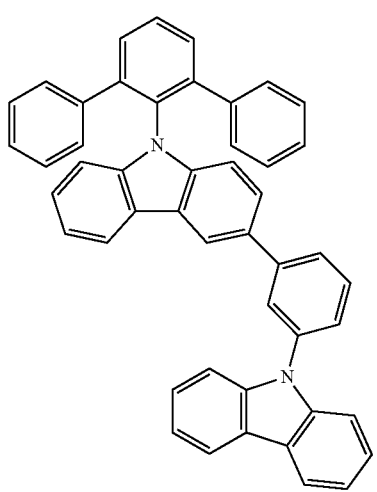
[119]
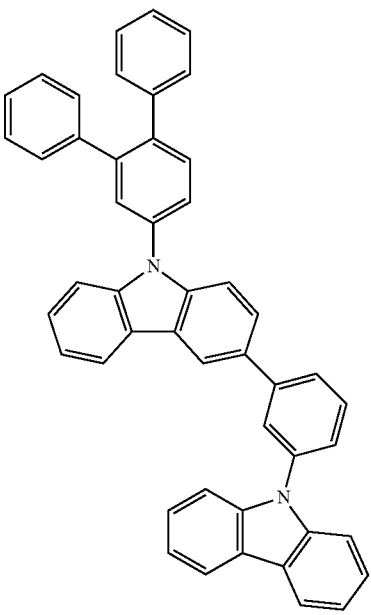
[120]
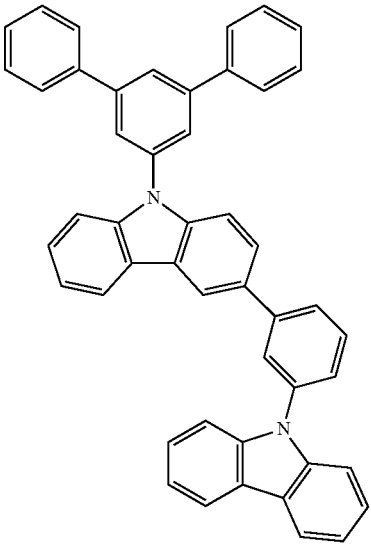
[Chemical Formula 19]
[121]
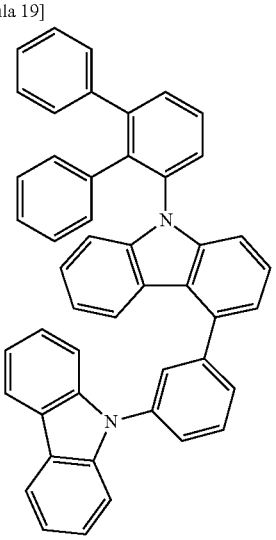

[122]
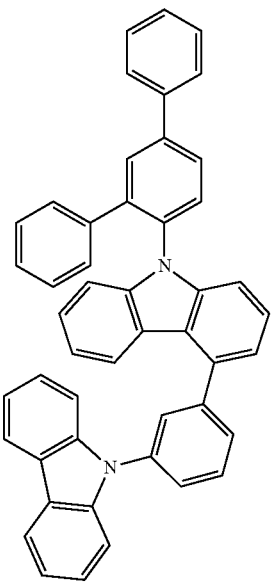
[123]
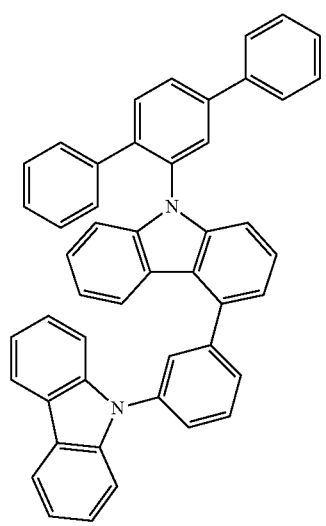
[124]
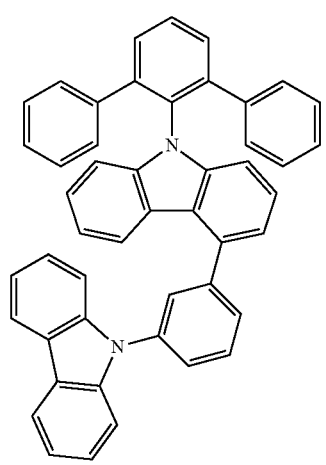
[125]
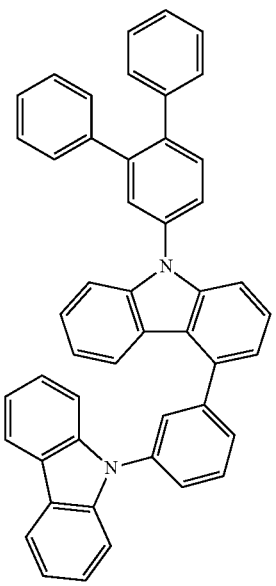
[126]
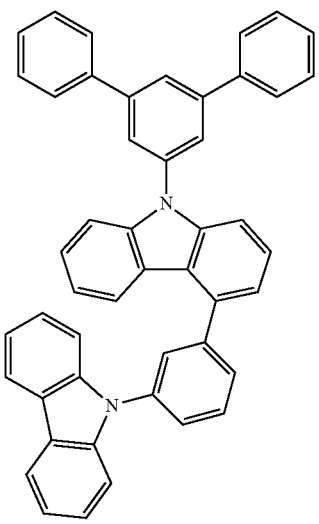
[127]
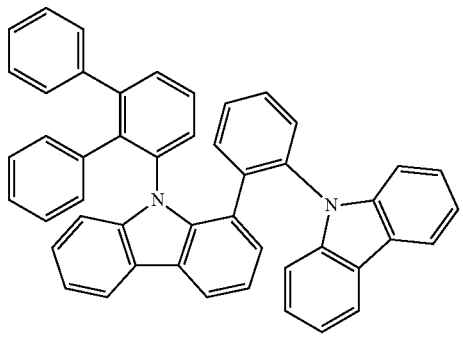

[128]
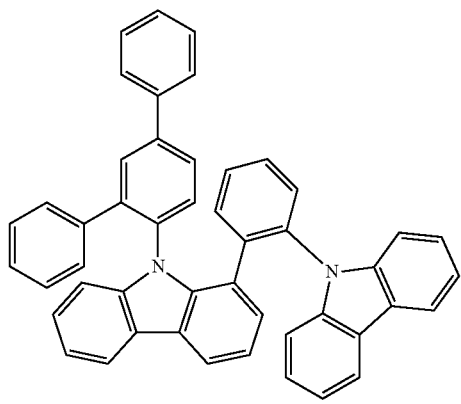
[129]
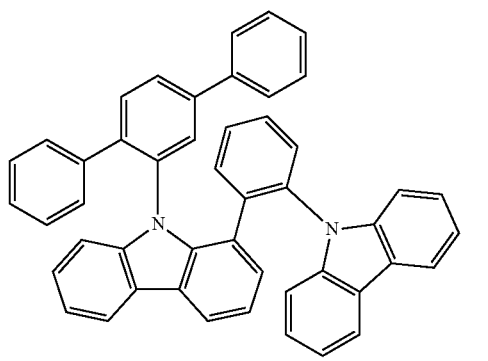
[130]
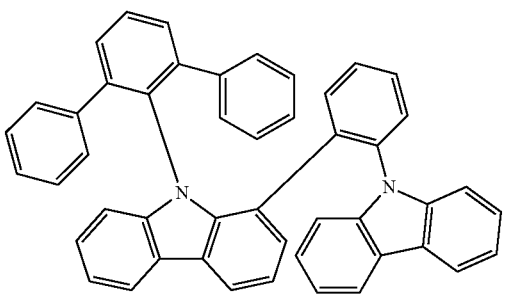
[131]
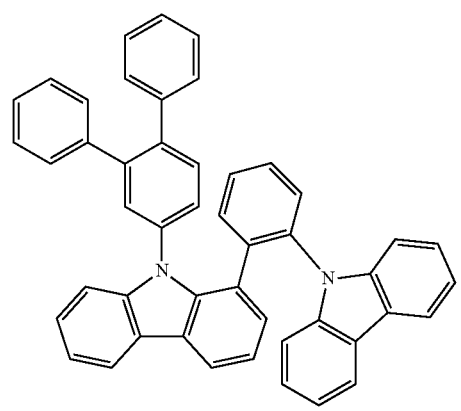
[Chemical Formula 20]
[Chemical Formula 20]
[132]
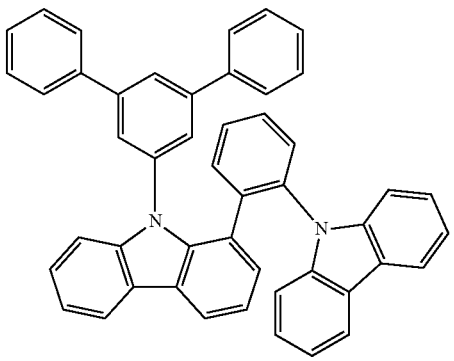
[133]
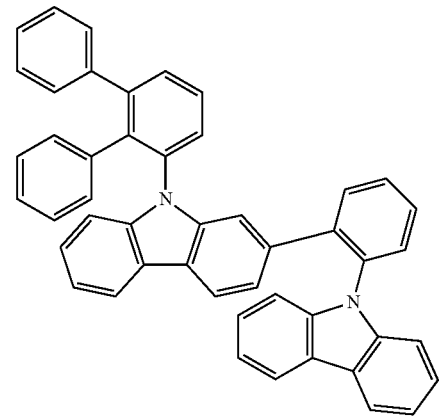
[134]
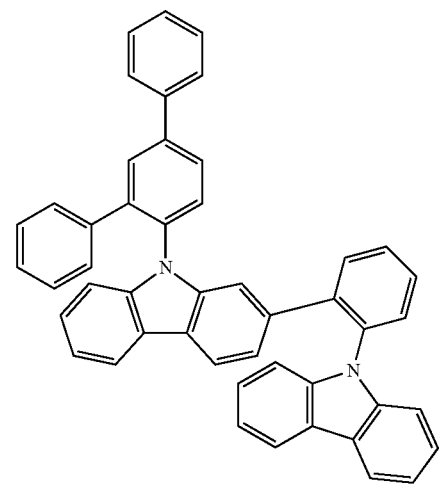

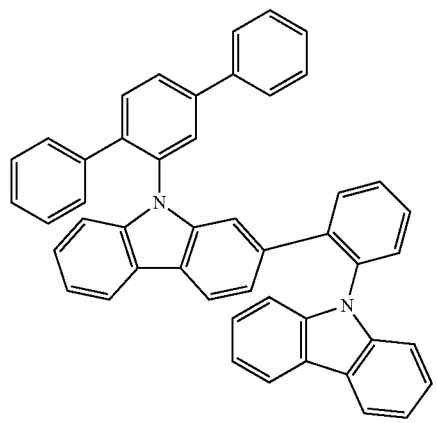
[135]
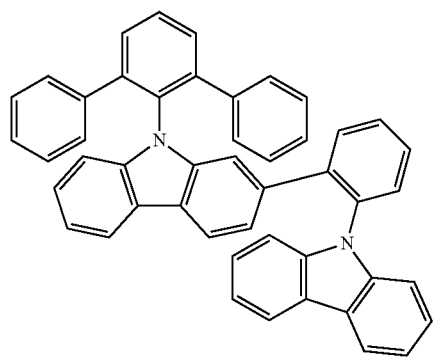
[136]
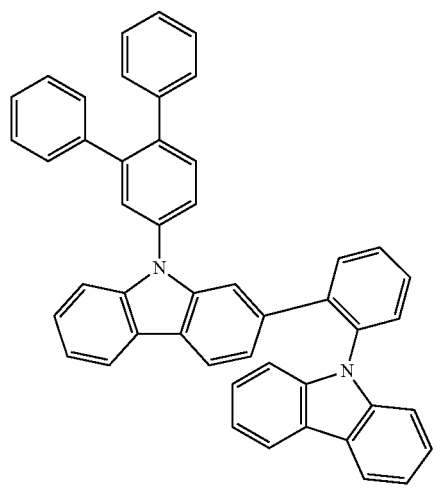
[137]
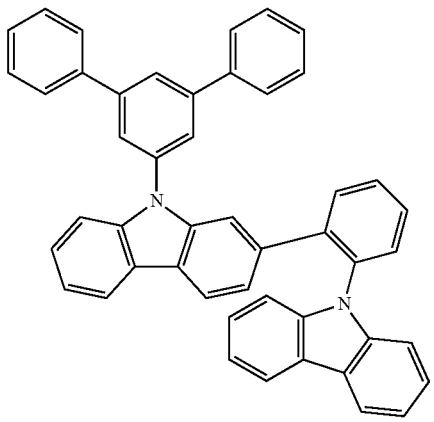
[138]
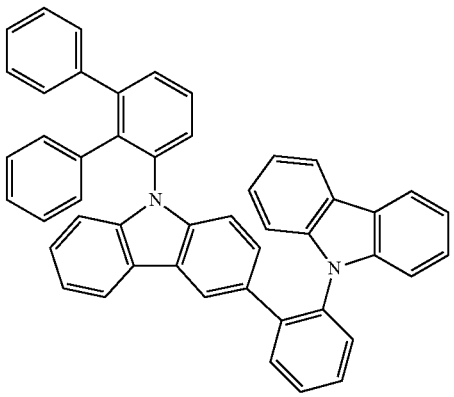
[139]
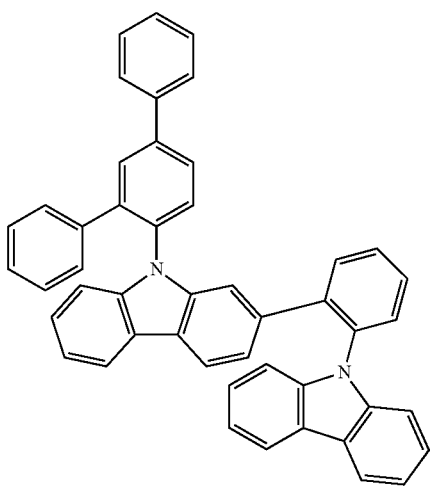
[140]

[141]
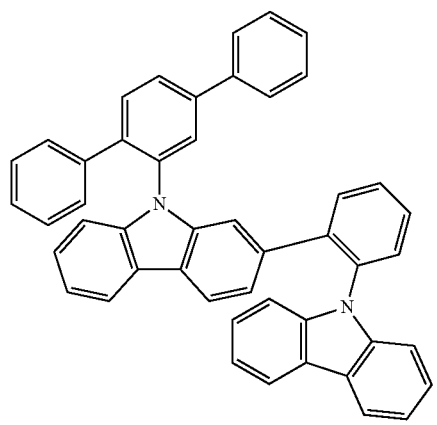
[142]
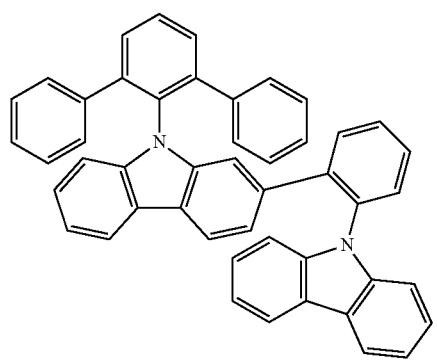
[143]
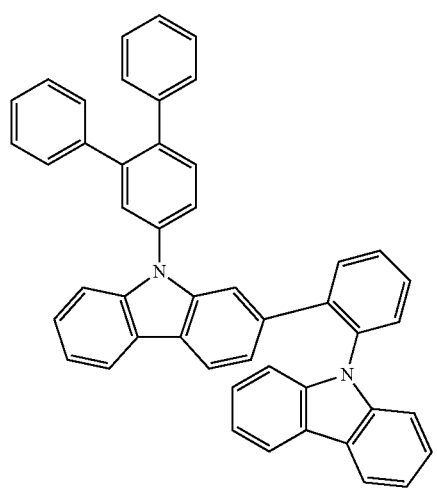
[144]
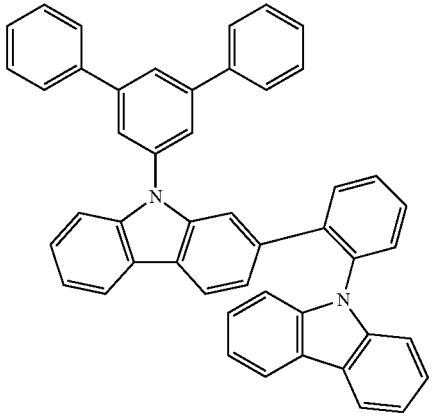
[Chemical Formula 21]
[Chemical Formula 21]
[145]
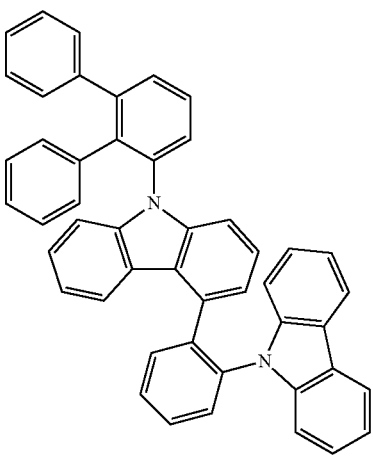
[146]
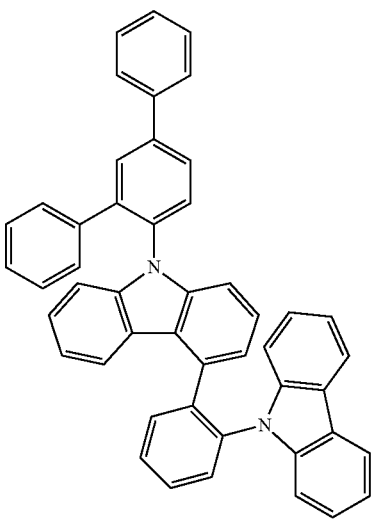

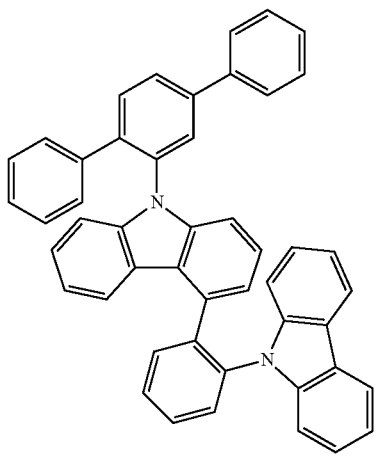
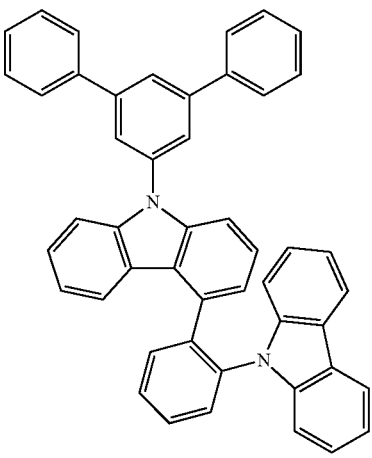
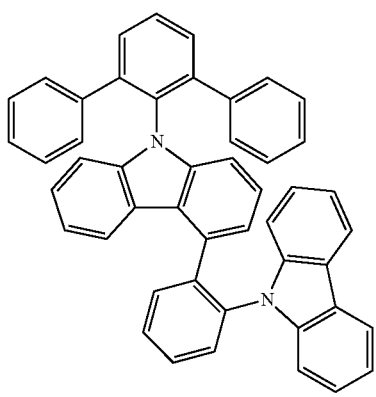
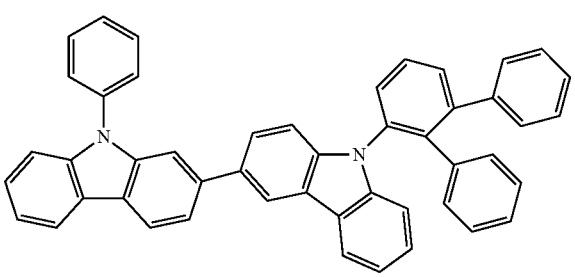
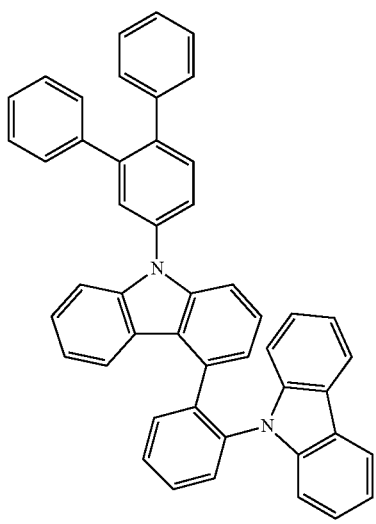
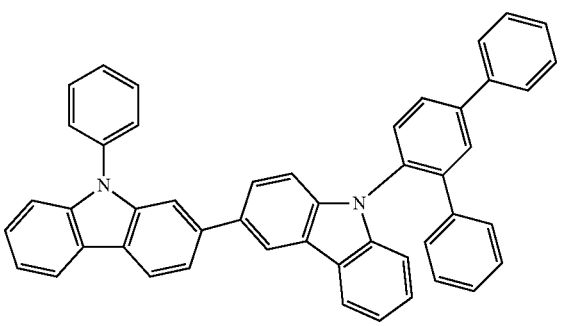
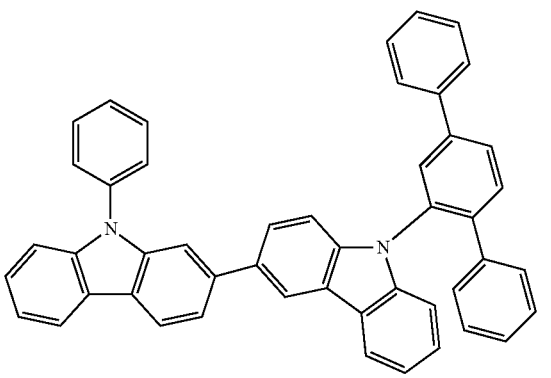

[Chemical Formula 22]
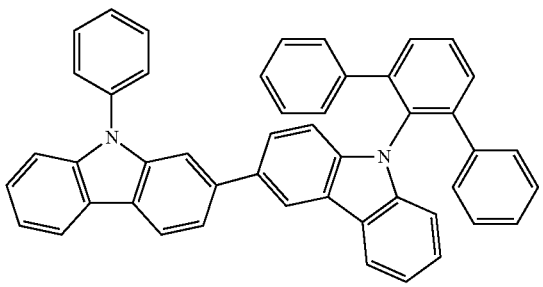
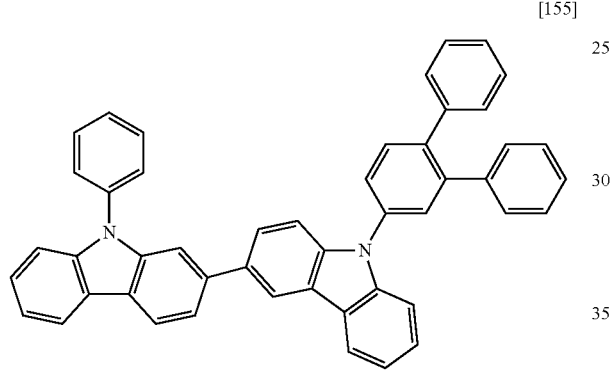
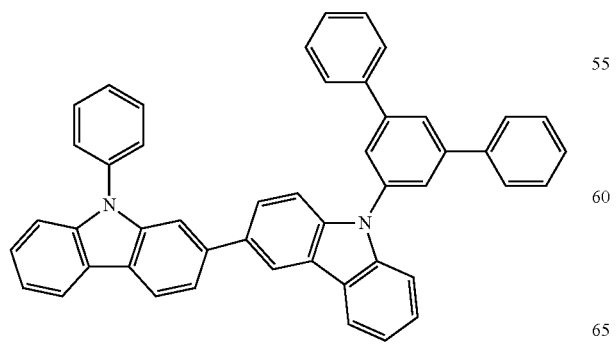
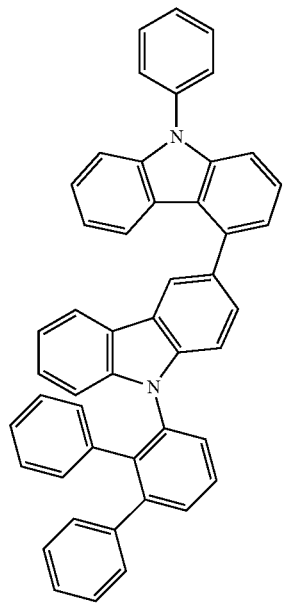
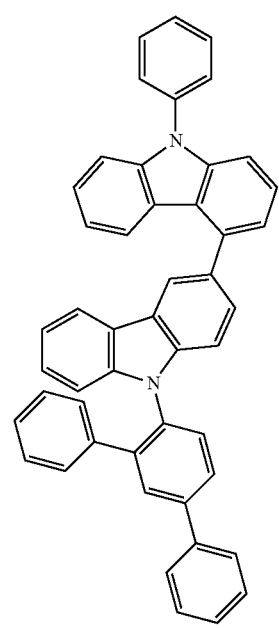

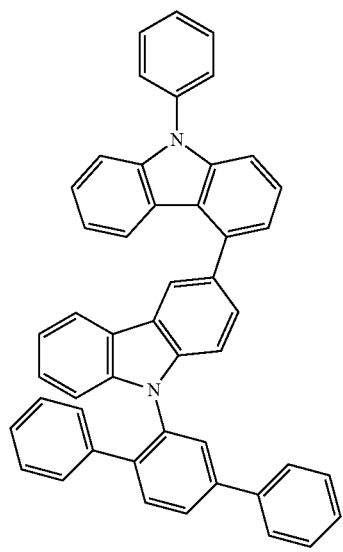
[159]
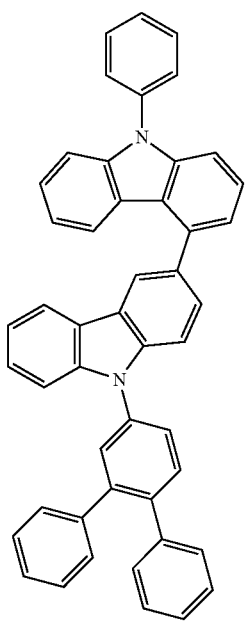
[161]
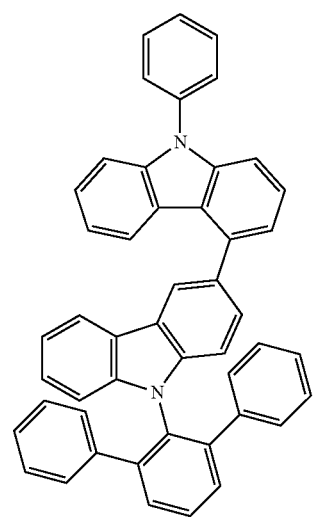
[160]
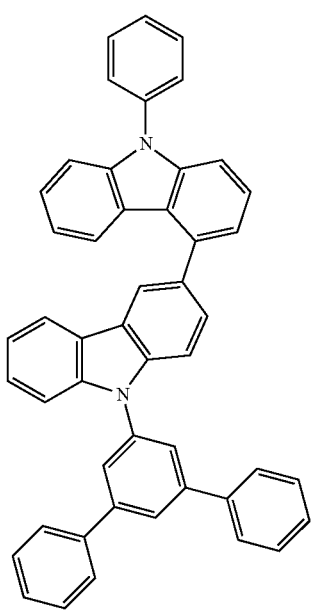
[162]

-continued
[163]
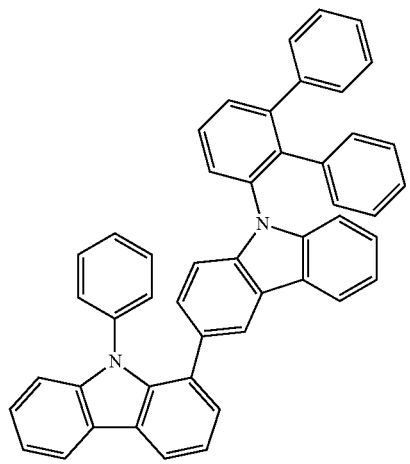
[164]
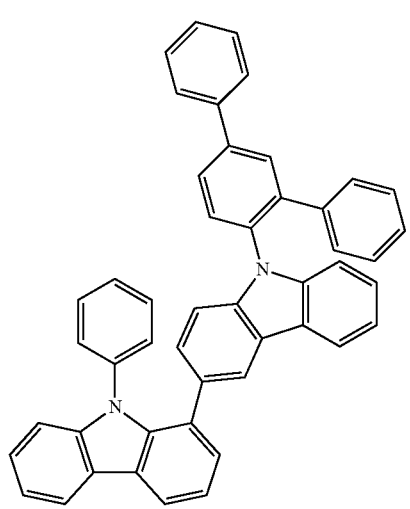
[165]
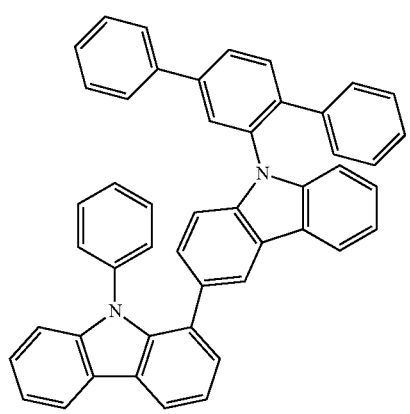
[166]
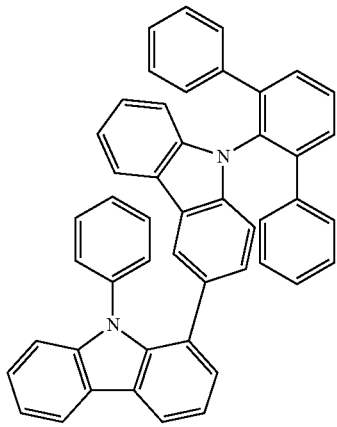
[167]
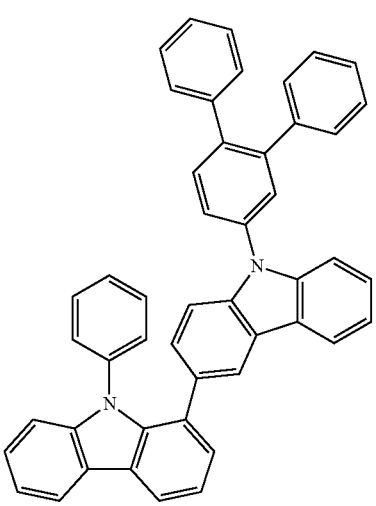
[168]
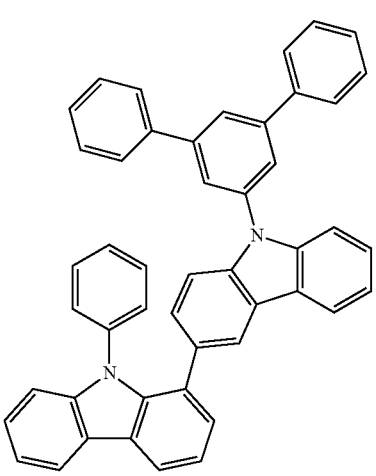

[Chemical Formula 23]
[169]
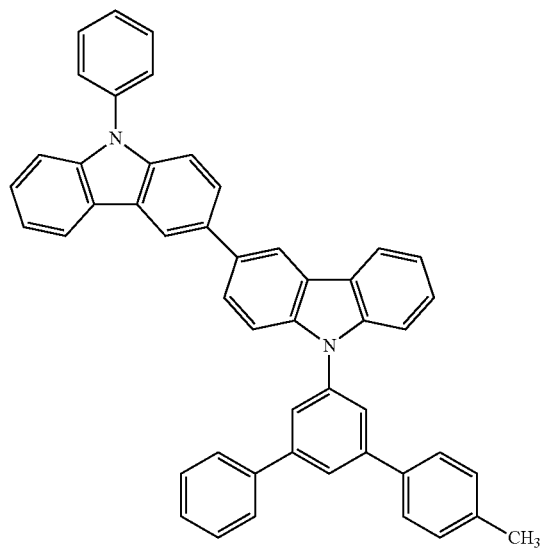
[170]
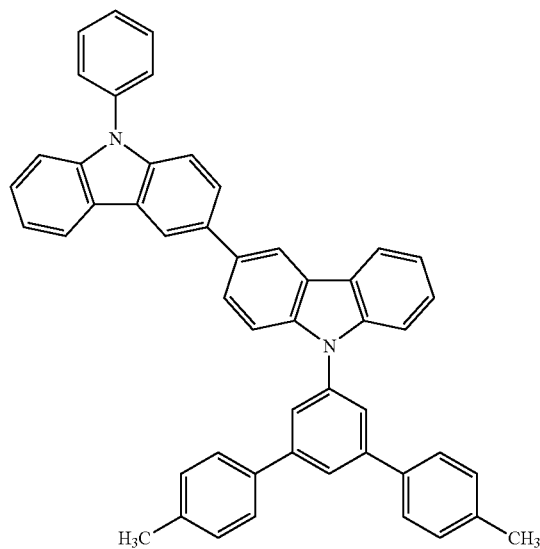
[171]
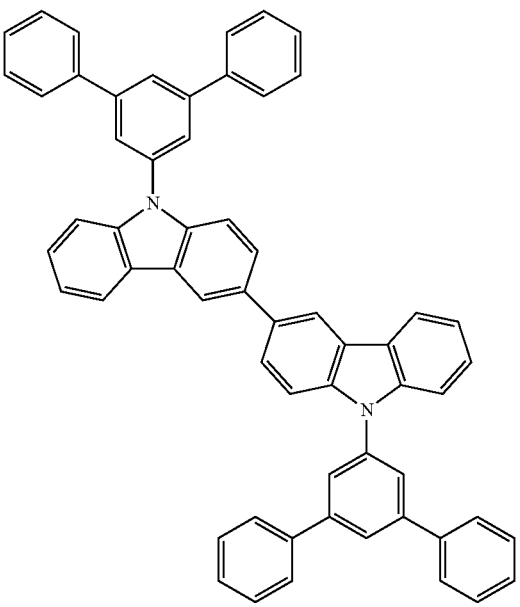
[172]
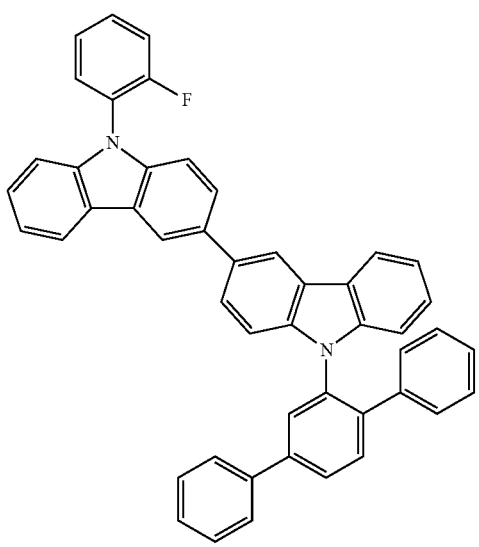

[173]
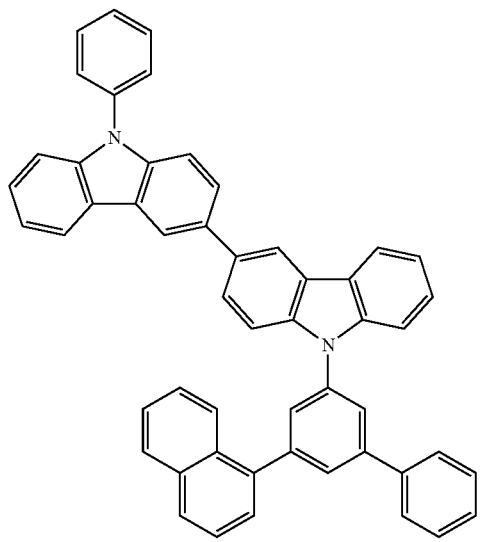
[175]
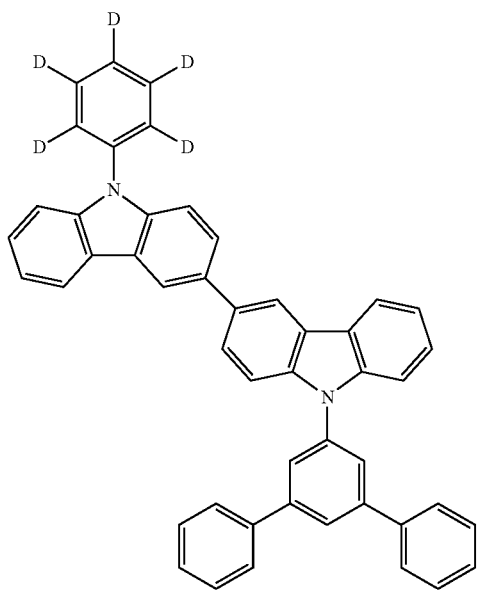
[174]
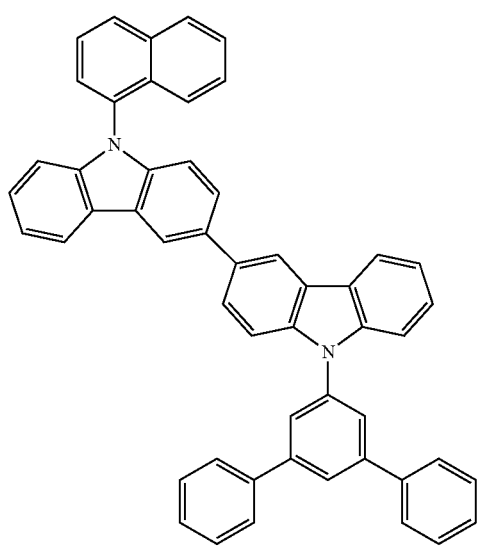
[176]
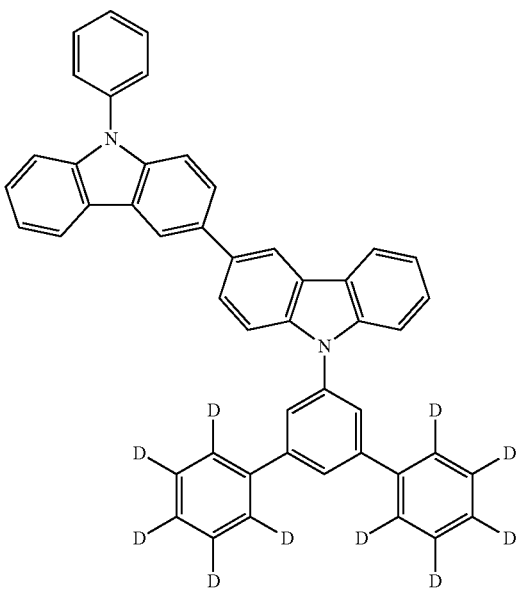

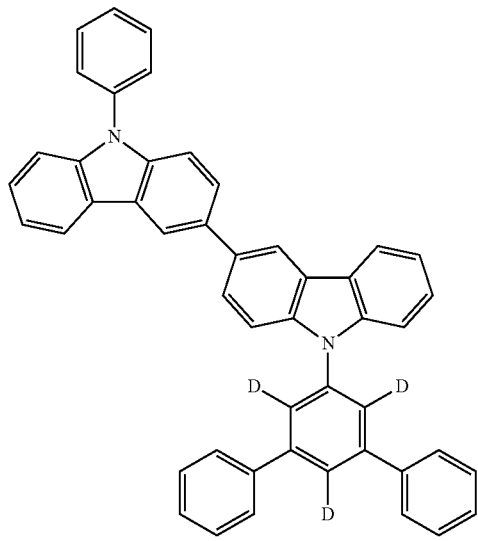
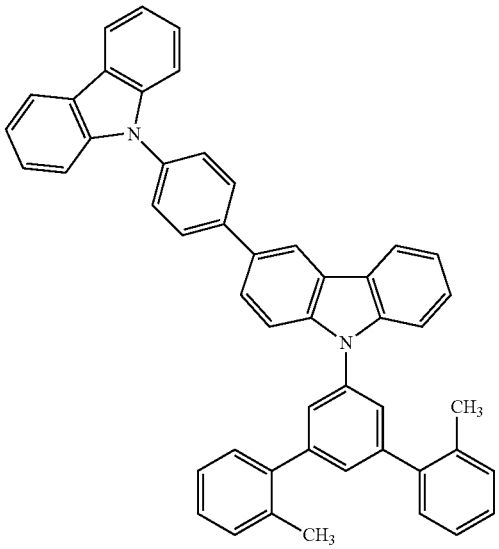
[Chemical Formula 24]

[183]
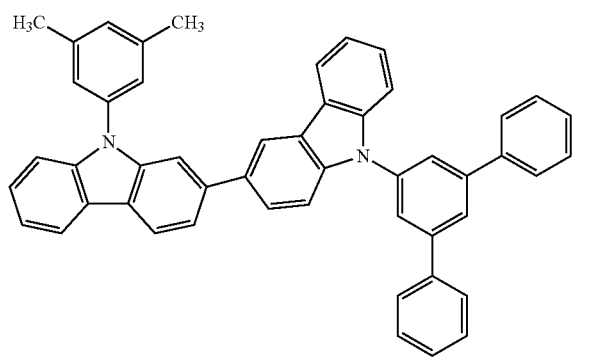
[184]
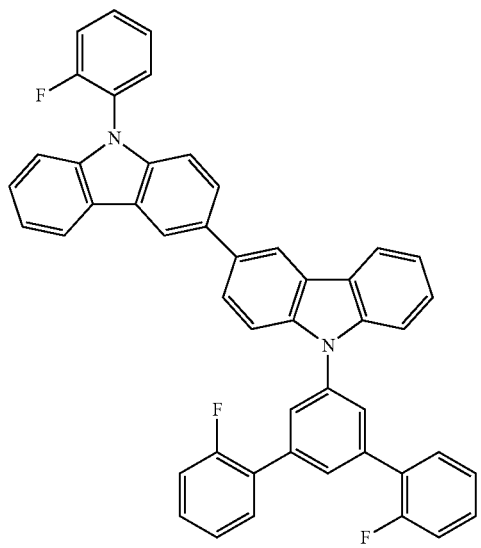
[185]
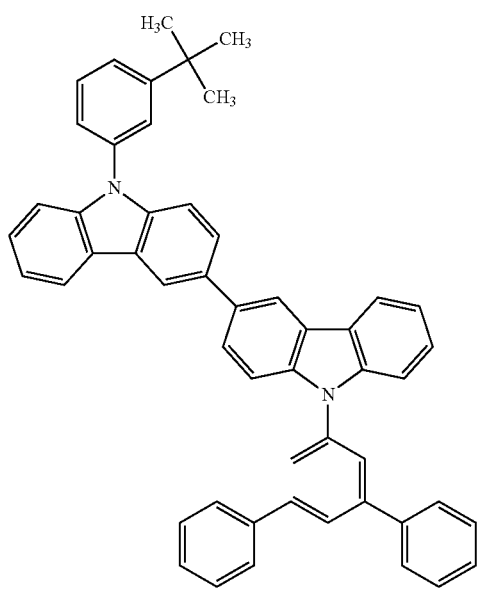
[186]
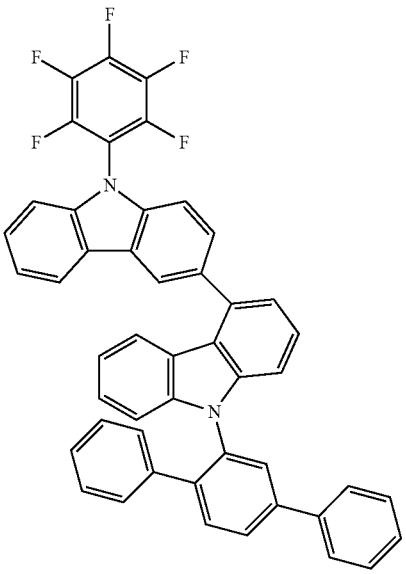
[187]
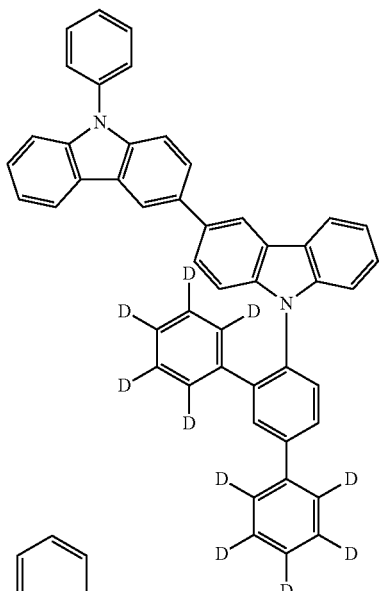
[188]
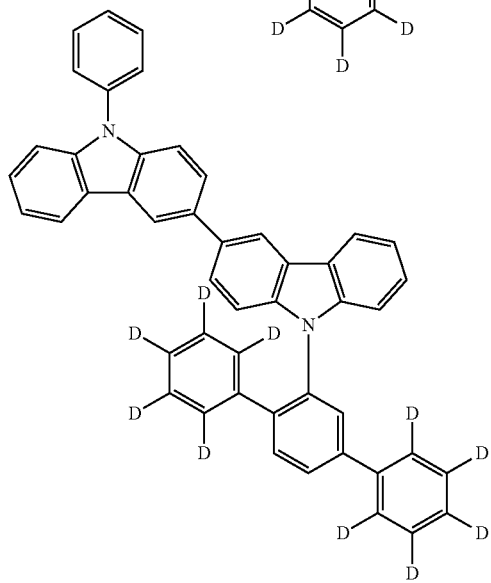

71
-continued
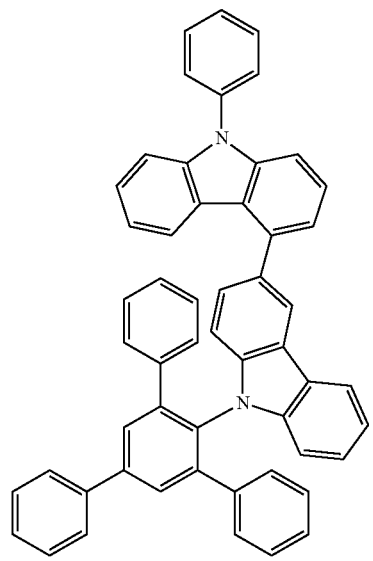
[190]
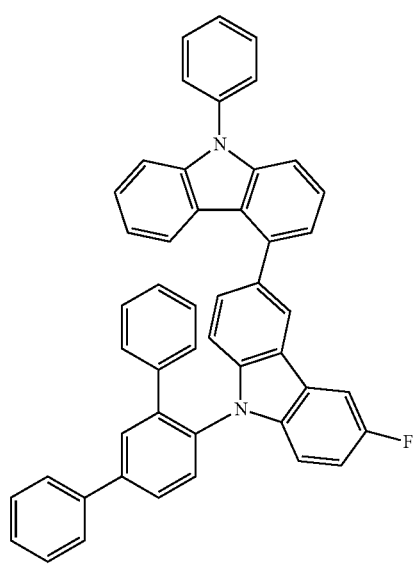
72
-continued
[191]
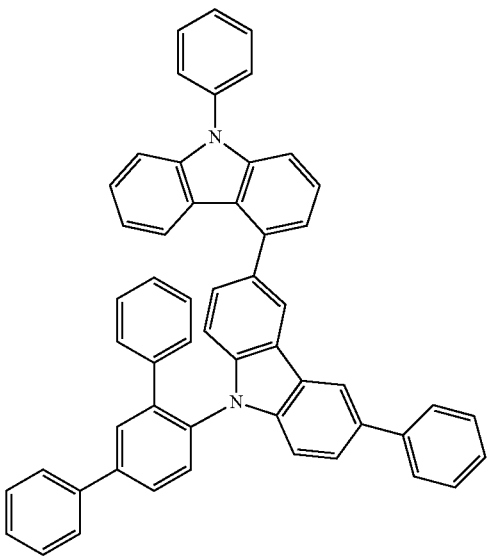
[192]
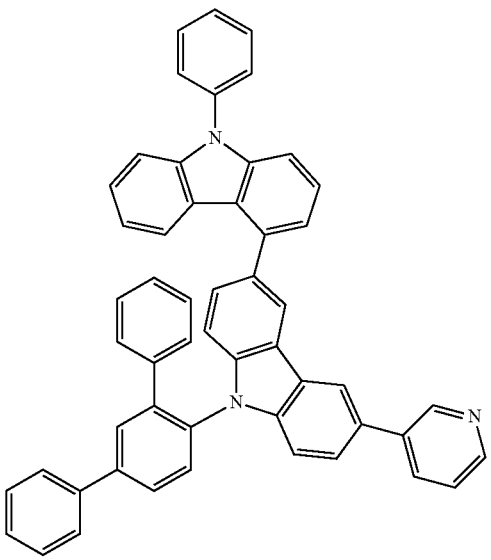

[Chemical Formula 25]
[Chemical Formula 25]
[Chemical Formula 25]
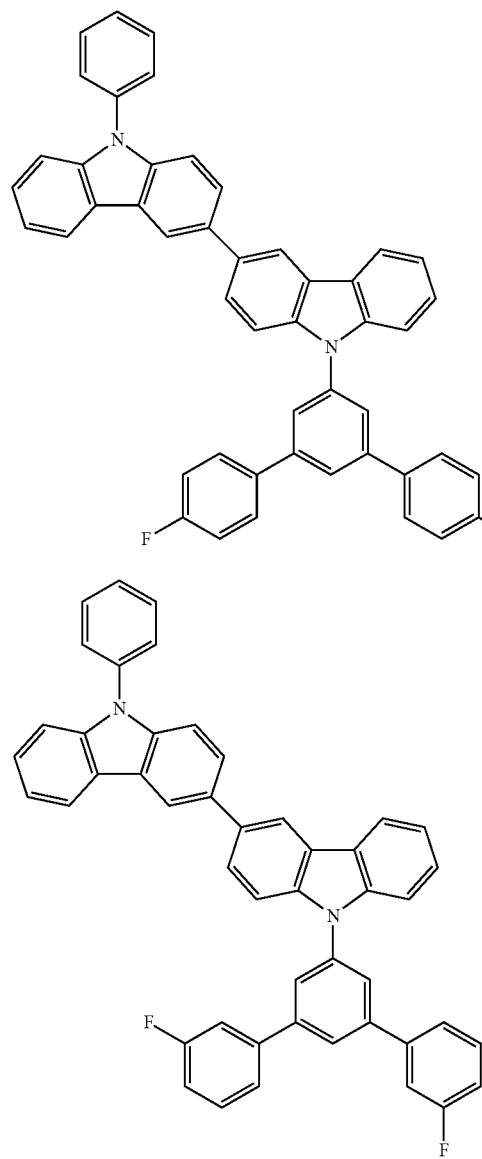
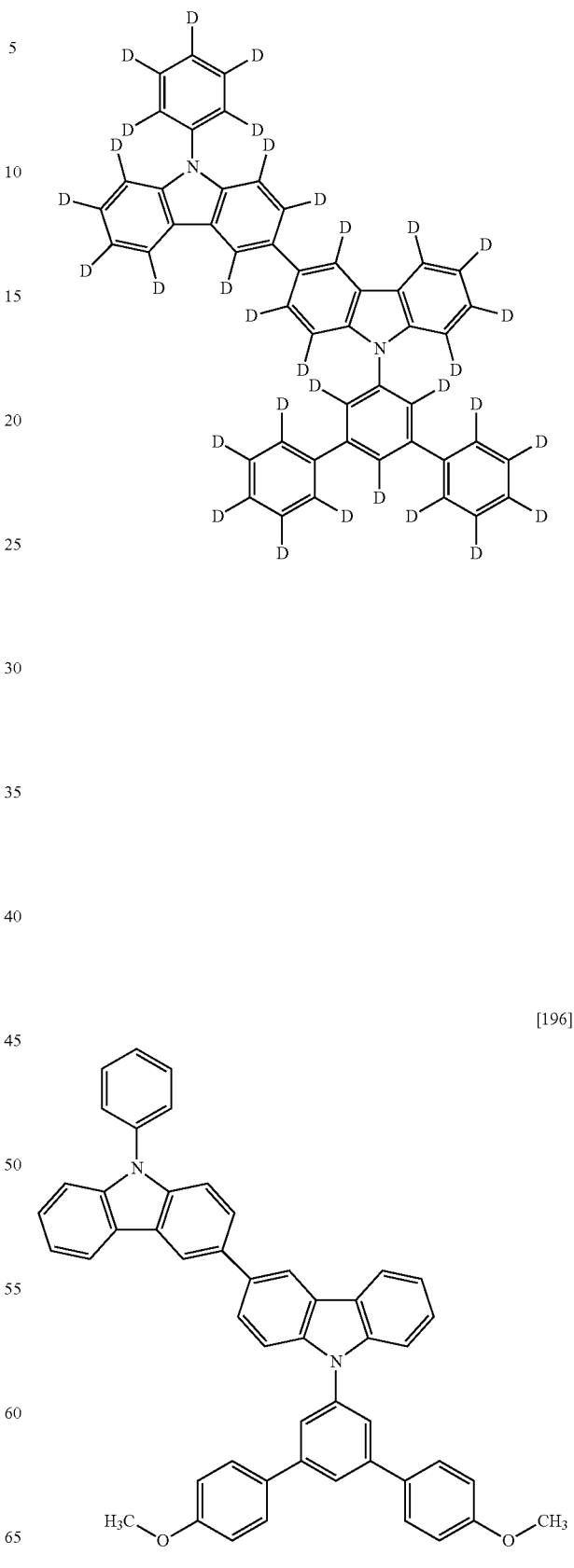

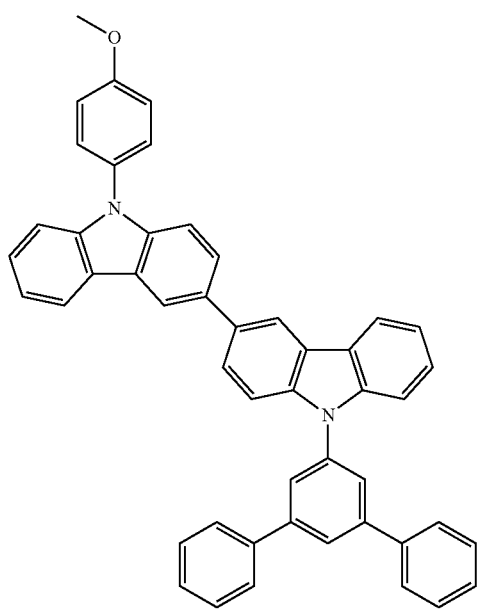
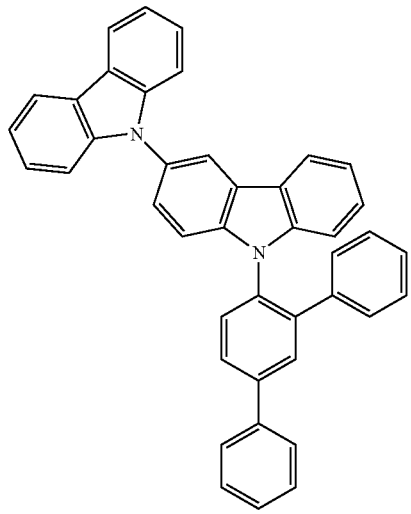
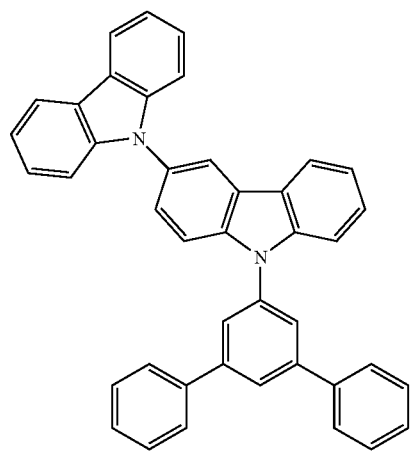
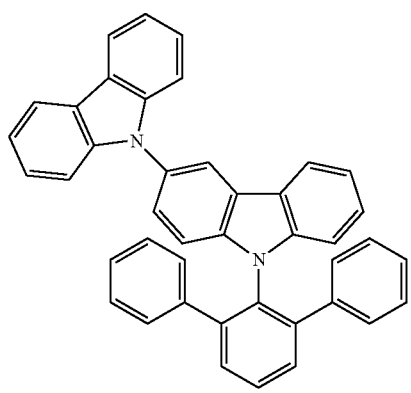
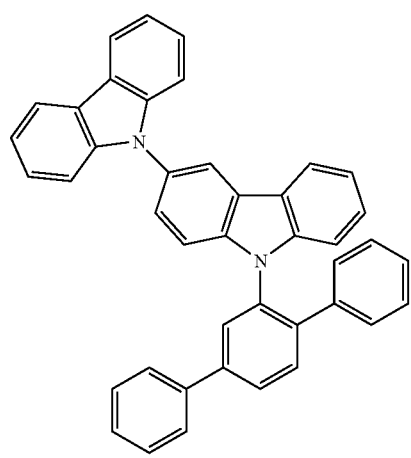
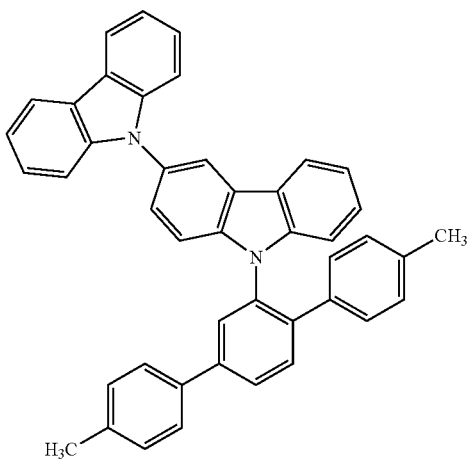

[203]

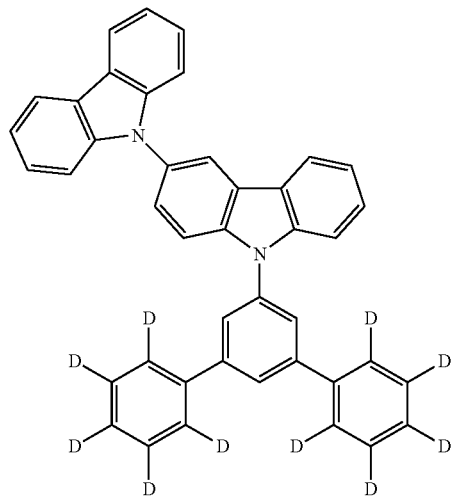

[204]

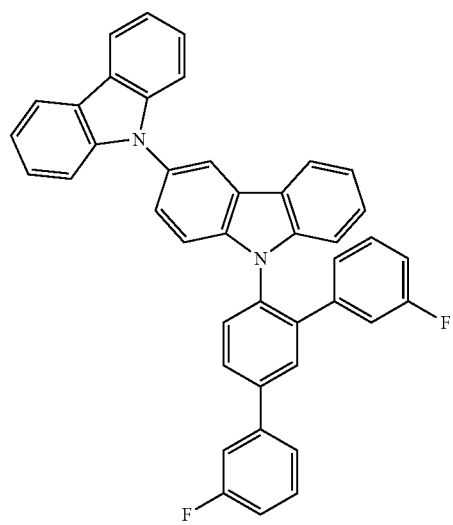

A known method can be used for synthesis of the carbazole skeleton-containing compound described above. Examples of the method for synthesizing a carbazole dimer include, but are not limited thereto, a method using a coupling reaction of a carbazole derivative with a halide or triflate using a palladium or copper catalyst. An example of using 9-phenylcarbazole-3-boronic acid is shown below as one example.

[Chemical Formula 26]

[Chemical Formula 26]

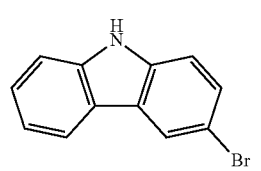

+

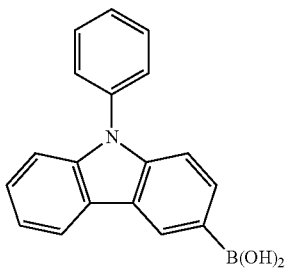

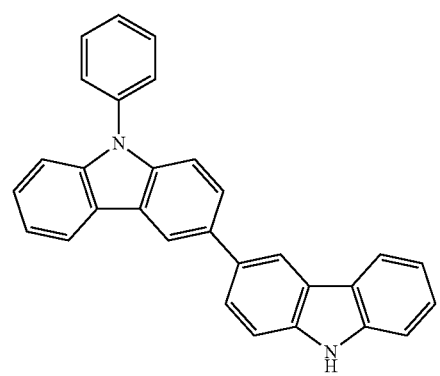

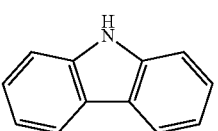

+

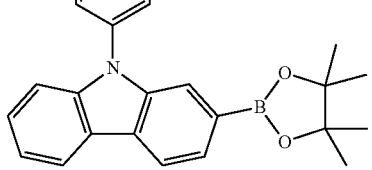

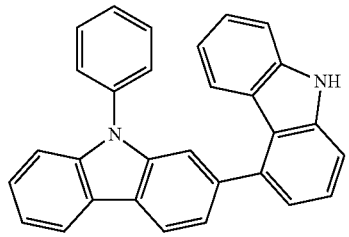

In the reaction described above, the reaction similarly proceeds even when 9-phenylcarbazole-2-boronic acid ester is used in place of 9-phenylcarbazole-3-boronic acid. In this case, a positional isomer of a carbazole dimer can be synthesized.

Examples of the method for introducing a substituent onto N of carbazole include, but are not limited thereto, a method using a coupling reaction of a carbazole derivative with a halide using a palladium or copper catalyst.

[Chemical Formula 27]

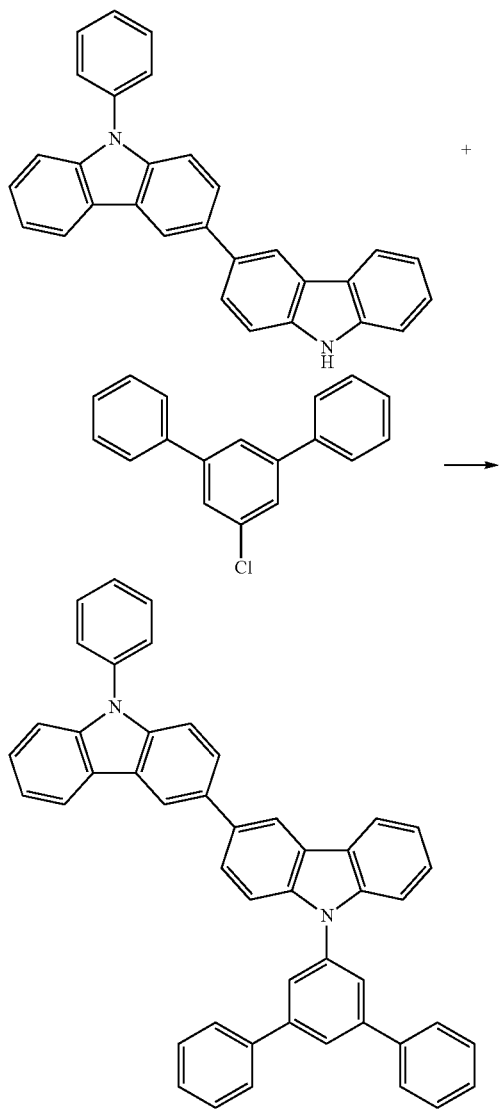

The compound represented by the general formula (1) is used as a light emitting device material. Herein, the light emitting device material in the present invention denotes a material to be used in any layer of a light emitting device and also includes a material to be used in a protective film of a cathode, in addition to materials to be used in a hole injection layer, a hole transporting layer, an emissive layer and/or an electron transporting layer as described later. Use of the compound represented by the general formula (1) in the present invention in any layer of a light emitting device can afford high luminance efficiency and also can afford a light emitting device superior in durability.

Next, embodiments of the light emitting device of the present invention will be described in detail. The light emitting device of the present invention has an anode and a cathode, and an organic layer interposed between the anode and the cathode, and the organic layer emits light by electric energy.

Examples of the layer configuration between the anode and the cathode in such a light emitting device include, besides configurations made up of only an emissive layer, laminated configurations such as 1) emissive layer/electron transporting layer, 2) hole transporting layer/emissive layer, 3) hole transporting layer/emissive layer/electron transporting layer, 4) hole injection layer/hole transporting layer/emissive layer/electron transporting layer, 5) hole transporting layer/emissive layer/electron transporting layer/electron injection layer, and 6) hole injection layer/hole transporting layer/emissive layer/electron transporting layer/electron injection layer. Each of the layers may be in the form of a single layer or a plurality of layers, and may be doped.

While the compound represented by the general formula (1) can be used for any layer of the layers described above in a light emitting device, it is particularly suitably used for a hole transporting layer or an emissive layer.

In the light emitting device of the present invention, the anode and the cathode have a role for supplying a sufficient current for light emission of the device, and it is desirable that at least one of them is transparent or translucent in order to take out light. Usually, the anode formed on a substrate is made to be a transparent electrode.

While the material to be used for an anode is not particularly limited and may be electroconductive metal oxides, such as zinc oxide, tin oxide, indium oxide, tin oxide indium (ITO), and zinc-oxide indium (IZO), metals, such as gold, silver, and chromium, inorganic electroconductive substances, such as copper iodide and copper sulfide, electroconductive polymers, such as polythiophene, polypyrrole, and polyaniline as long as being a material that is capable of injecting holes into an organic layer efficiently and that is transparent or translucent in order to take out light, use of ITO glass or NESA glass is particularly desirable. These electrode materials may be used alone, or a plurality of materials may be used in lamination or in admixture. Since it is favorable that a sufficient current for light emission of the device can be supplied, the resistance of a transparent electrode is not limited, but from the viewpoint of the power consumption of the device, a low resistance is desirable. For example, an ITO substrate having a resistance of 300Ω/□ or lower functions as a device electrode, but since currently, it is possible to supply a substrate having a resistance of about 10Ω/□, it is particularly desirable to use a substrate having a low resistance of 20Ω/□ or lower. The thickness of ITO can be arbitrarily selected according to a resistance value, but ITO is usually used at a thickness of between 50 to 300 nm in many cases.

In addition, in order to retain the mechanical strength of the light emitting device, it is preferable to form the light emitting device on a substrate. As the substrate, a glass substrate such as soda glass or alkali-free glass is suitably used. Since it is favorable that the thickness of a glass substrate has a sufficient thickness for retaining the mechanical strength, a thickness of 0.5 mm or more is sufficient. Regarding the material of glass, since it is preferable that the amount of ions eluted from glass is low, alkali-free glass is more preferable. Alternatively, since soda lime glass provided with a barrier coating such as SiO$_2$ is commercially available, it can also be used. Further, as far as a first electrode stably functions, it is not necessary that the substrate is glass and, for example, the anode may be formed on a plastic substrate. Examples of a method of forming an ITO film include, but are not particularly limited to, an electron beam method, a sputtering method, and a chemical reaction method.

A material used in the cathode is not particularly limited, as far as it is a substance which can efficiently inject electrons into the emissive layer. Generally, metals such as platinum, gold, silver, copper, iron, tin, aluminum, and indium, or alloys or multilayer lamination of these metals with metals having a low work function such as lithium, sodium, potassium, calcium and magnesium are preferable. Among them, as a main component, aluminum, silver, and magnesium are preferable from the viewpoints of electric resistance value, easiness of making a film, stability of a film, and luminance efficiency. In particular, when the material is constituted by magnesium and silver, electron injection into the electron transporting layer and the electron injection layer in the present invention becomes easy, and low voltage driving becomes possible, and therefore it is preferable.

Further, preferable examples include lamination of metals such as platinum, gold, silver, copper, iron, tin, aluminum, and indium, or alloys using these metals, inorganic substances such as silica, titania, and silicon nitride, and organic polymer compounds such as polyvinyl alcohol, polyvinyl chloride, and a hydrocarbon-based polymer compound as a protective film layer on the cathode for protecting the cathode. However, in the case of a device structure for taking out light from the cathode side (top emission structure), the protective film layer is selected from materials having light permeability in a visible light region. Examples of a method for preparation of these electrodes include, but are not particularly limited to, resistance heating, electron beam, sputtering, ion plating and coating.

The hole injection layer is a layer that is to be inserted to between an anode and a hole transporting layer. A single hole injection layer may be formed or, alternatively, a plurality of hole injection layers may be laminated. It is preferable that the hole injection layer is present between a hole transporting layer and an anode because this successfully results in lower voltage driving, increased durable life, and improvement in luminance efficiency due to improvement in the carrier balance of a device.

The material to be used for the hole injection layer is not particularly limited, and, for example, benzidine derivatives such as 4,4'-bis(N-(3-methylphenyl)-N-phenylamino)biphenyl (TPD), 4,4'-bis(N-(1-naphthyl)-N-phenylamino)biphenyl (NPD), 4,4'-bis(N,N-bis(4-biphenylyl)amino)biphenyl (TBDB), bis(N,N-diphenyl-4-aminophenyl)-N,N-diphenyl-4,4'-diamino-1,1'-biphenyl (TPD232) and $N^4,N^{4'}$-(([1,1'-biphenyl]-4,4'-diyl)bis($N^4,N^{4'},N^{4'}$-triphenyl-[1,1'-biphenyl]-4,4'-diamine); materials called starburst arylamines, such as 4,4',4"-tris(3-methylphenyl(phenyl)amino)triphenylamine (m-MTDATA) and 4,4',4"-tris(1-naphthyl(phenyl)amino)triphenylamine (1-TNATA); biscarbazole derivatives such as bis(N-arylcarbazole) or bis(N-alkylcarbazole); monocarbazole derivatives such as N-([1,1'-biphenyl]-4-yl)-9,9-dimethyl-N-(4-(9-phenyl-9H-carbazol-3-yl)phenyl)-9H-fluorene-2-amine; heterocyclic compounds such as pyrazoline derivatives, stilbene-based compounds, hydrazone-based compounds, benzofuran derivatives, thiophene derivatives, oxadiazole derivatives, phthalocyanine derivatives and porphyrin derivatives; and such polymers as polycarbonates and styrene derivatives having the aforementioned monomers on their side chains, polythiophene, polyaniline, polyfluorene, polyvinylcarbazole and polysilane are used. The compound represented by the general formula (1) may also be used. Especially, benzidine derivatives, starburst arylamine materials and monocarbazole derivatives are more preferably used from the viewpoint of having a lower HOMO level than the compound represented by the general formula (1) and injecting and transporting holes smoothly from an anode to a hole transporting layer.

Such materials may be used alone, or alternatively two or more materials may be used in admixture. A hole injection layer may be formed by laminating a plurality of materials. Moreover, it is more preferable that the hole injection layer is formed of an acceptor compound alone or the hole injection material described above is used with the material doped with an acceptor compound because if so, the effects described above will be more remarkably obtained. The acceptor compound is a material that forms a charge transfer complex with a hole transporting layer in contact therewith in the case where the compound is used in the form of a single layer film or forms a charge transfer complex with a material that constitutes a hole injection layer in the case where the compound is used while being doped into the material. Use of such a material improves the electrical conductivity of a hole injection layer and contributes more to drop the driving voltage of a device, thereby affording effects such as improvement in luminance efficiency and improvement in durable life.

Examples of the acceptor compound include metal chlorides such as iron(III) chloride, aluminum chloride, gallium chloride, indium chloride, and antimony chloride, metal oxides such as molybdenum oxide, vanadium oxide, tungsten oxide, and ruthenium oxide, and charge transfer complexes such as tris(4-bromophenyl)aminium hexachloroantimonate (TBPAH). Moreover, organic compounds having a nitro group, a cyano group, halogen, or a trifluoromethyl group in the molecule, quinone-based compounds, acid anhydride-based compounds, and fullerenes can also be used suitably. Specific examples of such compounds include hexacyanobutadiene, hexacyanobenzene, tetracyanoethylene, tetracyanoquinodimethane (TCNQ), tetrafluorotetracyanoquinodimethane (F4-TCNQ), radialene derivatives such as 4,4',4"-((1E,1'E,1"E)-cyclopropane-1,2,3-triylidenetris(cyanomethanylylidene))tris(2,3,5,6-tetrafluorobenzonitrile), p-fluoranil, p-chloranil, p-bromanil, p-benzoquinone, 2,6-dichlorobenzoquinone, 2,5-dichlorobenzoquinone, tetramethylbenzoquinone, 1,2,4,5-tetracyanobenzene, o-dicyanobenzene, p-dicyanobenzene, dipyrazino[2,3-f:2',3'-h]quinoxaline-2,3,6,7,10,11-hexacarbonitrile ($HAT(CN)_6$), 1,4-dicyanotetrafluorobenzene, 2,3-dichloro-5,6-dicyanobenzoquinone, p-dinitrobenzene, m-dinitrobenzene, o-dinitrobenzene, p-cyanonitrobenzene, m-cyanonitrobenzene, o-cyanonitrobenzene, 1,4-naphthoquinone, 2,3-dichloronaphthoquinone, 1-nitronaphthalene, 2-nitronaphthalene, 1,3-dinitronaphthalene, 1,5-dinitronaphthalene, 9-cyanoanthracene, 9-nitroanthracene, 9,10-anthraquinone, 1,3,6,8-tetranitrocarbazole, 2,4,7-trinitro-9-fluorenone, 2,3,5,6-tetracyanopyridine, maleic anhydride, phthalic anhydride, C60, and C70.

Of these, metal oxides and cyano group-containing compounds are preferable because they can be easily handled and deposited and therefore the above-described effects can be obtained easily. In either of the case where a hole injection layer is formed of an acceptor compound alone or the case where a hole injection layer is doped with an acceptor compound, the hole injection layer may be a single layer or may be formed of a plurality of layers laminated.

The hole transporting layer is a layer that transports to an emissive layer holes injected from an anode. The hole transporting layer may be formed of either a single layer or a plurality of layers laminated.

The compound represented by the general formula (1) is preferably used for a hole injection layer and hole transporting layer of a light emitting device because the compound has an ionization potential of 5.3 to 6.0 eV (value of a deposited film measured using AC-2 (manufactured by RIKEN KEIKI Co., Ltd.)), a high triplet level, high hole transporting property, and high film stability. The compound represented by the general formula (1) has a greater energy gap as compared to conventional hole transporting materials having a benzidine skeleton, and therefore has a high LUMO level and is excellent in electron blocking property. Moreover, it is preferable to use the compound represented by the general formula (1) as a hole transporting material of a device using a triplet emissive material. This is because the compound represented by the general formula (1) has a high triplet level and therefore does not cause the problem with conventional hole transporting materials having a benzidine skeleton that leak of triplet excitation energy occurs and luminance efficiency drops if the materials are in contact directly with an emissive layer containing a triplet emitter dopant because of the low triplet levels of the materials.

When being formed of a plurality of hole transporting layers, it is preferable that a hole transporting layer containing the compound represented by the general formula (1) is in contact with an emissive layer directly. This is because the compound represented by the general formula (1) has high electron blocking property and therefore can prevent the invasion of electrons flowing out of the emissive layer. Moreover, the compound represented by the general formula (1) has a high triplet level and therefore also has an effect of trapping the excitation energy of a triplet emissive material. Accordingly, it is preferable that a hole transporting layer containing the compound represented by the general formula (1) is in direct contact with an emissive layer also when a triplet emissive material is contained in the emissive layer. In particular, when an electron transporting host material is used for the emissive layer, excitons generated in the emissive layer are likely leaked to the hole transporting layer side, and therefore the compound of the present invention, which has a high triplet level, is suitably used.

The hole transporting layer may be formed of only the compound represented by formula (1) or alternatively may be incorporated with other materials as long as the effects of the present invention are not impaired. In this case, examples of the other materials to be used include benzidine derivatives such as 4,4'-bis(N-(3-methylphenyl)-N-phenylamino)biphenyl (TPD), 4,4'-bis(N-(1-naphthyl)-N-phenylamino)biphenyl (NPD), 4,4'-bis(N,N-bis(4-biphenylyl)amino)biphenyl (TBDB), bis(N,N'-diphenyl-4-aminophenyl)-N,N-diphenyl-4,4'-diamino-1,1'-biphenyl (TPD232) and $N^4,N^{4'}$-([1,1'-biphenyl]-4,4'-diyl)bis($N^4,N^{4'},N^{4'}$-triphenyl-[1,1'-biphenyl]-4, 4'-diamine); materials called starburst arylamines, such as 4,4',4"-tris(3-methylphenyl(phenyl)amino)triphenylamine (m-MTDATA) and 4,4',4"-tris(1-naphthyl(phenyl)amino) triphenylamine (1-TNATA); biscarbazole derivatives such as bis(N-arylcarbazole) or bis(N-alkylcarbazole); monocarbazole derivatives such as N-([1,1'-biphenyl]-4-yl)-9,9-dimethyl-N-(4-(9-phenyl-9H-carbazol-3-yl)phenyl)-9H-fluorene-2-amine; heterocyclic compounds such as pyrazoline derivatives, stilbene-based compounds, hydrazone-based compounds, benzofuran derivatives, thiophene derivatives, oxadiazole derivatives, phthalocyanine derivatives and porphyrin derivatives; and such polymers as polycarbonates and styrene derivatives having the aforementioned monomers on their side chains, polythiophene, polyaniline, polyfluorene, polyvinylcarbazole and polysilane.

The emissive layers may be in the form of a single layer or a plurality of layers, each of which is formed of an emissive material (host material, dopant material), and this may be a mixture of the host material and the dopant material, or the host material alone. That is, in the light emitting device of the present invention, only the host material or the dopant material may emit light, or both of the host material and the dopant material emit light, in each emissive layer. From the viewpoints that electric energy is efficiently utilized, and light emission at high color purity is obtained, it is preferable that the emissive layer includes a mixture of the host material and the dopant material. In addition, the host material and the dopant material may be one kind or a combination of a plurality of kinds, respectively. The dopant material may be contained in a whole host material, or may be partially contained therein. The dopant material may be laminated, or may be dispersed. The dopant material can control an emitted color. When the amount of the dopant material is too large, concentration quenching occurs, and therefore the dopant material is used in an amount of preferably 30% by weight or less, further preferably 20% by weight or less based on the host material. As a doping method, the dopant material can be co-deposited with the host material, or the dopant material may be mixed with the host material in advance to be co-deposited simultaneously.

Besides the compound represented by the general formula (1), examples of the emissive material that can be used include, but are not particularly limited to, fused ring derivatives such as anthracene and pyrene, metal chelated oxinoid compounds including tris(8-quinolinolate)aluminum, bisstyryl derivatives such as bisstyrylanthracene derivatives and distyrylbenzene derivatives, tetraphenylbutadiene derivatives, indene derivatives, coumarin derivatives, oxadiazole derivatives, pyrrolopyridine derivatives, perinone derivatives, cyclopentadiene derivatives, oxadiazole derivatives, thiadiazolopyridine derivatives, dibenzofuran derivatives, dibenzothiophene derivatives, carbazole derivatives, and indolocarbazole derivatives and, as a polymer series, polyphenylenevinylene derivatives, polyparaphenylene derivatives, and polythiophene derivatives, which have hitherto been known as a light emitting body.

The host material contained in the emissive material need not be restricted to only one type of compound, and a plurality of compounds of the present invention may be used in admixture or a compound of the present invention may be used in an admixture with one or more other host materials. Alternatively, those materials may be laminated. Examples of the host material which can be mixed include, but are not particularly limited to, compounds having a fused aryl ring such as naphthalene, anthracene, phenanthrene, pyrene, chrysene, naphthacene, triphenylene, perylene, fluoranthene, fluorene, and indene, and derivatives thereof, aromatic amine derivatives such as N,N'-dinaphthyl-N,N'-diphenyl-4,4'-diphenyl-1,1'-diamine, metal chelated oxinoid compounds including tris(8-quinolinato)aluminum (III), bisstyryl derivatives such as distyrylbenzene derivatives, tetraphenylbutadiene derivatives, indene derivatives, coumarin derivatives, oxadiazole derivatives, pyrrolopyridine derivatives, perinone derivatives, cyclopentadiene derivatives, pyrrolopyrrole derivatives, thiadiazolopyridine derivatives, dibenzofuran derivatives, carbazole derivatives, indolocarbazole derivatives, pyrimidine derivatives and triazine derivatives and, as a polymer series, polyphenylenevinylene derivatives, polyparaphenylene derivatives, polyfluorene derivatives, polyvinylcarbazole derivatives, and polythiophene derivatives. Especially, metal chelated oxinoid compounds, dibenzofuran derivatives, dibenzothiophene derivatives, carbazole derivatives, indolocarbazole derivatives, pyrimidine derivatives, triazine derivatives, triphenylene derivatives and the like are suitably used as a host which is used when the emissive layer performs triplet emission (phosphorescence emission).

In particular, the compound represented by the general formula (1) is preferably used for an emissive layer of a light emitting device because the compound has an ionization potential of 5.3 to 6.0 eV (value of a deposited film measured using AC-2 (manufactured by RIKEN KEIKI Co., Ltd.)), a high triplet level, high hole transporting property, and high film stability. The compound represented by the general formula (1) has a greater energy gap as compared to conventional high-hole transporting materials having a benzidine skeleton, and therefore has a high LUMO level and is excellent in electron blocking property. Moreover, it is preferable to use the compound represented by the general formula (1) as a host material of a device using a triplet emissive material. This is because the compound represented by the general formula (1) has a high triplet level and therefore does not cause the problem with conventional materials that leak of triplet excitation energy occurs and luminance efficiency drops if the materials are in contact directly with an emissive layer containing a triplet emitter dopant because of the low triplet levels of the materials. The compound represented by the general formula (1) can be used as a hole transporting host because it shows a good hole injection transporting property as described above, and has an improved electron blocking property. Further, use of the compound in combination with an electron transporting host is preferred because carriers in an emissive layer increase, so that the probability of recombination is increased, resulting in enhancement of luminance efficiency. The electron transporting host material is not particularly limited, but a carbazole compound containing a pyrimidine skeleton or a triazine skeleton or a compound having a carbazole site is suitably used.

The dopant material contained in the emissive material is not particularly limited, and examples thereof include compounds having an aryl ring, such as naphthalene, anthracene, phenanthrene, chrysene, fluorene, benzofluorene, pyrene, triphenylene, perylene, fluorene and indene, or derivatives thereof (e.g. 2-(benzothiazole-2-yl)-9,10-diphenylanthracene, 5,6,11,12-tetraphenylnaphthacene and the like); compounds having a heteroaryl ring, such as furan, pyrrole, thiophene, silole, 9-silafluorene, 9,9'-spirobisilafluorene, benzothiophene, benzofuran, indole, dibenzothiophene, dibenzofuran, imidazopyridine, phenanthroline, pyrazine, naphthyridine, quinoxaline, pyrrolopyridine and thioxanthene, or derivatives thereof; distyrylbenzene derivatives; aminostyryl derivatives such as 4,4'-bis(2-(4-diphenylaminophenyl)ethenyl)biphenyl and 4,4'-bis(N-(stilbene-4-yl)-N-phenylamino)stilbene; aromatic acetylene derivatives; tetraphenylbutadiene derivatives; stilbene derivatives; aldazine derivatives; pyrromethene derivatives; diketopyrrolo[3,4-c] pyrrole derivatives; coumarin derivatives such as 2,3,5,6-1H, 4H-tetrahydro-9-(2'-benzothiazolyl)quinolizino[9,9a,1-gh] coumarin; azole derivatives such as imidazole, thiazole, thiadiazole, carbazole, oxazole, oxadiazole and triazole, and metal complexes thereof; and aromatic amine derivatives represented by N,N'-diphenyl-N,N'-di(3-methylphenyl)-4,4'-diphenyl-1,1'-diamine.

In particular, the dopant to be used when an emissive layer is engaged in triplet light emission (emission of phosphorescence) is preferably a metal complex compound containing at least one metal selected from the group consisting of iridium (Ir), ruthenium (Ru), palladium (Pd), platinum (Pt), osmium (Os), and rhenium (Re). It is preferable that the ligand has a nitrogen-containing aromatic heterocyclic ring such as a phenylpyridine skeleton or a phenylquinoline skeleton. However, the complex is not limited thereto, and a suitable complex is selected in context with an emitted color, a device performance and a host compound to be required. Specific examples thereof include a tris(2-phenylpyridyl) iridium complex, a tris{2-(2-thiophenyl)pyridyl}iridium complex, a tris{2-(2-benzothiophenyl)pyridyl}iridium complex, a tris (2-phenylbenzothiazole) iridium complex, a tris(2-phenylbenzoxazole) iridium complex, a trisbenzoquinoline iridium complex, a bis(2-phenyl pyridyl)(acetylacetonato) iridium complex, a bis{2-(2-thiophenyl)pyridyl}iridium complex, a bis{2-(2-benzothiophenyl)pyridyl}(acetylacetonato) iridium complex, a bis(2-phenylbenzothiazole)(acetylacetonato) iridium complex, a bis(2-phenylbenzoxazole)(acetylacetonato) iridium complex, a bisbenzoquinoline(acetylacetonato) iridium complex, a bis{2-(2,4-difluorophenyl)pyridyl}(acetylacetonato) iridium complex, a tetraethylporphyrin platinum complex, a {tris(thenoyltrifluoroacetone)-mono(1,10-phenanthroline)}europium complex, a {tris(thenoyltrifluoroacetone)-mono(4,7-diphenyl-1,10-phenanthroline)}europium complex, a {tris(1,3-diphenyl-1,3-propanedione)-mono(1,10-phenanthroline)}europium complex, and a trisacetylacetone terbium complex. Moreover, a phosphorescence dopant disclosed in JP-A-2009-130141 is also used suitably. Although not limited to these, an iridium complex or a platinum complex is used preferably because highly efficient light can be obtained easily.

Regarding the above-described triplet emissive materials to be used as a dopant material, only one material may be contained in an emissive layer or, alternatively, two or more materials may be used in admixture. When two or more triplet emissive materials are used, the total weight of the dopant materials is preferably 30% by weight or less, further preferably 20% by weight or less based on the host material.

The emissive layer may further contain a third component for adjusting the carrier balance in the emissive layer or for stabilizing the layer structure of the emissive layer in addition to the above-described host material and the triplet emissive material. A material that does not cause interaction between a host material made of the carbazole skeleton-containing compound represented by the general formula (1) and a dopant material made of a triplet emissive material is selected as the third component.

Preferable host and dopant in a triplet emission system are not particularly limited, and specific examples thereof include the following.

[Chemical Formula 28]

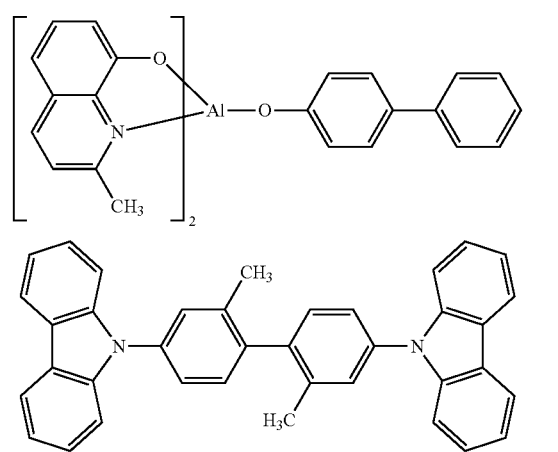

[Chemical Formula 28]

87
-continued
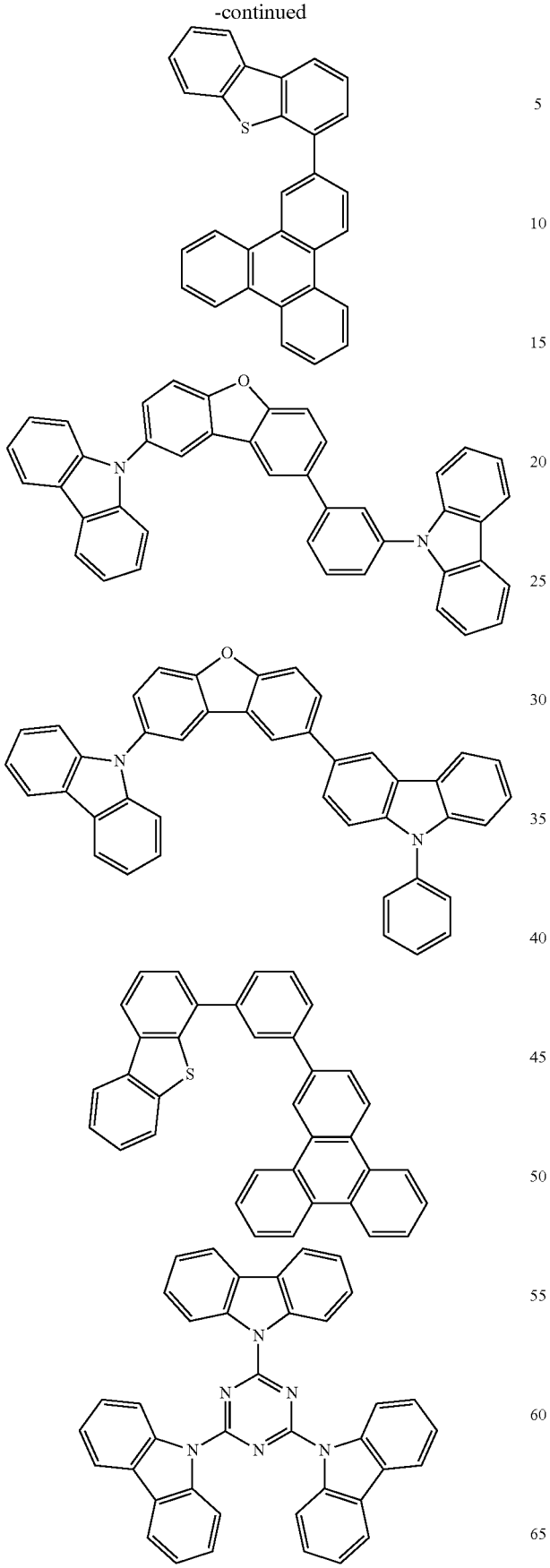
88
-continued
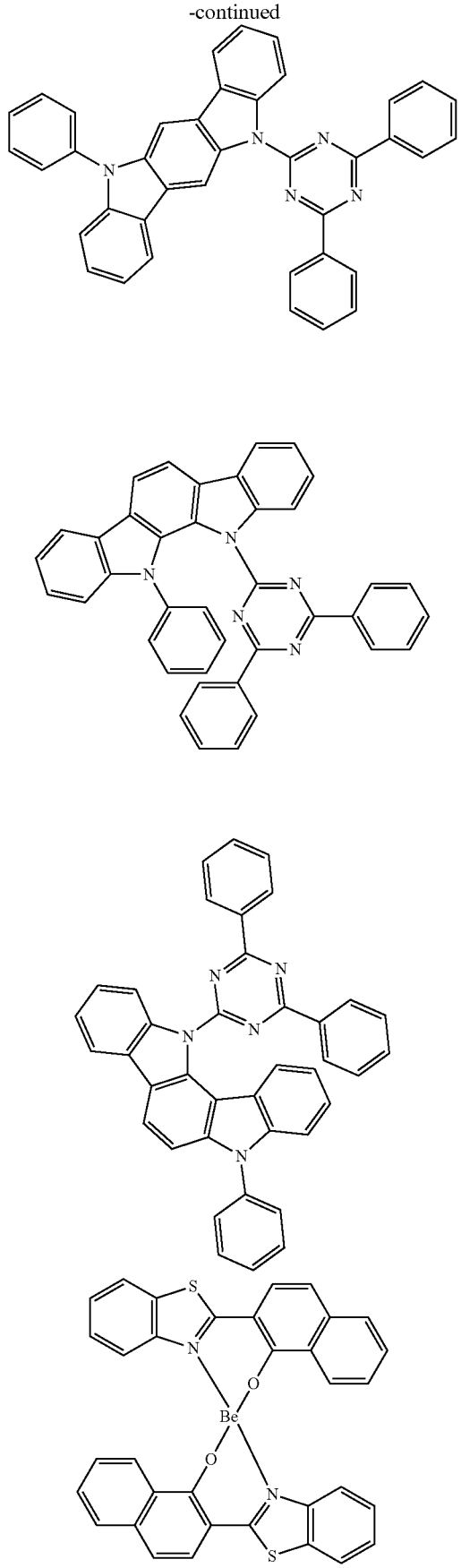

-continued
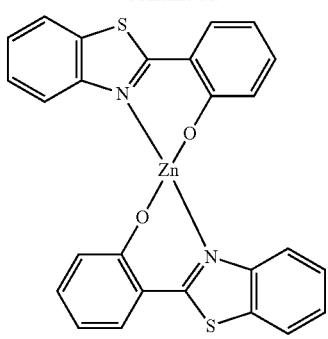
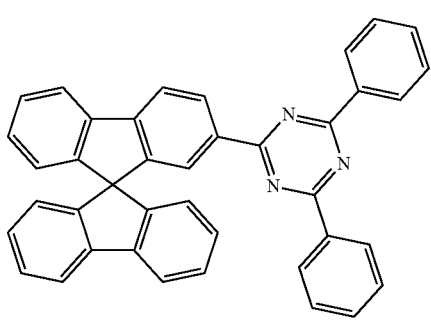
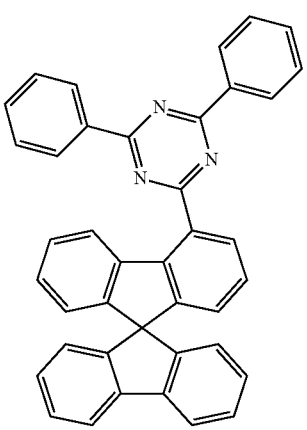
-continued
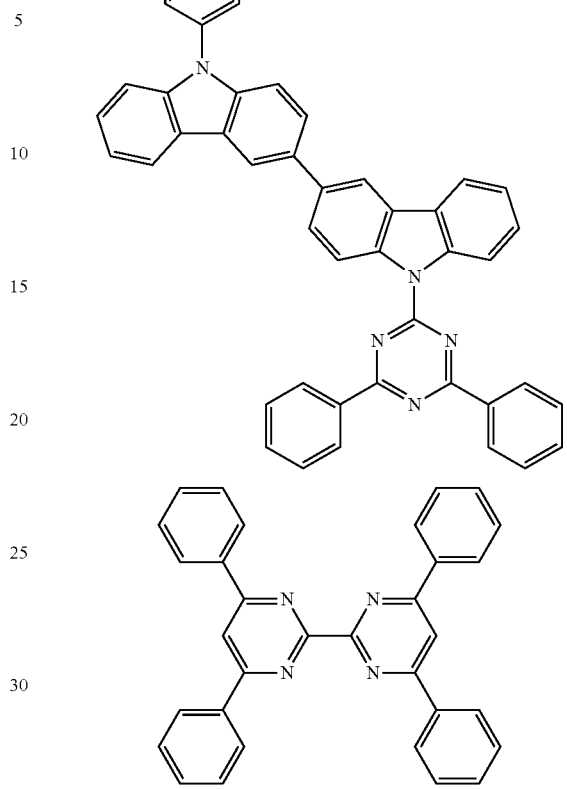
[Chemical Formula 29]
[Chemical Formula 29]
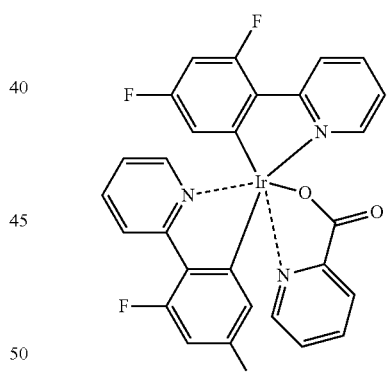
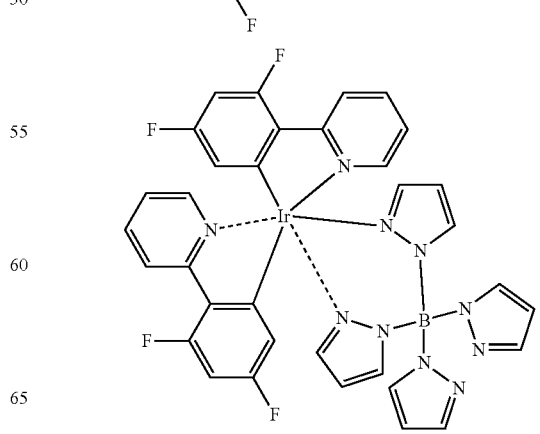

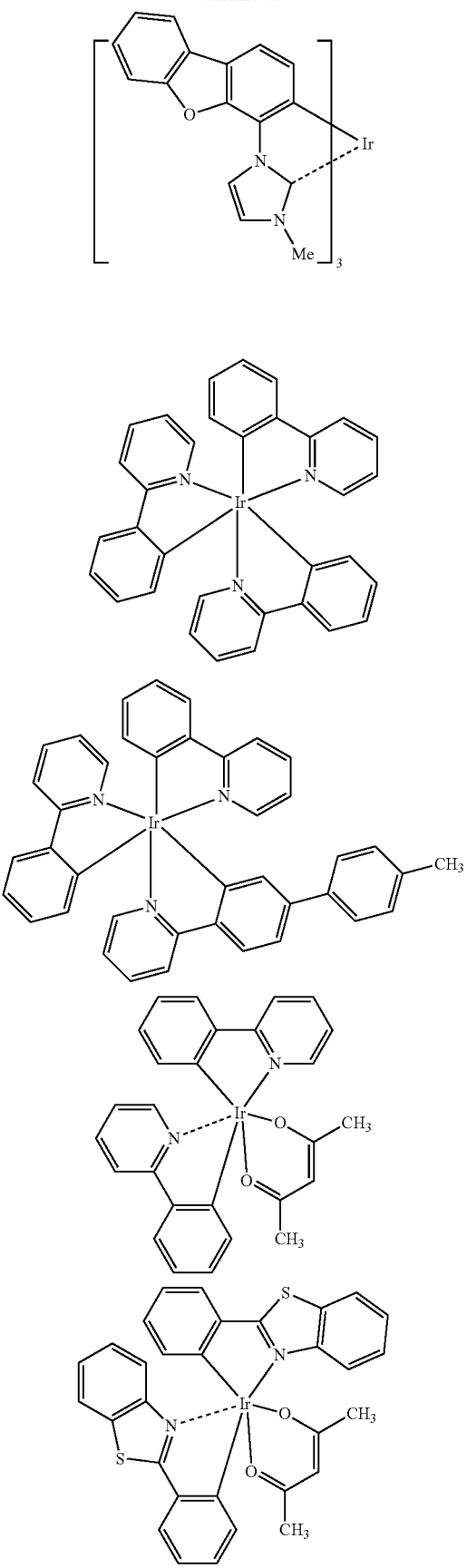
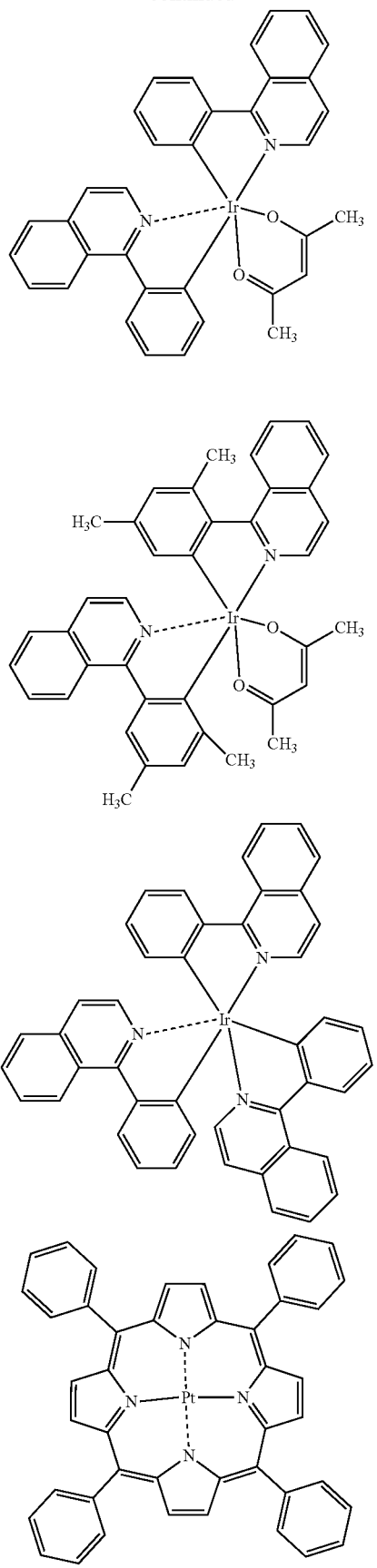

-continued

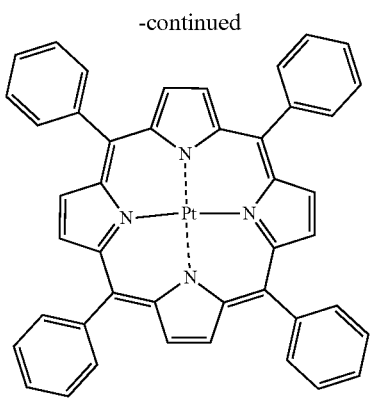

In addition thereto, hosts and dopants may also be used which are disclosed in Appl. Phys. Lett. 78, 1622 (2001), Nature 395, 151 (1998), Appl. Phys. Lett. 90, 123509 (2007), Org. Electron. 1, 15 (2000), US 2005-202194 A, WO 2005-14551 A, US 2003-175553 A, WO 2001-39234 A, US 2006-0280965 A, Appl. Phys. Lett. 77, 2280 (2000), WO 2004-93207 A, WO 2005-89025 A, WO 2006-132173 A, JP 2005-11610 A, JP 2007-254297 A, WO 2007-63796 A, WO 2007-63754 A, WO 2008-56746 A, WO 2008-146839 A, WO 2009-84546 A, WO 2005-30900 A, WO 2006-114966 A, US 2006-835469 A, US 2006-202194 A, US 2007-087321 A, Adv. Mater. 19, 739 (2007), WO 2003-40257 A, Chem. Mater. 17, 3532 (2005), Adv. Mater. 17, 1059 (2005), Inorg. Chem. 40, 1704 (2001), US 2002-034656 A, US 2006-687266 A, Chem. Mater. 16, 2480 (2004), US 2007-190359 A, US 2006-008670 A, JP 2007-123392 A, Adv. Mater. 16, 2003 (2004), Angew. Chem. Int. Ed. 2006, 45, 7800, Appl. Phys. Lett. 86, 153505 (2005), Chem. Lett. 34, 592 (2005), Chem. Commun. 2906 (2005), Inorg. Chem. 42, 1248 (2003), WO 2002-2714 A, WO 2006-9024 A, US 2006-251923 A, WO 2006-56418 A, US 2005-260441 A, US 2007-190359 A, US 2002-134984 A, Angew. Chem. Int. Ed. 47, 1 (2008), Chem. Mater. 18, 5119 (2006), Inorg. Chem. 46, 4308 (2007), WO 2005-123873 A, WO 2007-4380 A, WO 2006-82742 A, US 2005-260449 A, Organometallics 23, 3745 (2004), Appl. Phys. Lett. 74, 1361 (1999), WO 2006-98120 A, WO 2006-103874 A, WO 2012-13271 A, WO 2011-141109 A, WO 2011-55934 A, WO 2011-139055 A, WO 2011-137072 A, WO 2011-125680 A, WO 2011-132684 A, WO 2011-132683 A and so on.

In the present invention, the electron transporting layer is a layer in which electrons are injected from the cathode and, further, which transports the electrons. It is desired that the electron transporting layer has a high electron injection efficiency, and efficiently transports injected electrons. For this reason, it is required that the electron transporting layer is constituted by a substance having great electron affinity and, moreover, great electron mobility and, further, excellent stability, and generating impurities that become a trap with difficulty at the time of production and at the time of use. In particular, when layers are laminated at a large thickness, since a low-molecular weight compound is crystallized etc., and the film quality is easily deteriorated, a compound having a molecular weight of 400 or more which retains stable film quality is preferable. However, when transportation balance between holes and electrons is considered, if the electron transporting layer mainly plays a role of being able to inhibiting holes from the anode from flowing to the cathode side without recombination, even when the layer is constituted by a material having not so high electron transporting ability, the effect of improving luminance efficiency becomes equivalent to that when the layer is constituted by a material having high electron transporting ability. Therefore, the electron transporting layer in the present invention also includes a hole inhibition layer which can efficiently inhibit the transfer of holes as the same meaning.

Examples of the electron transporting material to be used for the electron transporting layer include fused polycyclic aromatic derivatives, such as naphthalene and anthracene, styryl-based aromatic derivatives typified by 4,4'-bis(diphenylethenyl)biphenyl, quinone derivatives, such as anthraquinone and diphenoquinone, phosphorus oxide derivatives, and various types of metal complexes, such as quinolinol complexes, e.g., tris(8-quinolinolate)aluminum (III), benzoquinolinol complexes, hydroxyazole complexes, azomethine complexes, tropolone metal complexes, and flavonol metal complexes. It is preferable to use a compound that includes an element selected from carbon, hydrogen, nitrogen, oxygen, silicon, and phosphorus and has a heteroaryl ring structure containing an electron-accepting nitrogen because it can reduce a driving voltage and a highly efficient light emission can be obtained.

The electron-accepting nitrogen referred to herein denotes a nitrogen atom which forms a multiple bond between adjoining atoms. Since nitrogen atoms have high electronegativity, the multiple bond has an electron-accepting nature. For this reason, an aromatic heterocyclic ring containing electron-accepting nitrogen has high electron affinity. An electron transporting material having electron-accepting nitrogen makes easier acceptance of electrons from a cathode having higher electron affinity, and lower voltage driving becomes possible. In addition, since supply of electrons to an emissive layer is increased and a recombining probability is increased, luminance efficiency is increased.

Examples of the heteroaryl ring containing electron-accepting nitrogen include a pyridine ring, a pyrazine ring, a pyrimidine ring, a quinoline ring, a quinoxaline ring, a naphthylidine ring, a pyrimidopyrimidine ring, a benzoquinoline ring, a phenanthroline ring, an imidazole ring, an oxazole ring, an oxadiazole ring, a triazole ring, a thiazole ring, a thiadiazole ring, a benzoxazole ring, a benzothiazole ring, a benzimidazole ring, and a phenanthroimidazole ring.

Examples of preferred compounds having such a heteroaryl ring structure include benzimidazole derivatives, benzoxazole derivatives, benzthiazole derivatives, oxadiazole derivatives, thiadiazole derivatives, triazole derivatives, pyrazine derivatives, phenanthroline derivatives, quinoxaline derivatives, quinoline derivatives, benzoquinoline derivatives, oligopyridine derivatives such as bipyridine and terpyridine, quinoxaline derivatives and naphthylidine derivatives. Among them, imidazole derivatives such as tris(N-phenylbenzimidazol-2-yl)benzene; oxadiazole derivatives such as 1,3-bis[(4-tert-butylphenyl)1,3,4-oxadiazolyl]phenylene; triazole derivatives such as N-naphthyl-2,5-diphenyl-1,3,4-triazole; phenanthroline derivatives such as bathocuproine and 1,3-bis(1,10-phenanthrolin-9-yl)benzene; benzoquinoline derivatives such as 2,2'-bis(benzo[h]quinolin-2-yl)-9,9'-spirobifluorene; bipyridine derivatives such as 2,5-bis(6'-(2', 2''-bipyridyl))-1,1-dimethyl-3,4-diphenylsilole; terpyridine derivatives such as 1,3-bis(4'-(2,2':6'2''-terpyridinyl))benzene; and naphthylidine derivatives such as bis(1-naphthyl)-4-(1,8-naphthylidin-2-yl)phenylphosphine oxide are suitably used in view of an electron transporting ability. It is more preferable that such a derivative has a fused polycyclic aromatic skeleton because if so, then the glass transition temperature will increase and an effect of reducing the voltage of a light emitting device is great due to increased electron mobility. Moreover, considering the improvement in durable life of a device, the easiness of synthesis, and easy availability of raw materials, it is particularly preferable that the fused polycyclic aromatic skeleton is an anthracene skeleton, a pyrene skeleton, or a phenanthroline skeleton. While the electron transporting material may be used alone, two or more kinds of the electron transporting materials may be used in combination, or one or more kinds of other electron transporting materials may be used in a combination with the electron transporting material.

Preferable electron transporting materials are not particularly limited, and specific examples thereof include the following.

[Chemical Formula 30]

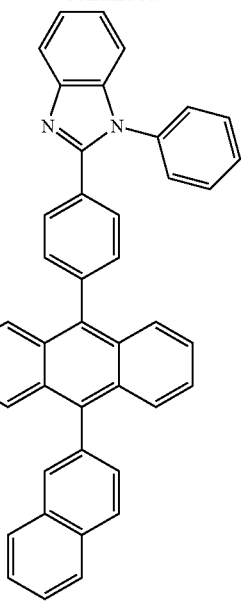

[Chemical Formula 30]

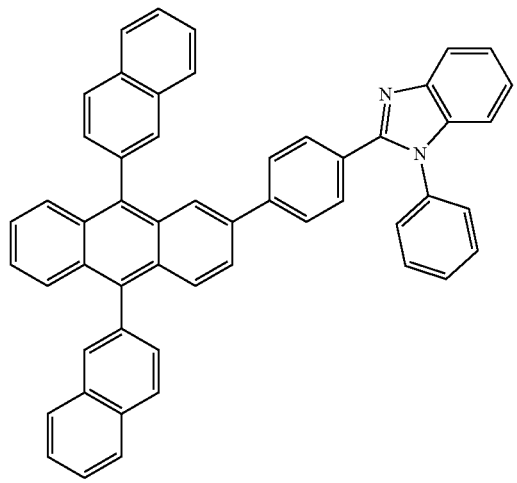

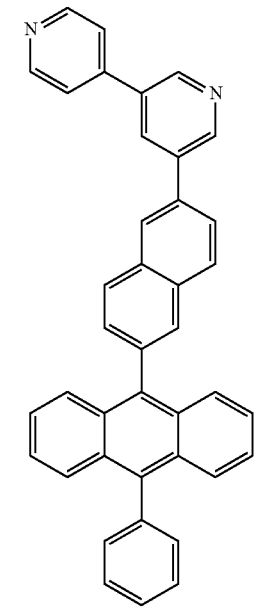

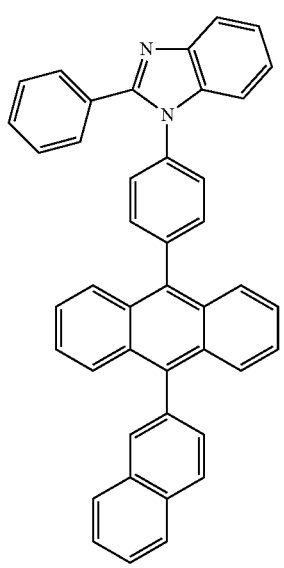

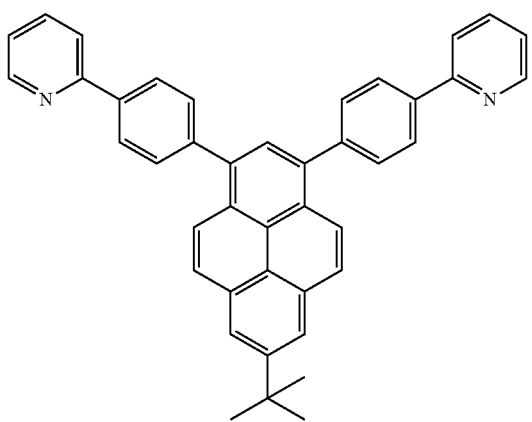

-continued

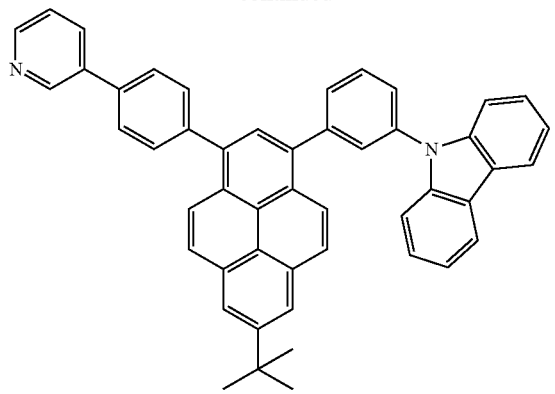
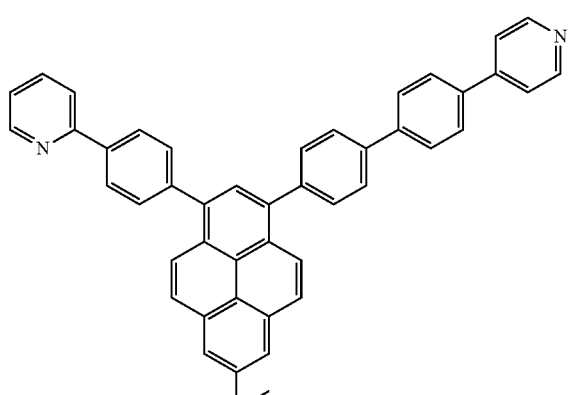
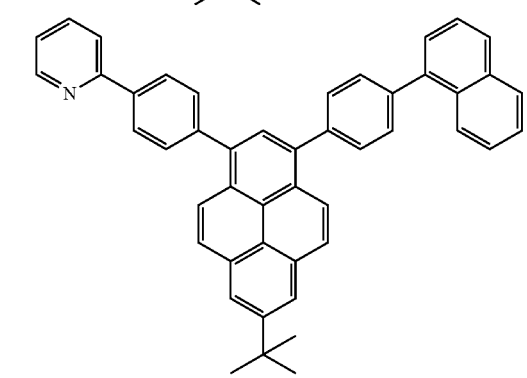
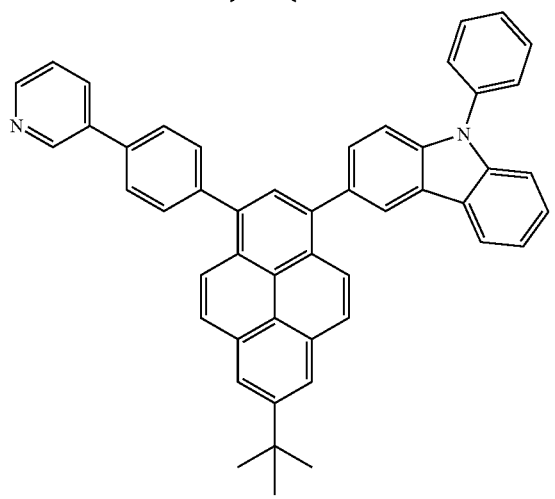

-continued

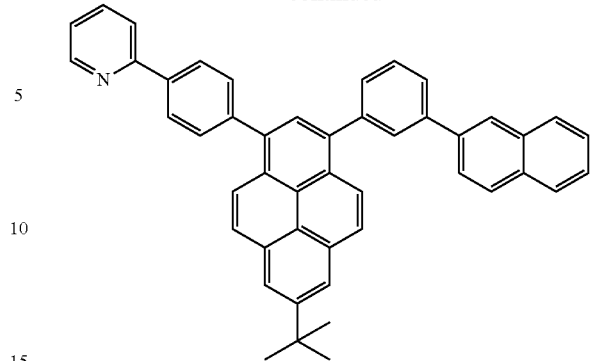
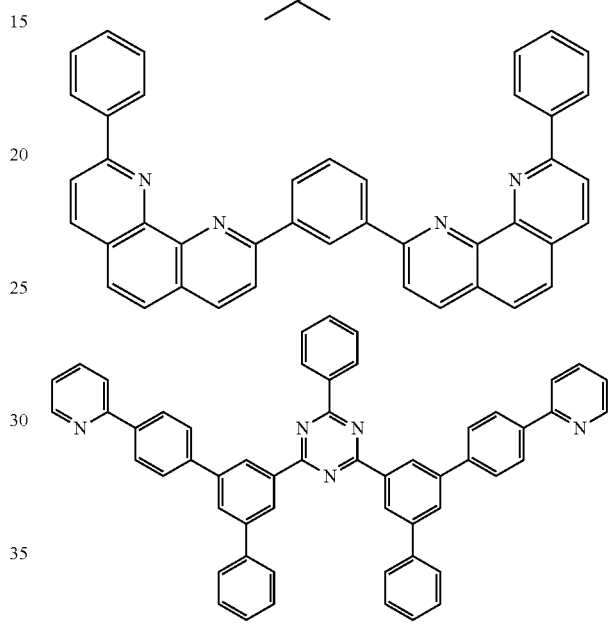

In addition thereto, electron transporting materials may also be used which are disclosed in WO 2004-63159 A, WO 2003-60956 A, Appl. Phys. Lett. 74, 865 (1999), Org. Electron. 4, 113 (2003), WO 2010-113743 A, WO 2010-1817 A and so on.

While the electron transporting material may be used alone, two or more kinds of the electron transporting materials may be used in combination, or one or more kinds of other electron transporting materials may be used in a combination with the electron transporting material. Moreover, a donor compound may be contained. The donor compound denotes a compound which makes easier electron injection into the electron transporting layer from the cathode or the electron injection layer and, further, improves the electric conductivity of the electron transporting layer, by improving an electron injection barrier.

Preferable examples of the donor compound include an alkali metal, an inorganic salt containing an alkali metal, a complex of an alkali metal and an organic substance, an alkaline earth metal, an inorganic salt containing an alkaline earth metal, or a complex of an alkaline earth metal and an organic substance. Examples of the preferable kind of the alkali metal and the alkaline earth metal include alkali metals such as lithium, sodium, potassium, rubidium, and cesium, and alkaline earth metals such as magnesium, calcium, cerium, and barium which have a low work function and have a great effect of improving electron transporting ability.

In addition, since deposition in vacuum is easy, and handling is excellent, the donor compound is preferably in the state of an inorganic salt or a complex with an organic substance rather than a metal single substance. Moreover, from the viewpoints of improvement in easiness in handling in the atmospheric air, and easiness in control of the concentration to be added, the donor compound is more preferably in the state of a complex with an organic substance. Examples of the inorganic salt include oxides such as LiO and $Li_2O$, nitrides, fluorides such as LiF, NaF, and KF, and carbonates such as $Li_2CO_3$, $Na_2CO_3$, $K_2CO_3$, $Rb_2CO_3$, and $Cs_2CO_3$. Preferable examples of the alkali metal or alkaline earth metal include lithium and cesium from the viewpoint that a great low-voltage driving effect can be obtained. In addition, preferable examples of the organic substance in complexes with an organic substance include quinolinol, benzoquinolinol, pyridylphenol, flavonol, hydroxyimidazopyridine, hydroxybenzazole, and hydroxytriazole. Especially, a complex of an alkali metal and an organic substance is preferred from the viewpoint that the effect of reducing the voltage of a light emitting device is greater, a complex of lithium and an organic substance is more preferred from the viewpoints of easiness in synthesis and thermal stability as well, and lithium quinolinol, which can be obtained relatively inexpensively, is particularly preferred.

The ionization potential of the electron transporting layer is not particularly limited, and is preferably 5.6 eV or more and 8.0 eV or less, and more preferably 6.0 eV or more and 7.5 eV or less.

Examples of a method of forming each of the aforementioned layers constituting the light emitting device include, but are not particularly limited to, resistance heating deposition, electron beam deposition, sputtering, a molecular lamination method, and a coating method, but usually, resistance heating deposition or electron beam deposition is preferable from the viewpoint of device property.

The thickness of the organic layer depends on the resistance value of an emissive substance and, therefore, it cannot be limited, but it is preferably 1 to 1000 nm. The film thickness of each of the emissive layer, the electron transporting layer and the hole transporting layer is preferably 1 nm or more and 200 nm or less, more preferably 5 nm or more and 100 nm or less.

The light emitting device of the present invention has a function of being able to convert electric energy into light. Herein, a direct current is mainly used as the electric energy, but a pulse current or an alternate current can also be used. A current value and a voltage value are not particularly limited, but when the power consumed and life of the device are considered, they should be selected so that the maximum luminance is obtained by energy as low as possible.

The light emitting device of the present invention is used suitably as a display that displays in a matrix and/or segment system.

In the matrix system, pixels for display are arranged two-dimensionally such as lattice-like arrangement or mosaic-like arrangement, and the collection of pixels displays letters and images. The shape and size of the pixel are determined depending on utility. For example, for displaying images and letters on personal computers, monitors and televisions, a square pixel being 300 μm or less at each side is usually used and, in the case of a large display such as a display panel, a pixel being millimeter order at each side is used. In the case of a monochromatic display, pixels having the same color may be arranged, and in the case of a color display, pixels having red, green and blue colors are arranged to perform display. In this case, typically, there are a delta type and a stripe type. A method of driving this matrix may be either a passive matrix driving method or an active matrix. The passive matrix driving has a simple structure, but when operation property is considered, the active matrix is more excellent in some cases, and it is necessary to use them properly depending on utility.

The segment system in the present invention is a system by which a pattern is formed so as to display predetermined information, and a region determined by arrangement of this pattern is made to emit light. Examples thereof include time and temperature displays in digital watches and thermometers, operating-state displays in audio equipment, IH cookers and so on, and panel displays of automobiles. The above-mentioned matrix display and segment display may exist together in the same panel.

The light emitting device of the present invention can also be preferably used as backlight of various instruments. Backlight is used mainly for the purpose of improving the visibility of display apparatuses which do not emit light by themselves, and is used in liquid crystal display equipment, clocks, audio equipment, automobile panels, display panels, signs, etc. In particular, the light emitting device of the present invention is preferably used in backlight for liquid crystal display apparatuses, inter alia, for personal computers which are studied to be thinned, and can provide backlight thinner and lighter than conventional products.

EXAMPLES

The present invention will be described by way of Examples, but the present invention is not limited thereto. In addition, the number of a compound in each of Examples described below indicates the number of the aforementioned compound.

Synthesis Example 1

Synthesis of Compound [6]

A mixed solution of 20.9 g of 3-bromocarbazole, 15.0 g of phenylcarbazole-3-boronic acid, 366 mg of palladium acetate, 300 mg of tris(2-methylphenyl)phosphine, 105 ml of a 2M aqueous potassium carbonate solution and 260 ml of dimethoxyethane was refluxed for 6 hours under a nitrogen flow. The solution was cooled to room temperature, and then extracted with 500 ml of toluene. The organic layer was washed with 100 ml of water twice, dried over magnesium sulfate, and then evaporated. The resultant concentrate was purified by silica gel column chromatography and then vacuum-dried to obtain 13.5 g of 9-phenyl-9H,9'H-3,3'-bicarbazole.

Next, a mixed solution of 20.0 g of 1,3-dibromo-5-chlorobenzene, 19.8 g of phenylboronic acid, 519 mg of bis(triphenylphosphine)palladium(II) dichloride, 217 ml of a 1.5 M aqueous sodium carbonate solution and 370 ml of dimethoxyethane was refluxed for 4 hours under a nitrogen flow. The solution was cooled to room temperature, and then extracted with 500 ml of toluene. The organic layer was washed with 250 ml of water three times, dried over magnesium sulfate, and then evaporated. The resultant concentrate was purified by silica gel column chromatography and then vacuum-dried to obtain 13.0 g of 5'-chloro-(1,1',3',1")terphenyl.

Next, a mixed solution of 10.0 g of 9-phenyl-9H,9'H-3,3'-bicarbazole, 7.8 g of 5'-chloro-(1,1',3',1")terphenyl, 423 mg of bis(dibenzylideneacetone)palladium, 191 mg of tri-t-butylphosphonium tetrafluoroborate, 3.29 g of sodium tert-butoxide and 245 ml of o-xylene was heated/stirred for 3 hours under reflux under a nitrogen flow. The solution was cooled to room temperature, and then extracted with 300 ml of toluene.

The organic layer was washed with 250 ml of water three times, dried over magnesium sulfate, and then evaporated. The resultant concentrate was purified by silica gel column chromatography and evaporated to obtain a solid, and the solid was vacuum-dried to obtain 12.1 g of a white solid.

$^1$H-NMR analytical results of the resulting powder are as follows, and it was confirmed that the resulting white solid was a compound [6].

$^1$H-NMR (CDCl$_3$ (d=ppm)): 7.42-7.72 (m, 20H), 7.73-7.85 (m, 8H), 7.93-7.94 (m, 1H), 8.47 (t, 1H), 8.48-8.49 (m, 2H).

The compound [6] was used as a light emitting device material after sublimation purification was performed at about 330° C. under a pressure of 1×10$^{-3}$ Pa using an oil diffusion pump. The HPLC purity (area % at a measurement wavelength of 254 nm) was 99.7% before sublimation purification, and 99.9% after sublimation purification.

Synthesis Example 2

Synthesis of Compound [156]

A mixed solution of 20 g of 2-bromonitrobenzene, 17 g of 4-chlorophenylboronic acid, 45 g of tripotassium phosphate, 6.9 g of tetrabutylammonium bromide, 480 mg of palladium acetate and 500 ml of dimethylformamide was heated/stirred at 130° C. for 5 hours under a nitrogen flow. The solution was cooled to room temperature, then poured into 100 ml of water, and extracted with 150 ml of toluene. The organic layer was washed with 100 ml of water three times, dried over magnesium sulfate, and then evaporated. The concentrate was purified by silica gel column chromatography and vacuum-dried to obtain 22 g of 2-(4-chlorophenyl)nitrobenzene.

Next, a mixed solution of 22 g of 2-(4-chlorophenyl)nitrobenzene, 61 g of triphenylphosphine and 190 ml of o-dichlorobenzene was refluxed for 6 hours under a nitrogen flow. The solution was cooled to room temperature, o-dichlorobenzene was then distilled away under reduced pressure, and the concentrate was purified by silica gel column chromatography, and vacuum-dried to obtain 17.7 g of 2-chloro-9H-carbazole.

Next, a mixed solution of 17.7 g of 2-chloro-9H-carbazole, 22 g of iodobenzene, 20 g of a copper powder, 43 g of potassium carbonate and 200 ml of dimethylformamide was heated/stirred at 140° C. for 16 hours under a nitrogen flow. The solution was cooled to room temperature, 50 ml of ethyl acetate was added, and the mixture was filtered with Celite. To the resultant filtrate was added a saturated aqueous ammonium chloride solution, and the mixture was stirred for a while, and then extracted with ethyl acetate and hexane. The extract was dried over magnesium sulfate, and then evaporated. The concentrate was purified by silica gel column chromatography and vacuum-dried to obtain 14 g of 2-chloro-9-phenyl-9H-carbazole.

Next, a mixed solution of 14 g of 2-chloro-9-phenyl-9H-carbazole, 15.4 g of bis(pinacolate)diboron, 14.8 g of potassium acetate, 100 ml of dioxane, 0.58 g of tris(dibenzylideneacetone)dipalladium(0) and 961 mg of 2-dicyclohexylphosphino-2'4'6'-triisopropylbiphenyl was refluxed for 7 hours under a nitrogen flow. The solution was cooled to room temperature, and then extracted with toluene. The organic layer was washed with water three times, dried over magnesium sulfate, and then evaporated. The resultant concentrate was purified by silica gel column chromatography and then vacuum-dried to obtain 16 g of 9-phenyl-2-(4,4,5,5-tetramethyl-1,3,2-dioxaborolane-2-yl)-9H-carbazole.

Next, a mixed solution of 4.0 g of 3-bromocarbazole, 6.6 g of 9-phenyl-2-(4,4,5,5-tetramethyl-1,3,2-dioxaborolane-2-yl)-9H-carbazole, 18 ml of a 2M aqueous potassium carbonate solution, 80 ml of 1,2-dimethoxyethane, 72 mg of palladium acetate and 243 mg of tris(2-methylphenyl)phosphine was refluxed for 6 hours under a nitrogen flow. The solution was cooled to room temperature, and then extracted with toluene. The organic layer was washed with water twice, dried over magnesium sulfate, and then evaporated. The resultant concentrate was purified by silica gel column chromatography and then vacuum-dried to obtain 5.2 g of 9-phenyl-9H,9'H-2,3'-bicarbazole.

Next, a mixed solution of 1.5 g of 9-phenyl-9H,9'H-2,3'-bicarbazole, 1.1 g of 5'-chloro-(1,1',3',1")terphenyl, 65 mg of bis(dibenzylideneacetone)palladium, 29 mg of tri-t-butylphosphonium tetrafluoroborate, 564 mg of sodium tert-butoxide and 37 ml of o-xylene was heated/stirred for 6 hours under reflux under a nitrogen flow. The solution was cooled to room temperature, and then extracted with 100 ml toluene. The organic layer was washed with 50 ml of water three times, dried over magnesium sulfate, and then evaporated. The resultant concentrate was purified by silica gel column chromatography and evaporated to obtain a solid, and the solid was vacuum-dried to obtain 2.0 g of a white solid.

$^1$H-NMR analytical results of the resulting powder are as follows, and it was confirmed that the resulting white solid was a compound [156].

$^1$H-NMR (CDCl$_3$ (d=ppm)): 7.41-7.73 (m, 25H), 7.80-7.81 (d, 2H), 7.91-7.93 (t, 1H), 8.17-8.25 (m, 3H), 8.40-8.41 (m, 1H).

The compound [156] was used as a light emitting device material after sublimation purification was performed at about 330° C. under a pressure of 1×10$^{-3}$ Pa using an oil diffusion pump. The HPLC purity (area % at a measurement wavelength of 254 nm) was 99.8% before sublimation purification, and 99.9% after sublimation purification.

Synthesis Example 3

Synthesis of Compound [176]

A mixed solution of 20.9 g of 3-bromocarbazole, 15.0 g of 9-phenylcarbazole-3-boronic acid, 366 mg of palladium acetate, 300 mg of tris(2-methylphenyl)phosphine, 105 ml of a 2M aqueous potassium carbonate solution and 260 ml of dimethoxyethane was refluxed for 6 hours under a nitrogen flow. The solution was cooled to room temperature, and then extracted with 500 ml of tetrahydrofuran. The organic layer was washed with 100 ml of a saturated saline solution twice, dried over magnesium sulfate, and then evaporated. The resultant concentrate was purified by o-xylene recrystallization and then vacuum-dried to obtain 13.5 g of 9-phenyl-9H,9'H-3,3'-bicarbazole.

Next, a mixed solution of 10.0 g of 1,3-dibromo-5-chlorobenzene, 9.9 g of phenyl-d5-boronic acid, 130 mg of bis(triphenylphosphine)palladium(II) dichloride, 78 ml of a 2.0 M aqueous sodium carbonate solution and 185 ml of dimethoxyethane was refluxed for 4 hours under a nitrogen flow. The solution was cooled to room temperature, and then extracted with 300 ml of toluene. The organic layer was washed with 200 ml of water three times, dried over magnesium sulfate, and then evaporated. The resultant concentrate was purified by silica gel column chromatography and then vacuum-dried to obtain 8.5 g of an intermediate.

Next, a mixed solution of 5.0 g of 9-phenyl-9H,9'H-3,3'-bicarbazole, 4.0 g of the intermediate, 70 mg of bis(dibenzylideneacetone)palladium, 86 mg of di-t-butyl(2,2-diphenyl-1-methyl-1-cyclopropyl)phosphine, 1.65 g of sodium tert-butoxide and 61 ml of o-xylene was heated/stirred for 2 hours under reflux under a nitrogen flow. The solution was cooled to room temperature, and then extracted with 300 ml of toluene. The organic layer was washed with 250 ml of water three times, dried over magnesium sulfate, and then evaporated. The resultant concentrate was purified by silica gel column chromatography and evaporated to obtain a solid, and the solid was vacuum-dried to obtain 6.1 g of a white solid.

$^1$H-NMR analytical results of the resulting powder are as follows, and it was confirmed that the resulting white solid was a compound [176].

$^1$H-NMR (CDCl$_3$ (d=ppm)): 7.30-7.67 (m, 13H), 7.78-7.85 (m, 4H), 7.93-7.94 (t, 1H), 8.24-8.29 (t, 2H), 8.47-8.49 (m, 2H).

The compound [176] was used as a light emitting device material after sublimation purification was performed at about 330° C. under a pressure of 1×10 Pa using an oil diffusion pump. The HPLC purity (area % at a measurement wavelength of 254 nm) was 99.6% before sublimation purification, and 99.9% after sublimation purification.

Synthesis Example 4

Synthesis of Compound [170]

A white solid was obtained by performing synthesis in the same manner as in Synthesis Example 1 except that 4-methylphenylboronic acid was used in place of phenylboronic acid. $^1$H-NMR analytical results of the resulting powder are as follows, and it was confirmed that the resulting white solid was a compound [170].

$^1$H-NMR (CDCl$_3$ (d=ppm)): 2.43 (s, 6H), 7.29-8.23 (m, 26H), 8.25-8.46 (m, 2H), 8.47 (s, 2H).

The compound [170] was used as a light emitting device material after sublimation purification was performed at about 340° C. under a pressure of 1×10$^{-3}$ Pa using an oil diffusion pump. The HPLC purity (area % at a measurement wavelength of 254 nm) was 99.7% before sublimation purification, and 99.9% after sublimation purification.

Synthesis Example 5

Synthesis of Compound [193]

A white solid was obtained by performing synthesis in the same manner as in Synthesis Example 1 except that 4-fluorophenylboronic acid was used in place of phenylboronic acid. $^1$H-NMR analytical results of the resulting powder are as follows, and it was confirmed that the resulting white solid was a compound [193].

$^1$H-NMR (CDCl$_3$ (d=ppm)): 7.18-7.21 (m, 4H), 7.32-7.37 (m, 2H), 7.44-7.56 (m, 6H), 7.61-7.77 (m, 9H), 7.77-8.82 (m, 5H), 8.24-8.28 (m, 2H), 8.47-8.49 (m, 2H).

The compound [193] was used as a light emitting device material after sublimation purification was performed at about 340° C. under a pressure of 1×10$^{-3}$ Pa using an oil diffusion pump. The HPLC purity (area % at a measurement wavelength of 254 nm) was 99.7% before sublimation purification, and 99.9% after sublimation purification.

Synthesis Example 6

Synthesis of Compound [198]

A mixed solution of 3.2 g of carbazole, 6.0 g of 5'-chloro-(1,1':3',1")terphenyl, 109 mg of bis(dibenzylideneacetone) palladium, 134 mg of di-t-butyl(2,2-diphenyl-1-methyl-1-cyclopropyl)phosphine, 2.5 g of sodium tert-butoxide and 90 ml of o-xylene was heated/stirred for 2 hours under reflux under a nitrogen flow. The solution was cooled to room temperature, and then extracted with 100 ml of toluene. The organic layer was washed with 50 ml of water three times, dried over magnesium sulfate, and then evaporated. The resultant concentrate was purified by silica gel column chromatography and then vacuum-dried to obtain 6.9 g of 9-([1,1':3',1"-terphenyl]-5'-yl)-9H-carbazole.

Next, a mixed solution of 6.9 g of 9-([1,1':3',1"-terphenyl]-5'-yl)-9H-carbazole, 3.1 g of N-bromosuccinimide and 174 ml of degassed dimethylformamide was heated/stirred at 60° C. for 3 hours under a nitrogen flow. The solution was cooled to room temperature, and then extracted with 100 ml of toluene. The organic layer was washed with 50 ml of water three times, dried over magnesium sulfate, and then evaporated. 7.5 g of the resultant concentrate (9-([1,1':3',1"-terphenyl]-5'-yl)-3-bromo-9H-carbazole) was vacuum-dried and then used for the next reaction without being purified.

Next, a mixed solution of 3 g of 9-([1,1':3',1"-terphenyl]-5'-yl)-3-bromo-9H-carbazole, 1.16 g of carbazole, 36 mg of bis(dibenzylideneacetone)palladium, 44 mg of di-t-butyl(2,2-diphenyl-1-methyl-1-cyclopropyl)phosphine, 848 mg of sodium tert-butoxide and 32 ml of o-xylene was heated/stirred for 6 hours under reflux under a nitrogen flow. The solution was cooled to room temperature, and then extracted with 100 ml toluene. The organic layer was washed with 50 ml of water three times, dried over magnesium sulfate, and then evaporated. The resultant concentrate was purified by silica gel column chromatography and evaporated to obtain a solid, and the solid was vacuum-dried to obtain 1.5 g of a white solid.

$^1$H-NMR analytical results of the resulting powder are as follows, and it was confirmed that the resulting white solid was a compound [198].

$^1$H-NMR (CDCl$_3$ (d=ppm)): 7.12-7.24 (m, 2H), 7.25-7.61 (m, 15H), 7.70-7.76 (m, 4H), 7.85-7.86 (m, 2H), 7.95-7.97 (m, 1H), 8.12-8.20 (m, 3H), 8.30-8.31 (d, 1H).

The compound [198] was used as a light emitting device material after sublimation purification was performed at about 300° C. under a pressure of 1×10$^{-3}$ Pa using an oil diffusion pump. The HPLC purity (area % at a measurement wavelength of 254 nm) was 99.7% before sublimation purification, and 99.9% after sublimation purification.

Example 1

A glass substrate with an ITO transparent electroconductive film deposited thereon in a thickness of 50 nm (manufactured by GEOMATEC Co., Ltd., 11Ω/□, sputtered product) was cut into 38×46 mm, and etched. The resulting substrate was ultrasonically washed with "SEMICOCLEAN 56" (trade name, manufactured by Furuuchi Chemical Corporation) for 15 minutes, and then washed with ultrapure water. This substrate was treated with UV-ozone for 1 hour immediately before preparation of a device, and placed in a vacuum deposition apparatus, and the air was evacuated until the degree of vacuum in the apparatus was 5×10$^{-4}$ Pa or lower. By a resistance heating method, HI-1 was deposited as a hole injection layer in a thickness of 10 nm. Next, HT-1 was deposited as a first hole transporting layer in a thickness of 110 nm. Next, a compound [6] was deposited as a second hole transporting layer in a thickness of 10 nm. Next, a compound H-1 and a compound D-1 were used as a host material and as a dopant material, respectively, and were deposited as an emissive layer in a thickness of 40 nm so that the doping concentration of the dopant material was 5% by weight. Next, a compound E-1 was laminated as an electron transporting layer in a thickness of 20 nm.

Next, lithium fluoride was deposited in a thickness of 0.5 nm and aluminum was deposited in a thickness of 60 nm to form a cathode, so that a 5×5 mm square device was prepared. The film thickness referred to herein was an indicated value on a crystal oscillation film thickness monitor. When this light emitting device was direct-current driven at 10 mA/cm$^2$, blue light emission with a luminance efficiency of 5.2 lm/W was obtained. When this light emitting device was continuously driven at a direct current of 10 mA/cm$^2$, the luminance decreased by half after 1600 hours. Compounds HI-1, HT-1, H-1, D-1, and E-1 are the compounds shown below.

[Chemical Formula 31]

[Chemical Formula 31]

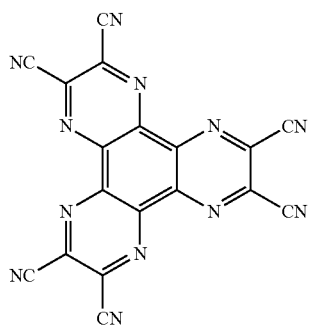

HI-1

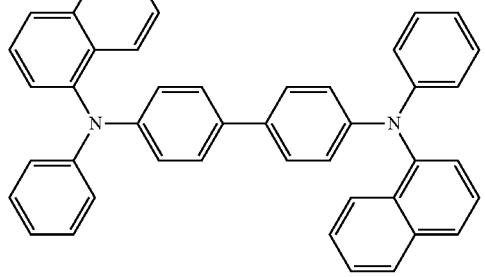

HT-1

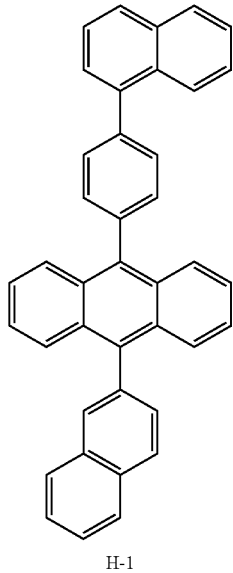

H-1

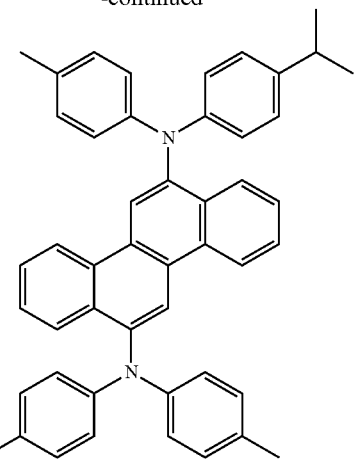

D-1

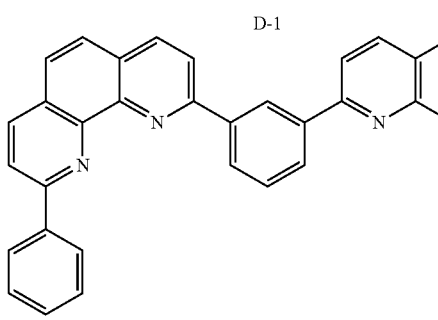

E-1

Examples 2 to 4

Light emitting devices were prepared in the same manner as in Example 1 except that materials described in Table 1 were used as a second hole transporting layer. The results of Examples are shown in Table 1.

Comparative Examples 1 to 6

In the same manner as in Example 1 except that materials described in Table 1 were used as a second hole transporting layer, light emitting devices were prepared and evaluated. The results are shown in Table 1. HT-2 to HT-7 are the compounds shown below.

[Chemical Formula 32]

[Chemical Formula 32]

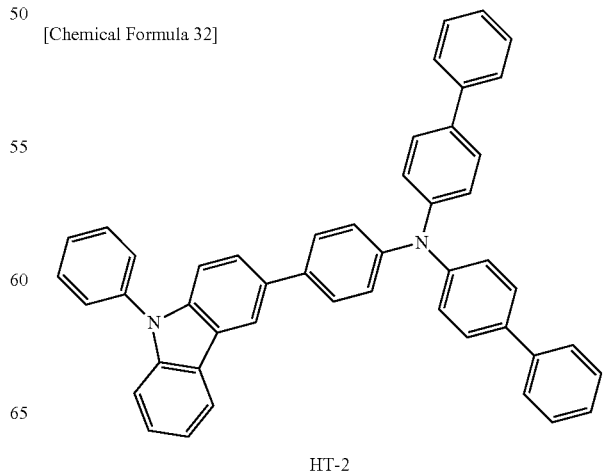

HT-2

-continued

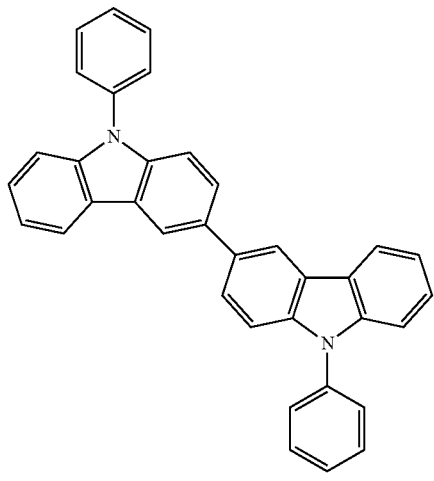
HT-3

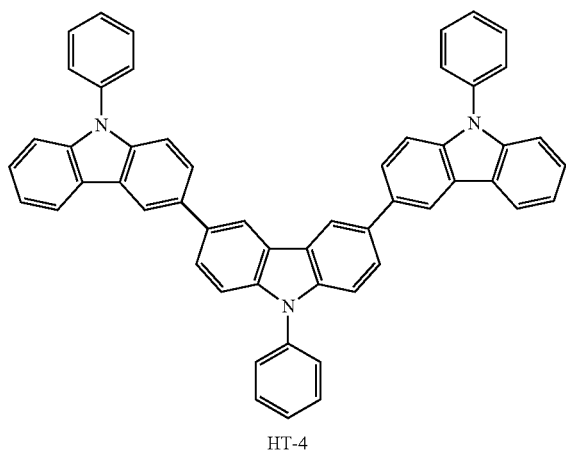
HT-4

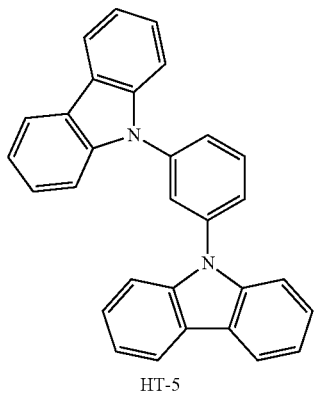
HT-5

-continued

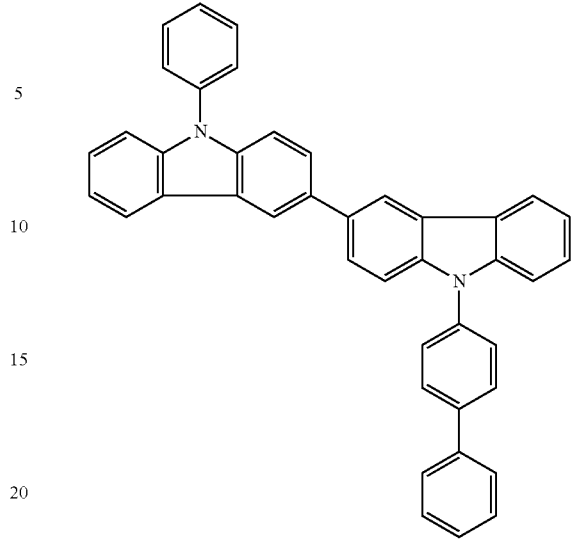
HT-6

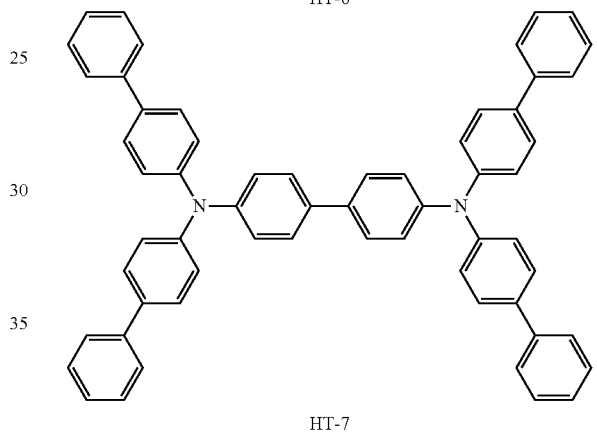
HT-7

Example 5

A glass substrate with an ITO transparent electroconductive film deposited thereon in a thickness of 50 nm (manufactured by GEOMATEC Co., Ltd., 11Ω/☐, sputtered product) was cut into 38×46 mm, and etched. The resulting substrate was ultrasonically washed with "SEMICOCLEAN 56" (trade name, manufactured by Furuuchi Chemical Corporation) for 15 minutes, and then washed with ultrapure water. This substrate was treated with UV-ozone for 1 hour immediately before preparation of a device, and placed in a vacuum deposition apparatus, and the air was evacuated until the degree of vacuum in the apparatus was $5\times10^{-4}$ Pa or lower. By a resistance heating method, HI-1 was deposited as a hole injection layer in a thickness of 10 nm. Next, HT-1 was deposited as a first hole transporting layer in a thickness of 110 nm. Next, a compound [6] was deposited as a second hole transporting layer in a thickness of 10 nm. Then, a compound H-2 and a compound D-2 were used as a host material and as a dopant material, respectively, and were deposited as an emissive layer in a thickness of 40 nm so that the doping concentration of the dopant material was 10% by weight. Next, a layer formed by mixing an organic compound (E-2) and a donor compound (lithium quinolinol) at a deposition speed ratio of 1:1 (=0.05 nm/s:0.05 nm/s) was laminated as an electron transporting layer in a thickness of 10 nm.

Next, lithium quinolinol was deposited in a thickness of 1 nm, and co-deposited film of magnesium and silver was deposited in a thickness of 100 nm at a deposition speed ratio of magnesium:silver=10:1 (=0.5 nm/s:0.05 nm/s) to form a cathode, so that a 5×5 mm square device was prepared. The film thickness referred to herein was an indicated value on a crystal oscillation film thickness monitor. When this light emitting device was direct-current driven at 10 mA/cm$^2$, green light emission with a luminance efficiency of 14.0 lm/W was obtained. When this light emitting device was continuously driven at a direct current of 10 mA/cm$^2$, the luminance decreased by half after 1500 hours. H-2, D-2 and E-2 are the compounds shown below.

[Chemical Formula 33]

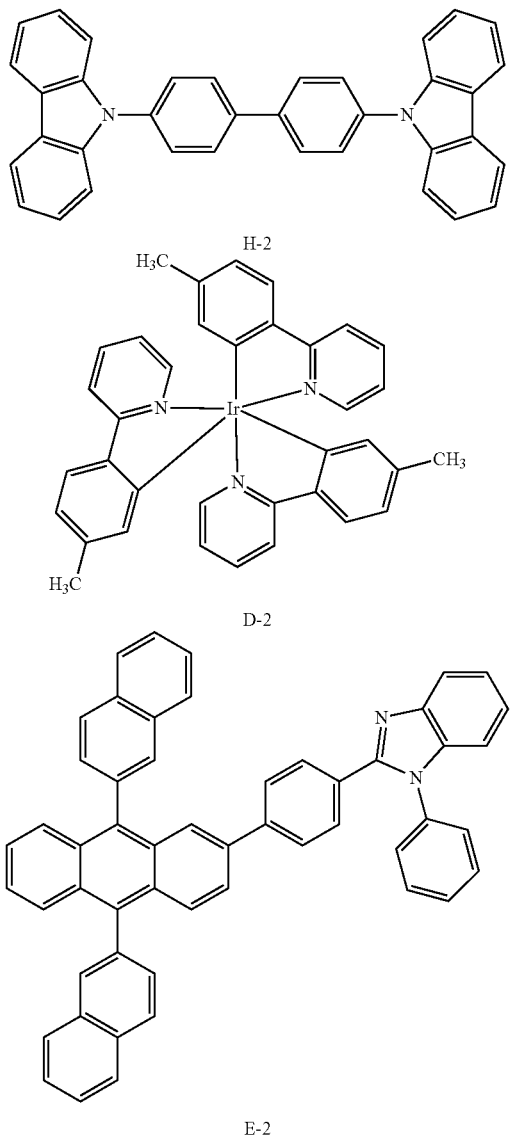

[Chemical Formula 33]

H-2

D-2

E-2

Examples 6 to 8

In the same manner as in Example 5 except that materials described in Table 2 were used as a second hole transporting layer, a host material and a dopant material, light emitting devices were prepared and evaluated. The results are shown in Table 2.

Comparative Examples 7 to 11

In the same manner as in Example 5 except that compounds described in Table 2 were used as a second hole transporting layer, a host material and a dopant material, light emitting devices were prepared and evaluated. The results are shown in Table 2.

Example 9

A glass substrate with an ITO transparent electroconductive film deposited thereon in a thickness of 50 nm (manufactured by GEOMATEC Co., Ltd., 11Ω/□, sputtered product) was cut into 38×46 mm, and etched. The resulting substrate was ultrasonically washed with "SEMICOCLEAN 56" (trade name, manufactured by Furuuchi Chemical Corporation) for 15 minutes, and then washed with ultrapure water. This substrate was treated with UV-ozone for 1 hour immediately before preparation of a device, and placed in a vacuum deposition apparatus, and the air was evacuated until the degree of vacuum in the apparatus was 5×10$^{-4}$ Pa or lower. By a resistance heating method, HI-1 was deposited as a hole injection layer in a thickness of 10 nm. Next, HT-1 was deposited as a hole transporting layer in a thickness of 125 nm. Then, a compound [6] and a compound D-2 were used as a host material and as a dopant material, respectively, and were deposited as an emissive layer in a thickness of 40 nm so that the doping concentration of the dopant material was 10% by weight. Next, a compound E-1 was laminated as an electron transporting layer in a thickness of 20 nm.

Next, lithium fluoride was deposited in a thickness of 0.5 nm and aluminum was deposited in a thickness of 60 nm to form a cathode, so that a 5×5 mm square device was prepared. The film thickness referred to herein was an indicated value on a crystal oscillation film thickness monitor. When this light emitting device was direct-current driven at 10 mA/cm$^2$, green light emission with a luminance efficiency of 19.0 lm/W was obtained. When this light emitting device was continuously driven at a direct current of 10 mA/cm$^2$, the luminance decreased by half after 1600 hours.

Examples 10 to 11

In the same manner as in Example 9 except that materials described in Table 3 were used as a hole transporting layer, a host material and a dopant material, light emitting devices were prepared and evaluated. The results are shown in Table 3.

Comparative Examples 12 to 18

In the same manner as in Example 9 except that compounds described in Table 3 were used as a hole transporting layer, a host material and a dopant material, light emitting devices were prepared and evaluated. The results are shown in Table 3. Compounds H-3, H-4, H-5 and H-6 are compounds shown below.

[Chemical Formula 34]

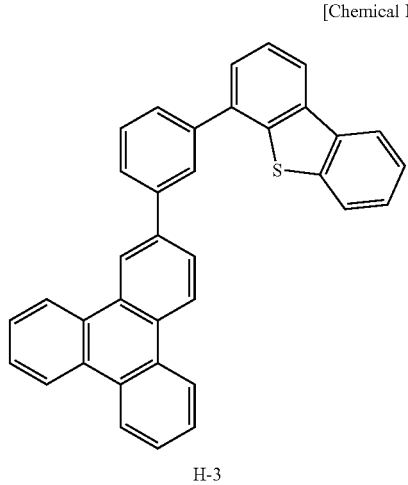

H-3

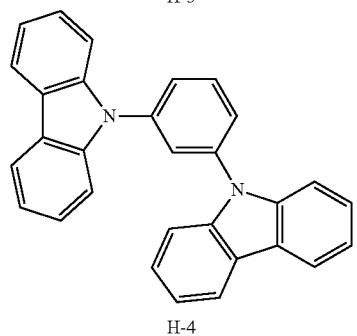

H-4

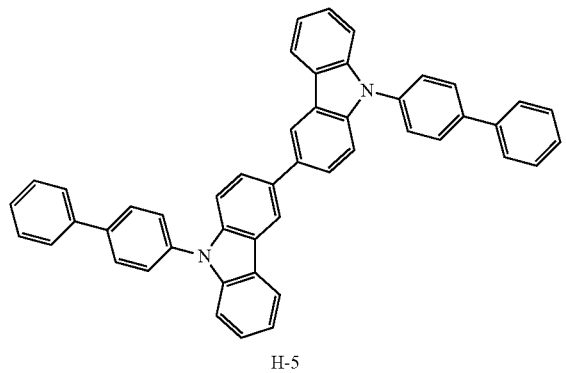

H-5

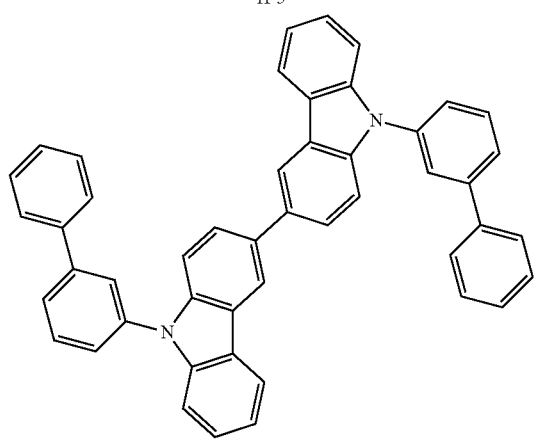

H-6

Example 12

A glass substrate with an ITO transparent electroconductive film deposited thereon in a thickness of 50 nm (manufactured by GEOMATEC Co., Ltd., 11Ω/□, sputtered product) was cut into 38×46 mm, and etched. The resulting substrate was ultrasonically washed with "SEMICOCLEAN 56" (trade name, manufactured by Furuuchi Chemical Corporation) for 15 minutes, and then washed with ultrapure water. This substrate was treated with UV-ozone for 1 hour immediately before preparation of a device, and placed in a vacuum deposition apparatus, and the air was evacuated until the degree of vacuum in the apparatus was $5 \times 10^{-4}$ Pa or lower. By a resistance heating method, HI-1 was deposited as a hole injection layer in a thickness of 10 nm. Next, HT-7 was deposited as a first hole transporting layer in a thickness of 90 nm. Next, a compound [6] was deposited as a second hole transporting layer in a thickness of 30 nm. Next, a compound H-7 and a compound D-3 were used as a host material and as a dopant material, respectively, and were deposited as an emissive layer in a thickness of 30 nm so that the doping concentration of the dopant material was 4% by weight. Next, a compound E-1 was laminated as an electron transporting layer in a thickness of 35 nm.

Next, lithium fluoride was deposited in a thickness of 0.5 nm and aluminum was deposited in a thickness of 60 nm to form a cathode, so that a 5×5 mm square device was prepared. The film thickness referred to herein was an indicated value on a crystal oscillation film thickness monitor. When this light emitting device was direct-current driven at 10 mA/cm², red light emission with a luminance efficiency of 10.3 lm/W was obtained. When this light emitting device was continuously driven at a direct current of 10 mA/cm², the luminance decreased by half after 1500 hours. Compounds H-7 and D-3 are compounds shown below.

[Chemical Formula 35]

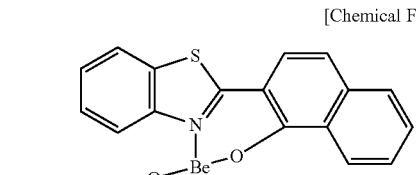

H-7

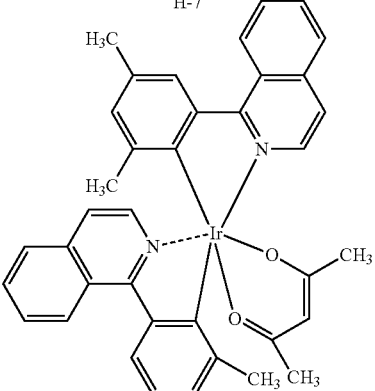

D-3

Examples 13 to 22

In the same manner as in Example 12 except that materials described in Table 4 were used as a second hole transporting layer, a host material and a dopant material, light emitting devices were prepared and evaluated. The results are shown in Table 4.

Comparative Examples 19 to 22

In the same manner as in Example 12 except that compounds described in Table 4 were used as a second hole transporting layer, a host material and a dopant material, light emitting devices were prepared and evaluated. The results are shown in Table 4.

Example 23

A glass substrate with an ITO transparent electroconductive film deposited thereon in a thickness of 50 nm (manufactured by GEOMATEC Co., Ltd., 11Ω/□, sputtered product) was cut into 38×46 mm, and etched. The resulting substrate was ultrasonically washed with "SEMICOCLEAN 56" (trade name, manufactured by Furuuchi Chemical Corporation) for 15 minutes, and then washed with ultrapure water. This substrate was treated with UV-ozone for 1 hour immediately before preparation of a device, and placed in a vacuum deposition apparatus, and the air was evacuated until the degree of vacuum in the apparatus was $5\times10^{-4}$ Pa or lower. By a resistance heating method, HI-1 was deposited as a hole injection layer in a thickness of 10 nm. Next, HT-8 was deposited as a first hole transporting layer in a thickness of 80 nm. Next, a compound [6] was deposited as a second hole transporting layer in a thickness of 10 nm. Next, a compound H-8 and a compound D-4 were used as a host material and as a dopant material, respectively, and were deposited as an emissive layer in a thickness of 30 nm so that the doping concentration of the dopant material was 10% by weight. Next, a layer formed by mixing an organic compound (E-2) and a donor compound (Liq: lithium quinolinol) at a deposition speed ratio of 1:1 (=0.05 nm/s:0.05 nm/s) was laminated as an electron transporting layer in a thickness of 35 nm.

Next, lithium quinolinol was deposited in a thickness of 1 nm, and co-deposited film of magnesium and silver was deposited in a thickness of 100 nm at a deposition speed ratio of magnesium:silver=10:1 (=0.5 nm/s:0.05 nm/s) to form a cathode, so that a 5×5 mm square device was prepared. The film thickness referred to herein was an indicated value on a crystal oscillation film thickness monitor. When this light emitting device was direct-current driven at 10 mA/cm$^2$, green light emission with a luminance efficiency of 50.0 lm/W was obtained. When this light emitting device was continuously driven at a direct current of 10 mA/cm$^2$, the luminance decreased by half after 5500 hours. HT-8, H-8 and D-4 are the compounds shown below.

[Chemical Formula 36]

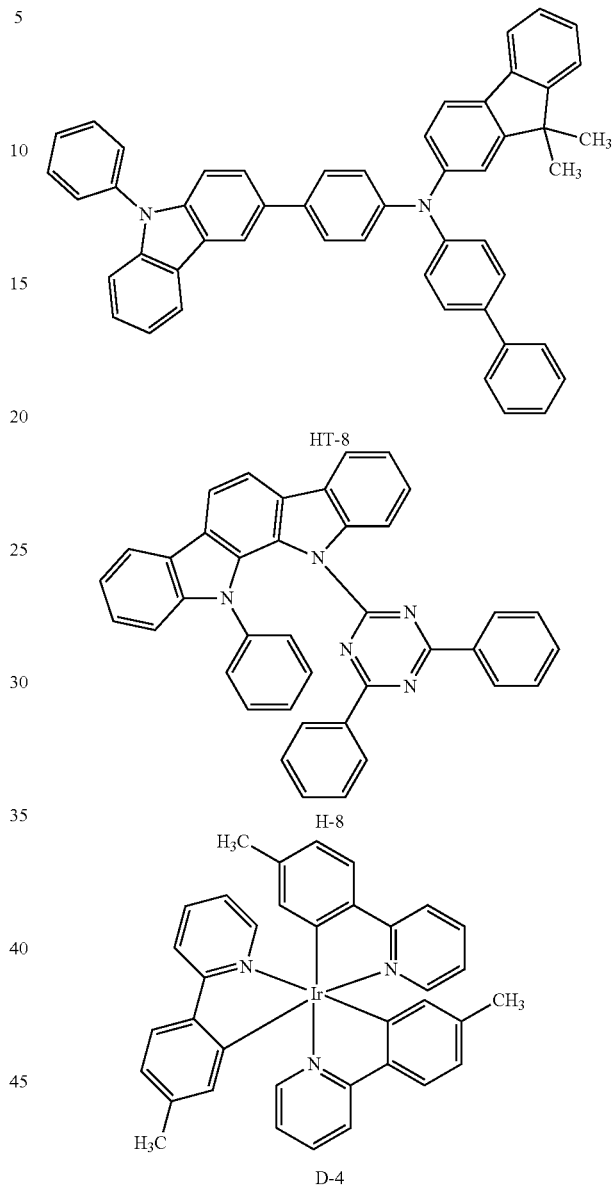

Examples 24 to 25

In the same manner as in Example 23 except that materials described in Table 5 were used as a second hole transporting layer, light emitting devices were prepared and evaluated. The results are shown in Table 5.

Comparative Examples 23 to 27

In the same manner as in Example 23 except that compounds described in Table 5 were used as a second hole transporting layer, light emitting devices were prepared and evaluated. The results are shown in Table 5.

Examples 26 to 28

Light emitting devices were prepared in the same manner as in Example 23 except that a compound HT-8 and a compound HI-2 were used in place of the compound HI-1, and were deposited as a hole injection layer in a thickness of 10 nm so that the doping concentration of the compound HI-2 was 5% by weight with respect to the compound HT-8. The results are shown in Table 5. HI-2 is the compound shown below.

[Chemical Formula 37]

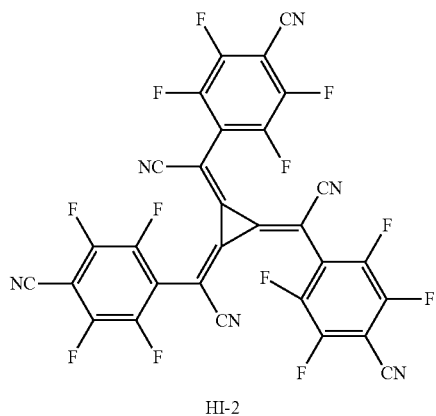

HI-2

Examples 29 to 31

Light emitting devices were prepared in the same manner as in Examples 26 to 28 except that as a host material, a mixed host of a compound H-8 and a compound H-9 (formed by depositing a co-deposited film of the compound H-8 and the compound H-9 at a deposition speed ratio of 1:1, and further depositing a dopant) was used in place of the compound H-8. The results are shown in Table 5. H-9 is the compound shown below.

[Chemical Formula 38]

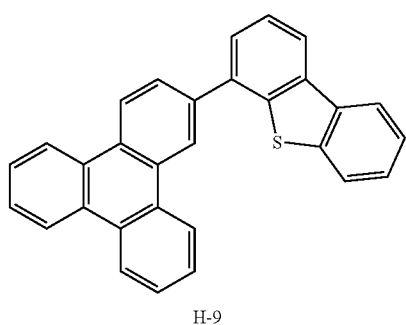

H-9

Examples 32 to 34

Light emitting devices were prepared in the same manner as in Examples 23 to 25 except that as a hole injection layer, a compound HI-3 was used in place of the compound HI-1. The results are shown in Table 5. HI-3 is the compound shown below.

[Chemical Formula 39]

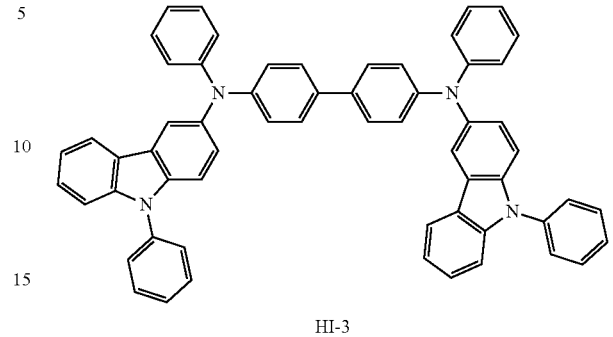

HI-3

Examples 35 to 37

Light emitting devices were prepared in the same manner as in Example 26 except that as an electron transporting layer, materials described in Table 5 were used in place of the layer formed by mixing a compound E-2 and a donor compound (Liq: lithium quinolinol). The results are shown in Table 5. E-3 to E-5 are the compounds shown below.

Comparative Examples 28 and 29

In the same manner as in Example 35 except that compounds described in Table 5 were used as an electron transporting layer, light emitting devices were prepared and evaluated. The results are shown in Table 9. E-6 and E-7 are the compounds shown below.

[Chemical Formula 40]

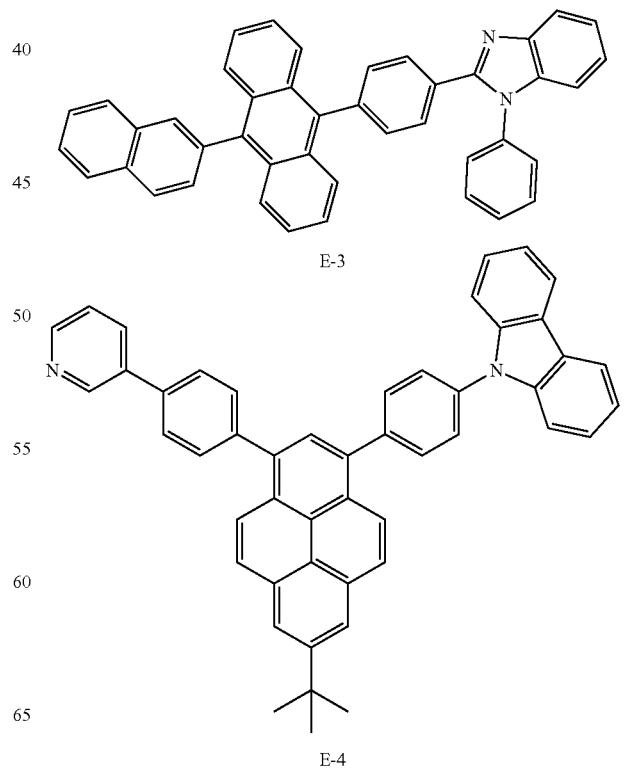

-continued

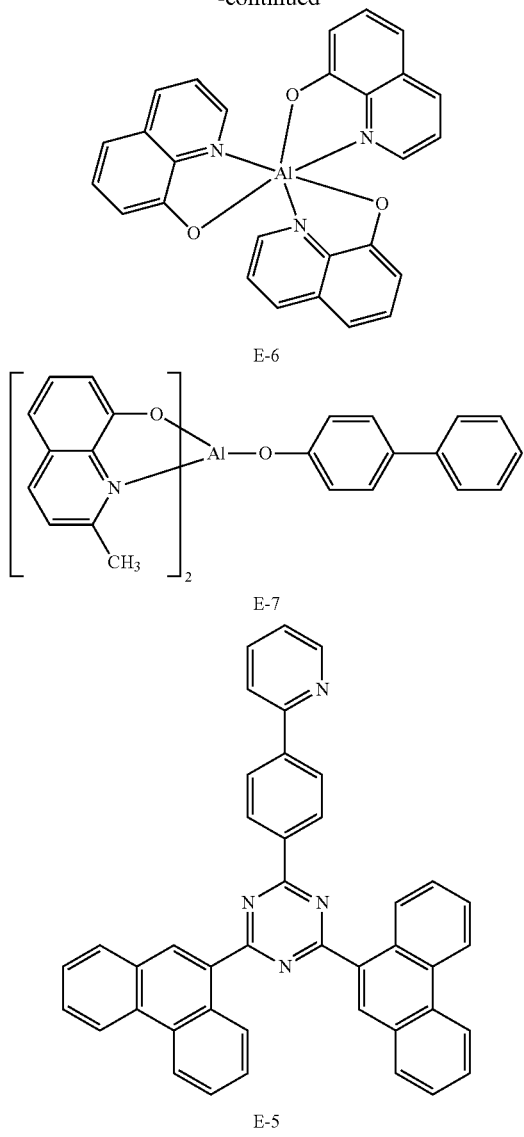

E-6

E-7

E-5

Example 38

A light emitting device was prepared in the same manner as in Example 26 except that as an electron transporting layer, a compound E-2 and a compound E-1 were laminated in a thickness of 35 nm at a film thickness ratio of 1:1 and used in place of the layer formed by mixing a compound E-2 and a donor compound (Liq: lithium quinolinol). The results are shown in Table 5.

Example 39

A light emitting device was prepared in the same manner as in Example 26 except that as an electron transporting layer, a compound E-3 and a compound E-1 were laminated in a thickness of 35 nm at a film thickness ratio of 1:1 and used in place of the layer formed by mixing a compound E-2 and a donor compound (Liq: lithium quinolinol). The results are shown in Table 5.

Example 40

A light emitting device was prepared in the same manner as in Example 26 except that as an electron transporting layer, a compound E-4 and a compound E-1 were laminated in a thickness of 35 nm at a film thickness ratio of 1:1 and used in place of the layer formed by mixing a compound E-2 and a donor compound (Liq: lithium quinolinol). The results are shown in Table 5.

Examples 41 to 43

In the same manner as in Example 23 except that materials described in Table 5 were used as a second hole transporting layer, light emitting devices were prepared and evaluated. The results are shown in Table 5.

TABLE 1

|  | Second hole transporting layer | Host material | Dopant material | Emitted color | Luminance efficiency (lm/W) | Luminance half-value period (h) |
|---|---|---|---|---|---|---|
| Example 1 | Compound [6] | H-1 | D-1 | Blue | 5.2 | 1600 |
| Example 2 | Compound [24] | H-1 | D-1 | Blue | 4.8 | 1300 |
| Example 3 | Compound [96] | H-1 | D-1 | Blue | 5.0 | 1500 |
| Example 4 | Compound [156] | H-1 | D-1 | Blue | 5.1 | 1500 |
| Comparative Example 1 | HT-2 | H-1 | D-1 | Blue | 3.5 | 800 |
| Comparative Example 2 | HT-3 | H-1 | D-1 | Blue | 3.8 | 700 |
| Comparative Example 3 | HT-4 | H-1 | D-1 | Blue | 3.9 | 700 |
| Comparative Example 4 | HT-5 | H-1 | D-1 | Blue | 3.6 | 750 |
| Comparative Example 5 | HT-6 | H-1 | D-1 | Blue | 3.6 | 760 |
| Comparative Example 6 | HT-7 | H-1 | D-1 | Blue | 3.6 | 800 |

TABLE 2

| | Second Hole transporting layer | Host material | Dopant material | Emitted color | Luminance efficiency (lm/W) | Luminance half-value period (h) |
|---|---|---|---|---|---|---|
| Example 5 | Compound [6] | H-2 | D-2 | Green | 14.0 | 1500 |
| Example 6 | Compound [24] | H-2 | D-2 | Green | 13.5 | 1300 |
| Example 7 | Compound [156] | H-2 | D-2 | Green | 14.5 | 1500 |
| Example 8 | Compound [6] | Compound [6] | D-2 | Green | 15.0 | 1600 |
| Comparative Example 7 | HT-2 | H-2 | D-2 | Green | 9.6 | 900 |
| Comparative Example 8 | HT-3 | H-2 | D-2 | Green | 8.5 | 600 |
| Comparative Example 9 | HT-4 | H-2 | D-2 | Green | 10.3 | 700 |
| Comparative Example 10 | HT-5 | H-2 | D-2 | Green | 7.5 | 600 |
| Comparative Example 11 | HT-6 | H-2 | D-2 | Green | 9.4 | 900 |

TABLE 3

| | Hole transporting layer | Host material | Dopant material | Emitted color | Luminance efficiency (lm/W) | Luminance half-value period (h) |
|---|---|---|---|---|---|---|
| Example 9 | HT-1 | Compound [6] | D-2 | Green | 19.0 | 1600 |
| Example 10 | HT-1 | Compound [24] | D-2 | Green | 17.3 | 1350 |
| Example 11 | HT-1 | Compound [156] | D-2 | Green | 18.5 | 1600 |
| Comparative Example 12 | HT-1 | H-3 | D-2 | Green | 8.5 | 550 |
| Comparative Example 13 | HT-1 | H-4 | D-2 | Green | 9.1 | 560 |
| Comparative Example 14 | HT-1 | HT-3 | D-2 | Green | 7.5 | 700 |
| Comparative Example 15 | HT-1 | HT-4 | D-2 | Green | 9.5 | 750 |
| Comparative Example 16 | HT-1 | HT-6 | D-2 | Green | 8.0 | 750 |
| Comparative Example 17 | HT-1 | H-5 | D-2 | Green | 8.5 | 600 |
| Comparative Example 18 | HT-1 | H-6 | D-2 | Green | 9.0 | 700 |

TABLE 4

| | Second hole transporting layer | Host material | Dopant material | Emitted color | Luminance efficiency (lm/W) | Luminance half-value period (h) |
|---|---|---|---|---|---|---|
| Example 12 | Compound [6] | H-7 | D-3 | Red | 10.3 | 1500 |
| Example 13 | Compound [2] | H-7 | D-3 | Red | 10.1 | 1400 |
| Example 14 | Compound [184] | H-7 | D-3 | Red | 9.8 | 1300 |
| Example 15 | Compound [176] | H-7 | D-3 | Red | 10.0 | 1400 |
| Example 16 | Compound [169] | H-7 | D-3 | Red | 9.6 | 1350 |
| Example 17 | Compound [17] | H-7 | D-3 | Red | 9.8 | 1500 |
| Example 18 | Compound [102] | H-7 | D-3 | Red | 9.8 | 1400 |
| Example 19 | Compound [180] | H-7 | D-3 | Red | 9.7 | 1400 |
| Example 20 | Compound [126] | H-7 | D-3 | Red | 10.3 | 1350 |
| Example 21 | Compound [162] | H-7 | D-3 | Red | 9.9 | 1400 |
| Example 22 | Compound [170] | H-7 | D-3 | Red | 10.0 | 1450 |
| Comparative Example 19 | HT-2 | H-7 | D-3 | Red | 5.6 | 900 |
| Comparative Example 20 | HT-3 | H-7 | D-3 | Red | 5.5 | 800 |
| Comparative Example 21 | HT-5 | H-7 | D-3 | Red | 5.0 | 900 |
| Comparative Example 22 | HT-7 | H-7 | D-3 | Red | 5.4 | 950 |

TABLE 5

| | Hole injection layer | Second hole transporting layer | Host material | Dopant material | Electron transporting layer | Emitted color | Luminance efficiency (lm/W) | Luminance half-value period (h) |
|---|---|---|---|---|---|---|---|---|
| Example 23 | HI-1 | Compound [6] | H-8 | D-4 | E-2/Liq | Green | 50.0 | 5500 |
| Example 24 | HI-1 | Compound [24] | H-8 | D-4 | E-2/Liq | Green | 45.0 | 4500 |
| Example 25 | HI-1 | Compound [156] | H-8 | D-4 | E-2/Liq | Green | 49.0 | 5500 |
| Comparative Example 23 | HI-1 | HT-3 | H-8 | D-4 | E-2/Liq | Green | 28.0 | 2800 |
| Comparative Example 24 | HI-1 | HT-5 | H-8 | D-4 | E-2/Liq | Green | 28.0 | 2700 |
| Comparative Example 25 | HI-1 | HT-6 | H-8 | D-4 | E-2/Liq | Green | 29.0 | 3000 |
| Comparative Example 26 | HI-1 | HT-7 | H-8 | D-4 | E-2/Liq | Green | 23.0 | 2500 |
| Comparative Example 27 | HI-1 | HT-8 | H-8 | D-4 | E-2/Liq | Green | 21.0 | 2500 |
| Example 26 | HT-8/HI-2 | Compound [6] | H-8 | D-4 | E-2/Liq | Green | 55.0 | 6000 |
| Example 27 | HT-8/HI-2 | Compound [24] | H-8 | D-4 | E-2/Liq | Green | 51.0 | 5500 |
| Example 28 | HT-8/HI-2 | Compound [156] | H-8 | D-4 | E-2/Liq | Green | 55.0 | 6100 |
| Example 29 | HT-8/HI-2 | Compound [6] | H-8/H-9 | D-4 | E-2/Liq | Green | 45.0 | 4500 |
| Example 30 | HT-8/HI-2 | Compound [24] | H-8/H-9 | D-4 | E-2/Liq | Green | 41.0 | 4100 |
| Example 31 | HT-8/HI-2 | Compound [156] | H-8/H-9 | D-4 | E-2/Liq | Green | 45.0 | 4400 |
| Example 32 | HI-3 | Compound [6] | H-8 | D-4 | E-2/Liq | Green | 40.0 | 4300 |
| Example 33 | HI-3 | Compound [24] | H-8 | D-4 | E-2/Liq | Green | 38.0 | 4000 |
| Example 34 | HI-3 | Compound [156] | H-8 | D-4 | E-2/Liq | Green | 40.0 | 4200 |
| Example 35 | HT-8/HI-2 | Compound [6] | H-8 | D-4 | E-3 | Green | 51.0 | 5800 |
| Example 36 | HT-8/HI-2 | Compound [6] | H-8 | D-4 | E-4 | Green | 50.0 | 5400 |
| Example 37 | HT-8/HI-2 | Compound [6] | H-8 | D-4 | E-5 | Green | 50.0 | 5800 |
| Comparative Example 28 | HT-8/HI-2 | Compound [6] | H-8 | D-4 | E-6 | Green | 30.0 | 4000 |
| Comparative Example 29 | HT-8/HI-2 | Compound [6] | H-8 | D-4 | E-7 | Green | 27.0 | 3300 |
| Example 38 | HT-8/HI-2 | Compound [6] | H-8 | D-4 | E-2/E-1 | Green | 47.0 | 5800 |
| Example 39 | HT-8/HI-2 | Compound [6] | H-8 | D-4 | E-3/E-1 | Green | 44.0 | 4700 |
| Example 40 | HT-8/HI-2 | Compound [6] | H-8 | D-4 | E-4/E-1 | Green | 46.0 | 5500 |
| Example 41 | HI-1 | Compound [176] | H-8 | D-4 | E-2/Liq | Green | 55.0 | 5800 |
| Example 42 | HI-1 | Compound [193] | H-8 | D-4 | E-2/Liq | Green | 46.0 | 4800 |
| Example 43 | HI-1 | Compound [198] | H-8 | D-4 | E-2/Liq | Green | 43.0 | 5500 |

The invention claimed is:

1. A light emitting device material including a carbazole skeleton-containing compound represented by the following general formula (1):

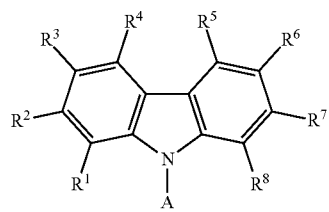

(1)

wherein $R^1$ to $R^8$ may be the same or different and are each selected from the group consisting of hydrogen, an alkyl group, a cycloalkyl group, a heterocyclic group, an alkenyl group, a cycloalkenyl group, an alkynyl group, an alkoxy group, an alkylthio group, an aryl ether group, an aryl thioether group, an aryl group, a heteroaryl group, a halogen, a carbonyl group, a carboxyl group, an oxycarbonyl group, a carbamoyl group, an amino group, a silyl group, and $-P(=O)R^9R^{10}$, and one of $R^1$ to $R^8$ is a group represented by the following general formula (3);

$R^9$ and $R^{10}$ are each an aryl group or a heteroaryl group;

the one $R^1$ to $R^8$ group that is formula (3) is coupled at the position of any of $R^{51}$ to $R^{58}$ in formula (3), or at any position in a group represented by $R^{59}$;

$R^1$ to $R^8$ exclude dibenzofuran skeleton, dibenzothiophene skeleton and carbazole skeleton structures unless these groups are those represented by formula (3);

$R^1$ to $R^{10}$ exclude anthracene skeleton and pyrene skeleton structures; and A is a group represented by the following general formula (2):

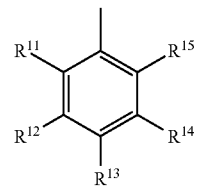

(2)

wherein $R^{11}$ to $R^{15}$ may be the same or different and each is hydrogen or a substituted or unsubstituted aryl group, wherein at least two of $R^{11}$ to $R^{15}$ are substituted or unsubstituted aryl groups, and $R^{11}$ to $R^{15}$ exclude anthracene skeleton and pyrene skeleton structures; and

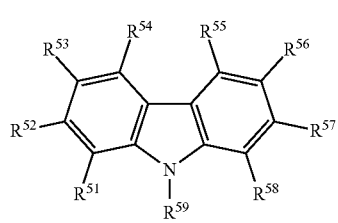

(3)

wherein $R^{51}$ to $R^{58}$ may be the same or different and are each selected from the group consisting of hydrogen, an alkyl group, a cycloalkyl group, a heterocyclic group, an alkenyl group, a cycloalkenyl group, an alkynyl group, an alkoxy group, an alkylthio group, an aryl ether group, an aryl thioether group, an aryl group, a heteroaryl group, a halogen, a carbonyl group, a carboxyl group, an oxycarbonyl group, a carbamoyl group, an amino group, a silyl group and —P(=O)$R^{60}R^{61}$; and $R^{60}$ and $R^{61}$ are each an aryl group or a heteroaryl group, $R^{59}$ may be the same or different and are each selected from the group consisting of an alkyl group, a cycloalkyl group, a heterocyclic group, an alkenyl group, a cycloalkenyl group, an alkynyl group, an alkoxy group, an alkylthio group, an aryl ether group, an aryl thioether group, an aryl group, a heteroaryl group, a halogen, a carbonyl group, a carboxyl group, an oxycarbonyl group, a carbamoyl group, an amino group, a silyl group and —P(=O)$R^{60}R^{61}$; and $R^{60}$ and $R^{61}$ are each an aryl group or a heteroaryl group, wherein the position of any one of $R^{51}$ to $R^{58}$, or any position in a group represented by $R^{59}$ is coupled at the position of any of $R^1$ to $R^8$ in formula (1), $R^{51}$ to $R^{59}$ exclude dibenzofuran skeleton, dibenzothiophene skeleton and carbazole skeleton groups unless these groups are coupled at the position of any of $R^1$ to $R^8$ in formula (1), and $R^{51}$ to $R^{61}$ exclude anthracene skeleton and pyrene skeleton groups.

2. The light emitting device material according to claim 1, wherein in the general formula (1), A and $R^{59}$ are different groups.

3. The light emitting device material according to claim 1, wherein in the general formula (1), at least two of $R^{11}$ to $R^{15}$ are each independently a phenyl group, a phenyl group substituted with an alkyl group, or a phenyl group substituted with a halogen.

4. The light emitting device material according to claim 1, wherein the carbazole skeleton-containing compound represented by the general formula (1) is a carbazole skeleton represented by the general formula (4):

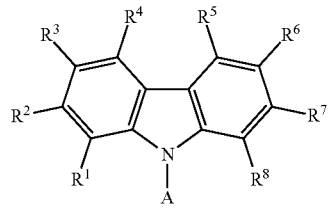

(4)

wherein $R^{16}$ to $R^{23}$ may be the same or different and are each selected from the group consisting of hydrogen, an alkyl group, a cycloalkyl group, a heterocyclic group, an alkenyl group, a cycloalkenyl group, an alkynyl group, an alkoxy group, an alkylthio group, an aryl ether group, an aryl thioether group, an aryl group, a heteroaryl group, a halogen, a carbonyl group, a carboxyl group, an oxycarbonyl group, a carbamoyl group, an amino group, a silyl group, and —P(=O)$R^{24}R^{25}$, and one of $R^{16}$ to $R^{23}$ is a group represented by the following general formula (5); $R^{24}$ and $R^{25}$ are each an aryl group or a heteroaryl group;

the one $R^{16}$ to $R^{23}$ group that is formula (5) is coupled at the position of any of $R^{62}$ to $R^{74}$ in formula (5), $R^{16}$ to $R^{23}$ exclude dibenzofuran skeleton, dibenzothiophene skeleton and carbazole skeleton groups unless these groups are those represented formula (5), and $R^{16}$ to $R^{25}$ exclude anthracene skeleton and pyrene skeleton groups; and

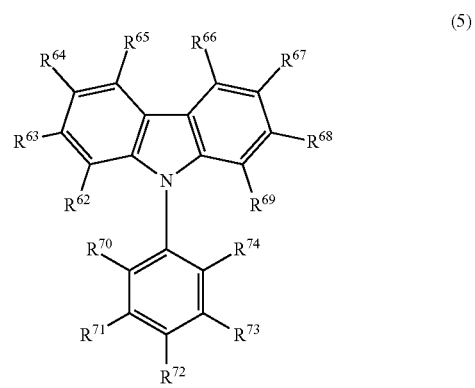

(5)

wherein $R^{62}$ to $R^{74}$ may be the same or different and are each selected from the group consisting of hydrogen, an alkyl group, a cycloalkyl group, a heterocyclic group, an alkenyl group, a cycloalkenyl group, an alkynyl group, an alkoxy group, an alkylthio group, an aryl ether group, an aryl thioether group, an aryl group, a heteroaryl group, a halogen, a carbonyl group, a carboxyl group, an oxycarbonyl group, a carbamoyl group, an amino group, a silyl group and —P(=O)$R^{75}R^{76}$; and $R^{75}$ and $R^{76}$ are each an aryl group or a heteroaryl group, wherein any one of $R^{62}$ to $R^{74}$ is coupled at the position of any of $R^{16}$ to $R^{23}$ in formula (4), $R^{62}$ to $R^{74}$ exclude dibenzofuran skeleton, dibenzothiophene skeleton and carbazole skeleton groups unless these groups are coupled at the position of any of $R^{16}$ to $R^{23}$ in formula (4), and $R^{62}$ to $R^{76}$ exclude anthracene skeleton and pyrene skeleton groups.

5. A light emitting device which has an organic layer between an anode and a cathode and emits light by means of electric energy, wherein the light emitting device contains the light emitting device material according to claim 1 in any of the layers between the anode and the cathode.

6. A light emitting device which has at least a hole transporting layer between an anode and a cathode and emits light by means of electric energy, wherein the light emitting device contains in the hole transporting layer the light emitting device material according to claim 1.

7. A light emitting device which has at least a hole transporting layer and an emissive layer between an anode and a cathode and emits light by means of electric energy, wherein the light emitting device contains in the hole transporting layer the light emitting device material according to claim 1, and contains a triplet emissive material in the emissive layer.

8. A light emitting device which has at least a hole transporting layer and an emissive layer between an anode and a cathode and emits light by means of electric energy, wherein the light emitting device contains in the hole transporting layer light emitting device material according to claim 1, and wherein the emissive layer has a host material and a triplet emissive dopant material, and the light emitting device material of claim 1 is a host material.

9. The light emitting device according to claim 5, wherein a hole injection layer exists between the hole transporting layer and the anode, and the hole injection layer contains an acceptor compound.

10. The light emitting device according to claim 6, wherein a hole injection layer exists between the hole transporting layer and the anode, and the hole injection layer contains an acceptor compound.

11. The light emitting device according to claim 7, wherein a hole injection layer exists between the hole transporting layer and the anode, and the hole injection layer contains an acceptor compound.

12. The light emitting device according to claim 8, wherein a hole injection layer exists between the hole transporting layer and the anode, and the hole injection layer contains an acceptor compound.

13. The light emitting device according to claim 5, wherein at least an electron transporting layer exists between the emissive layer and the cathode, and the electron transporting layer contains a compound containing electron-accepting nitrogen and having a heteroaryl ring structure composed of elements selected from carbon, hydrogen, nitrogen, oxygen, silicon and phosphorus.

14. The light emitting device according to claim 6, wherein at least an electron transporting layer exists between the emissive layer and the cathode, and the electron transporting layer contains a compound containing electron-accepting nitrogen and having a heteroaryl ring structure composed of elements selected from carbon, hydrogen, nitrogen, oxygen, silicon and phosphorus.

15. The light emitting device according to claim 7, wherein at least an electron transporting layer exists between the emissive layer and the cathode, and the electron transporting layer contains a compound containing electron-accepting nitrogen and having a heteroaryl ring structure composed of elements selected from carbon, hydrogen, nitrogen, oxygen, silicon and phosphorus.

16. The light emitting device according to claim 8, wherein at least an electron transporting layer exists between the emissive layer and the cathode, and the electron transporting layer contains a compound containing electron-accepting nitrogen and having a heteroaryl ring structure composed of elements selected from carbon, hydrogen, nitrogen, oxygen, silicon and phosphorus.

17. The light emitting device according to claim 9, wherein at least an electron transporting layer exists between the emissive layer and the cathode, and the electron transporting layer contains a compound containing electron-accepting nitrogen and having a heteroaryl ring structure composed of elements selected from carbon, hydrogen, nitrogen, oxygen, silicon and phosphorus.

* * * * *